(12) United States Patent
Baxter, III et al.

(10) Patent No.: US 10,874,398 B2
(45) Date of Patent: Dec. 29, 2020

(54) FIRING LEVER ASSEMBLY FOR LINEAR SURGICAL STAPLER

(71) Applicant: ETHICON LLC, Guaynabo, PR (US)

(72) Inventors: Chester O. Baxter, III, Loveland, OH (US); Michael J. Stokes, Cincinnati, OH (US); Jason Jones, Cincinnati, OH (US); Matthew S. Corbin, Loveland, OH (US); Carol J. Wynn, Kings Mills, OH (US)

(73) Assignee: Ethicon LLC, Guaynabo, PR (US)

( * ) Notice: Subject to any disclaimer, the term of this patent is extended or adjusted under 35 U.S.C. 154(b) by 382 days.

(21) Appl. No.: 15/889,388

(22) Filed: Feb. 6, 2018

(65) Prior Publication Data
US 2019/0239884 A1    Aug. 8, 2019

(51) Int. Cl.
*A61B 17/03* (2006.01)
*A61B 17/115* (2006.01)
(Continued)

(52) U.S. Cl.
CPC ...... *A61B 17/115* (2013.01); *A61B 17/07207* (2013.01); *A61B 17/1114* (2013.01); *A61B 2017/00367* (2013.01); *A61B 2017/00446* (2013.01); *A61B 2017/00477* (2013.01); *A61B 2017/0725* (2013.01);
(Continued)

(58) Field of Classification Search
CPC .......................... A61B 17/068; A61B 17/07207
See application file for complete search history.

(56) References Cited

U.S. PATENT DOCUMENTS

| | | | |
|---|---|---|---|
| 960,300 | A | 6/1910 | Fischer |
| 3,078,465 | A | 2/1963 | Bobrov |

(Continued)

FOREIGN PATENT DOCUMENTS

| | | |
|---|---|---|
| CN | 103 190 938 A | 7/2013 |
| CN | 103 845 093 A | 6/2014 |

(Continued)

OTHER PUBLICATIONS

U.S. Appl. No. 15/889,363, filed Feb. 6, 2018.
(Continued)

*Primary Examiner* — Andrew M Tecco
*Assistant Examiner* — Eyamindae C Jallow
(74) *Attorney, Agent, or Firm* — Frost Brown Todd LLC

(57) ABSTRACT

A handle assembly includes two arms and a latching lever. An end effector includes two jaws. A firing assembly includes an actuating beam, a proximal body, and two levers. The actuating beam is slidable relative to the handle assembly and the end effector. The proximal body is coupled to the actuating beam and is housed within either the first arm or the second arm. The first lever is configured to move between a first laterally extending position and a first non-obtrusive position. The first lever is configured to drive the actuating beam and the proximal body relative to the handle assembly in the first laterally extending position. The second lever is configured to move between a second laterally extending position and a second non-obtrusive position. The second lever is configured to drive the actuating beam and the proximal body relative to the handle assembly in the second laterally extending position.

20 Claims, 41 Drawing Sheets

(51) Int. Cl.
*A61B 17/072* (2006.01)
*A61B 17/11* (2006.01)
*A61B 17/00* (2006.01)
*A61B 90/00* (2016.01)

(52) U.S. Cl.
CPC .............. *A61B 2017/07285* (2013.01); *A61B 2090/037* (2016.02); *A61B 2090/0801* (2016.02); *A61B 2090/0813* (2016.02); *A61B 2090/0814* (2016.02); *A61B 2090/08021* (2016.02)

(56) References Cited

U.S. PATENT DOCUMENTS

| | | |
|---|---|---|
| 3,079,606 A | 3/1963 | Bobrov et al. |
| 3,315,863 A | 4/1967 | O'Dea |
| 3,317,105 A | 5/1967 | Astafjev et al. |
| 3,490,675 A | 1/1970 | Green et al. |
| 4,111,206 A | 9/1978 | Vishnevsky et al. |
| 4,241,861 A | 12/1980 | Fleischer |
| 4,290,542 A | 9/1981 | Fedotov et al. |
| D272,851 S | 2/1984 | Green et al. |
| D272,852 S | 2/1984 | Green et al. |
| 4,429,695 A | 2/1984 | Green |
| 4,520,817 A | 6/1985 | Green |
| 4,596,351 A | 6/1986 | Fedotov et al. |
| 4,605,001 A | 8/1986 | Rothfuss et al. |
| D285,836 S | 9/1986 | Hunt et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,869,415 A | 9/1989 | Fox |
| 4,892,244 A | 1/1990 | Fox et al. |
| 4,955,898 A | 9/1990 | Matsutani et al. |
| 5,065,929 A | 11/1991 | Schulze et al. |
| 5,083,695 A | 1/1992 | Foslien et al. |
| 5,129,570 A | 7/1992 | Schulze et al. |
| 5,141,144 A | 8/1992 | Foslien et al. |
| 5,156,614 A | 10/1992 | Green et al. |
| 5,173,133 A | 12/1992 | Morin et al. |
| 5,221,036 A | 6/1993 | Takase |
| 5,417,361 A | 5/1995 | Williamson, IV |
| 5,445,304 A | 8/1995 | Plyley et al. |
| 5,452,837 A | 9/1995 | Williamson, IV et al. |
| 5,465,896 A | 11/1995 | Allen et al. |
| 5,489,058 A | 2/1996 | Plyley et al. |
| 5,505,363 A | 4/1996 | Green et al. |
| 5,535,935 A | 7/1996 | Vidal et al. |
| 5,542,594 A | 8/1996 | McKean et al. |
| 5,562,241 A | 10/1996 | Knodel et al. |
| 5,586,711 A | 12/1996 | Plyley et al. |
| 5,636,779 A | 6/1997 | Palmer |
| 5,651,491 A | 7/1997 | Heaton et al. |
| 5,653,373 A | 8/1997 | Green et al. |
| 5,655,698 A | 8/1997 | Yoon |
| 5,657,921 A | 8/1997 | Young et al. |
| 5,673,842 A | 10/1997 | Bittner et al. |
| 5,680,983 A | 10/1997 | Plyley et al. |
| 5,718,359 A | 2/1998 | Palmer et al. |
| 5,785,232 A | 7/1998 | Vidal et al. |
| 5,816,471 A | 10/1998 | Plyley et al. |
| 5,871,135 A | 2/1999 | Williamson, IV et al. |
| 5,908,427 A | 6/1999 | McKean et al. |
| 5,988,479 A | 11/1999 | Palmer |
| 6,045,560 A | 4/2000 | McKean et al. |
| 6,131,789 A | 10/2000 | Schulze et al. |
| 6,155,473 A | 12/2000 | Tompkins et al. |
| 6,206,903 B1 | 3/2001 | Ramans |
| 7,032,799 B2 | 4/2006 | Viola et al. |
| 7,055,730 B2 | 6/2006 | Ehrenfels et al. |
| 7,121,446 B2 | 10/2006 | Arad et al. |
| 7,140,527 B2 | 11/2006 | Ehrenfels et al. |
| 7,188,758 B2 | 3/2007 | Viola et al. |
| 7,207,471 B2 | 4/2007 | Heinrich et al. |
| 7,210,609 B2 | 5/2007 | Leiboff et al. |
| 7,238,195 B2 | 7/2007 | Viola |
| 7,278,563 B1 | 10/2007 | Green |
| 7,293,685 B2 | 11/2007 | Ehrenfels et al. |
| 7,326,232 B2 | 2/2008 | Viola et al. |
| 7,334,717 B2 | 2/2008 | Rethy et al. |
| 7,407,078 B2 | 8/2008 | Shelton, IV et al. |
| 7,419,081 B2 | 9/2008 | Ehrenfels et al. |
| 7,422,139 B2 | 9/2008 | Shelton, IV et al. |
| 7,431,730 B2 | 10/2008 | Viola |
| 7,472,815 B2 | 1/2009 | Shelton, IV et al. |
| 7,472,816 B2 | 1/2009 | Holsten et al. |
| 7,490,749 B2 | 2/2009 | Schall et al. |
| 7,543,729 B2 | 6/2009 | Ivanko |
| 7,568,604 B2 | 8/2009 | Ehrenfels et al. |
| 7,571,845 B2 | 8/2009 | Viola |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,410 B2 | 12/2009 | Marczyk |
| 7,641,091 B2 | 1/2010 | Olson et al. |
| 7,665,647 B2 | 2/2010 | Shelton, IV et al. |
| 7,717,312 B2 | 5/2010 | Beetel |
| 7,721,933 B2 | 5/2010 | Ehrenfels et al. |
| 7,722,610 B2 | 5/2010 | Viola et al. |
| 7,740,160 B2 | 6/2010 | Viola |
| 7,744,628 B2 | 6/2010 | Viola |
| 7,766,209 B2 | 8/2010 | Baxter, III et al. |
| 7,810,691 B2 | 10/2010 | Boyden et al. |
| 7,815,092 B2 | 10/2010 | Whitman et al. |
| 7,828,189 B2 | 11/2010 | Holsten et al. |
| 7,837,081 B2 | 11/2010 | Holsten et al. |
| 7,866,528 B2 | 1/2011 | Olson et al. |
| 7,905,381 B2 | 3/2011 | Baxter, III et al. |
| 7,931,182 B2 | 4/2011 | Boyden et al. |
| 7,942,300 B2 | 5/2011 | Rethy et al. |
| 7,954,685 B2 | 6/2011 | Viola |
| 7,954,686 B2 | 6/2011 | Baxter, III et al. |
| 7,997,469 B2 | 8/2011 | Olson et al. |
| 8,006,888 B2 | 8/2011 | Viola |
| 8,028,884 B2 | 10/2011 | Sniffin et al. |
| 8,070,035 B2 | 12/2011 | Holsten et al. |
| 8,074,861 B2 | 12/2011 | Ehrenfels et al. |
| 8,091,754 B2 | 1/2012 | Ehrenfels et al. |
| 8,113,407 B2 | 2/2012 | Holsten et al. |
| 8,127,975 B2 | 3/2012 | Olson et al. |
| 8,141,762 B2 | 3/2012 | Bedi et al. |
| 8,152,041 B2 | 4/2012 | Kostrzewski |
| 8,157,153 B2 | 4/2012 | Shelton, IV et al. |
| 8,231,040 B2 | 7/2012 | Zemlok et al. |
| 8,245,901 B2 | 8/2012 | Stopek |
| 8,256,655 B2 | 9/2012 | Sniffin et al. |
| 8,257,634 B2 | 9/2012 | Scirica |
| 8,267,300 B2 | 9/2012 | Boudreaux |
| 8,272,552 B2 | 9/2012 | Holsten et al. |
| 8,292,146 B2 | 10/2012 | Holsten et al. |
| 8,292,148 B2 | 10/2012 | Viola |
| 8,308,043 B2 | 11/2012 | Bindra et al. |
| 8,336,753 B2 | 12/2012 | Olson et al. |
| 8,348,129 B2 | 1/2013 | Bedi et al. |
| 8,418,907 B2 | 4/2013 | Johnson et al. |
| 8,464,922 B2 | 6/2013 | Marczyk |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,505,801 B2 | 8/2013 | Ehrenfels et al. |
| 8,544,712 B2 | 10/2013 | Jankowski |
| 8,579,178 B2 | 11/2013 | Holsten et al. |
| 8,636,193 B2 | 1/2014 | Whitman et al. |
| 8,636,939 B2 | 1/2014 | Czernik et al. |
| 8,679,156 B2 | 3/2014 | Smith et al. |
| 8,708,210 B2 | 4/2014 | Zemlok et al. |
| 8,728,118 B2 | 5/2014 | Hinman et al. |
| 8,789,740 B2 | 7/2014 | Baxter, III et al. |
| 8,905,287 B2 | 12/2014 | Racenet et al. |
| 8,915,930 B2 | 12/2014 | Huitema et al. |
| 9,016,541 B2 | 4/2015 | Viola et al. |
| 9,119,617 B2 | 9/2015 | Souls et al. |
| 9,364,219 B2 | 6/2016 | Olson et al. |

(56) References Cited

U.S. PATENT DOCUMENTS

| | | |
|---|---|---|
| 9,402,629 B2 | 8/2016 | Ehrenfels et al. |
| 9,439,649 B2 | 9/2016 | Shelton, IV et al. |
| 9,451,959 B2 | 9/2016 | Patankar et al. |
| 9,474,525 B2 | 10/2016 | Smith et al. |
| 9,498,213 B2 | 11/2016 | Marczyk et al. |
| 9,561,030 B2 | 2/2017 | Zhang et al. |
| 9,629,812 B2 | 4/2017 | Widenhouse et al. |
| 9,636,113 B2 | 5/2017 | Wenchell |
| 9,636,128 B2 | 5/2017 | Zemlok et al. |
| 9,681,873 B2 | 6/2017 | Smith et al. |
| 9,693,775 B2 | 7/2017 | Agarwal et al. |
| 9,750,502 B2 | 9/2017 | Scirica et al. |
| 9,867,616 B2 | 1/2018 | Marczyk |
| 2005/0222616 A1* | 10/2005 | Rethy ............... A61B 17/105 606/215 |
| 2006/0180633 A1 | 8/2006 | Emmons |
| 2007/0119901 A1 | 5/2007 | Ehrenfels et al. |
| 2007/0145096 A1 | 6/2007 | Viola et al. |
| 2009/0173766 A1* | 7/2009 | Wenchell ......... A61B 17/07207 227/178.1 |
| 2009/0255974 A1 | 10/2009 | Viola |
| 2009/0308907 A1* | 12/2009 | Nalagatla ......... A61B 17/07207 227/175.2 |
| 2010/0133317 A1 | 6/2010 | Shelton, IV et al. |
| 2010/0294828 A1* | 11/2010 | Bindra ............. A61B 17/07207 227/176.1 |
| 2011/0290856 A1 | 12/2011 | Shelton, IV et al. |
| 2012/0046689 A1 | 2/2012 | Crisuolo et al. |
| 2012/0286022 A1 | 11/2012 | Olson et al. |
| 2012/0312858 A1* | 12/2012 | Patankar .......... A61B 17/07207 227/176.1 |
| 2012/0312859 A1* | 12/2012 | Gupta ............... A61B 17/068 227/176.1 |
| 2012/0312861 A1* | 12/2012 | Gurumurthy ......... A61B 90/94 227/177.1 |
| 2013/0037594 A1* | 2/2013 | Dhakad ............ A61B 17/07207 227/175.2 |
| 2013/0037595 A1* | 2/2013 | Gupta ............. A61B 17/07207 227/175.2 |
| 2013/0037597 A1* | 2/2013 | Katre ............... A61B 17/07207 227/176.1 |
| 2013/0186935 A1 | 7/2013 | Edoga et al. |
| 2013/0190732 A1 | 7/2013 | Slisz et al. |
| 2014/0103091 A1 | 4/2014 | Whitman et al. |
| 2015/0327855 A1 | 11/2015 | Katre et al. |
| 2016/0157890 A1 | 6/2016 | Drake et al. |
| 2016/0262756 A1 | 9/2016 | Patankar et al. |
| 2020/0029966 A1* | 1/2020 | Zhan ............... A61B 17/07207 |

FOREIGN PATENT DOCUMENTS

| | | |
|---|---|---|
| EP | 0033548 B1 | 5/1986 |
| EP | 0178940 B1 | 1/1991 |
| EP | 0669104 A1 | 8/1995 |
| EP | 0770355 A1 | 5/1997 |
| EP | 1382303 B1 | 6/2006 |
| EP | 1702567 A2 | 9/2006 |
| EP | 1728475 A2 | 12/2006 |
| EP | 1977701 B1 | 12/2011 |
| EP | 2452636 A2 | 5/2012 |
| EP | 2305137 B1 | 12/2012 |
| EP | 2308390 B1 | 12/2012 |
| EP | 1693007 B1 | 10/2013 |
| EP | 2 700 366 A1 | 2/2014 |
| EP | 1862129 B1 | 4/2014 |
| EP | 2550920 B1 | 1/2015 |
| EP | 2532313 B1 | 4/2016 |
| EP | 2532312 B1 | 12/2016 |
| EP | 3155988 A1 | 4/2017 |
| GB | 927936 A | 6/1963 |
| JP | 2001-502575 A | 2/2001 |
| JP | 2007-000657 A | 1/2007 |
| SU | 599799 A1 | 4/1978 |
| WO | WO 1999/045849 A1 | 9/1999 |
| WO | WO 2002/030297 A2 | 4/2002 |
| WO | WO 2003/030742 A2 | 4/2003 |
| WO | WO 2003/094743 A1 | 11/2003 |
| WO | WO 2003/094745 A1 | 11/2003 |
| WO | WO 2003/094746 A1 | 11/2003 |
| WO | WO 2003/094747 A1 | 11/2003 |
| WO | WO 2003/079909 A3 | 3/2004 |
| WO | WO 2004/032763 A2 | 4/2004 |
| WO | WO 2007/127283 A2 | 11/2007 |
| WO | WO 2015/065485 A1 | 5/2015 |
| WO | WO 2015/065487 A1 | 5/2015 |

OTHER PUBLICATIONS

U.S. Appl. No. 15/889,370, filed Feb. 6, 2018.
U.S. Appl. No. 15/889,374, filed Feb. 6, 2018.
U.S. Appl. No. 15/889,376, filed Feb. 6, 2018.
U.S. Appl. No. 15/889,390, filed Feb. 6, 2018.
European Search Report, Extended, and Written Opinion dated Apr. 17, 2019 for Application No. EP 19155449.2, 10 pgs.
European Examination Report dated Mar. 6, 2020 for Application No. EP 19155449.2, 4 pgs.
International Search Report and Written Opinion dated Apr. 17, 2019 for Application No. PCT/IB2019/050360, 13 pgs.

* cited by examiner

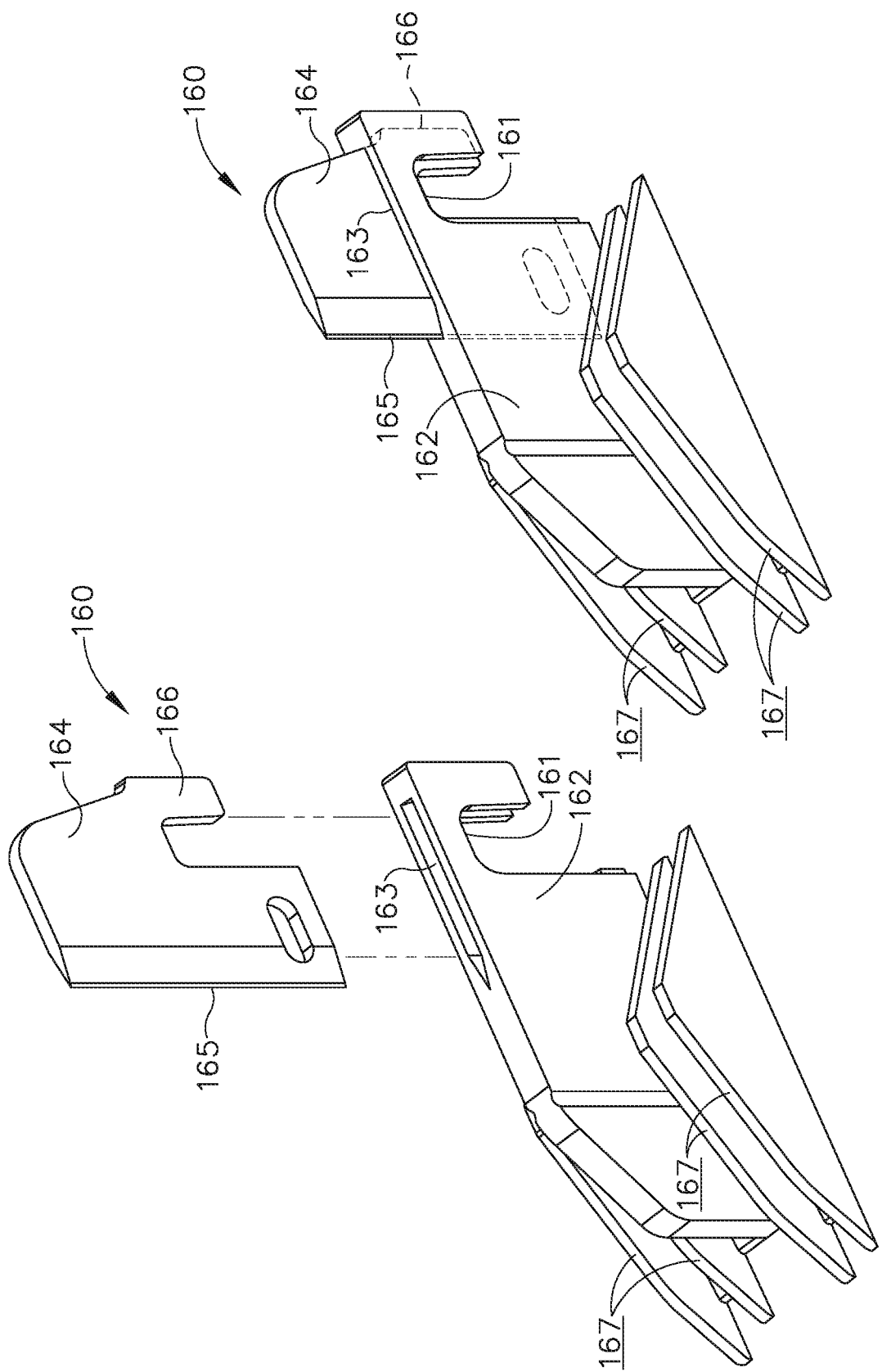

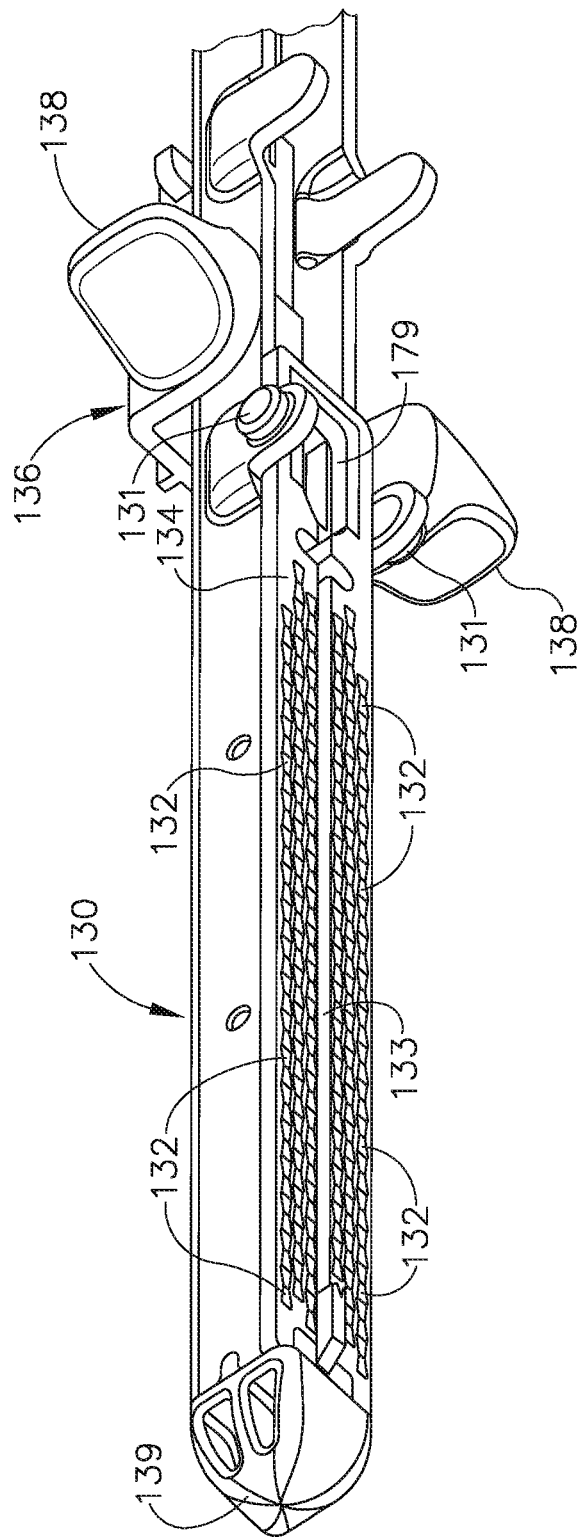

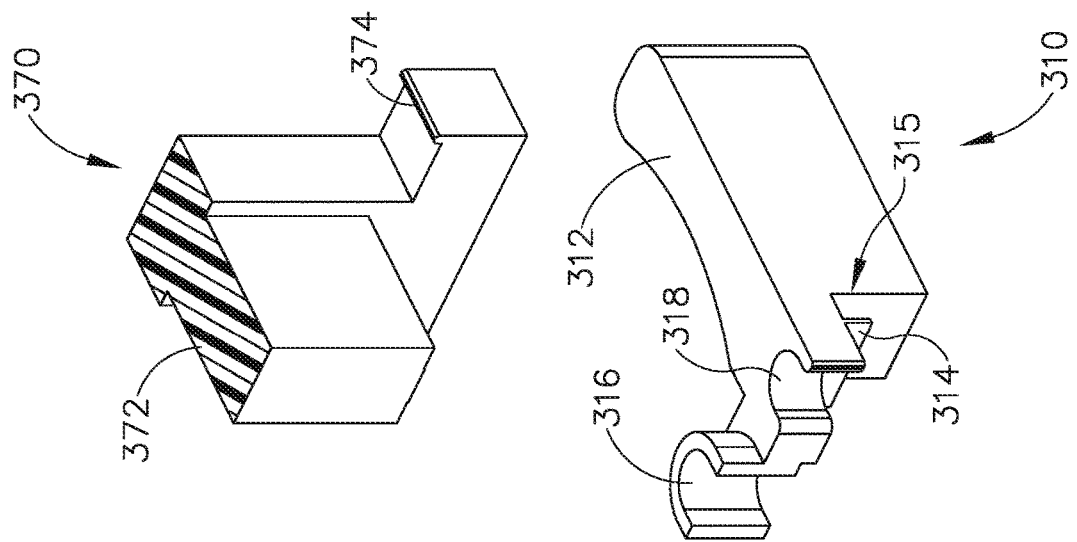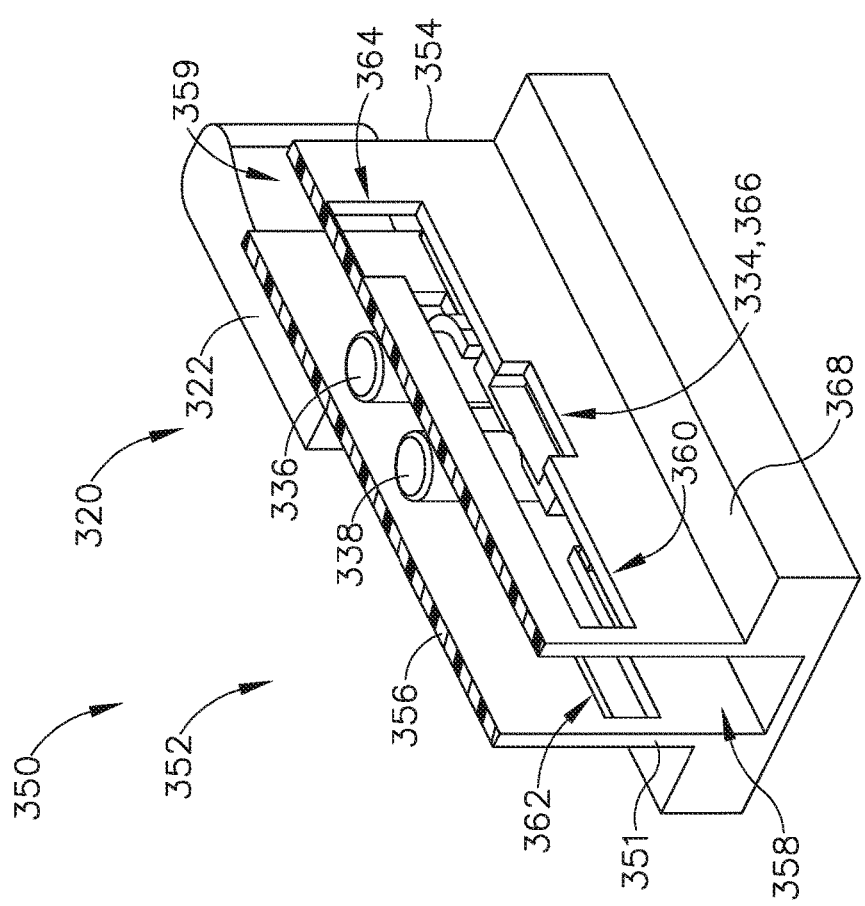
Fig.20A

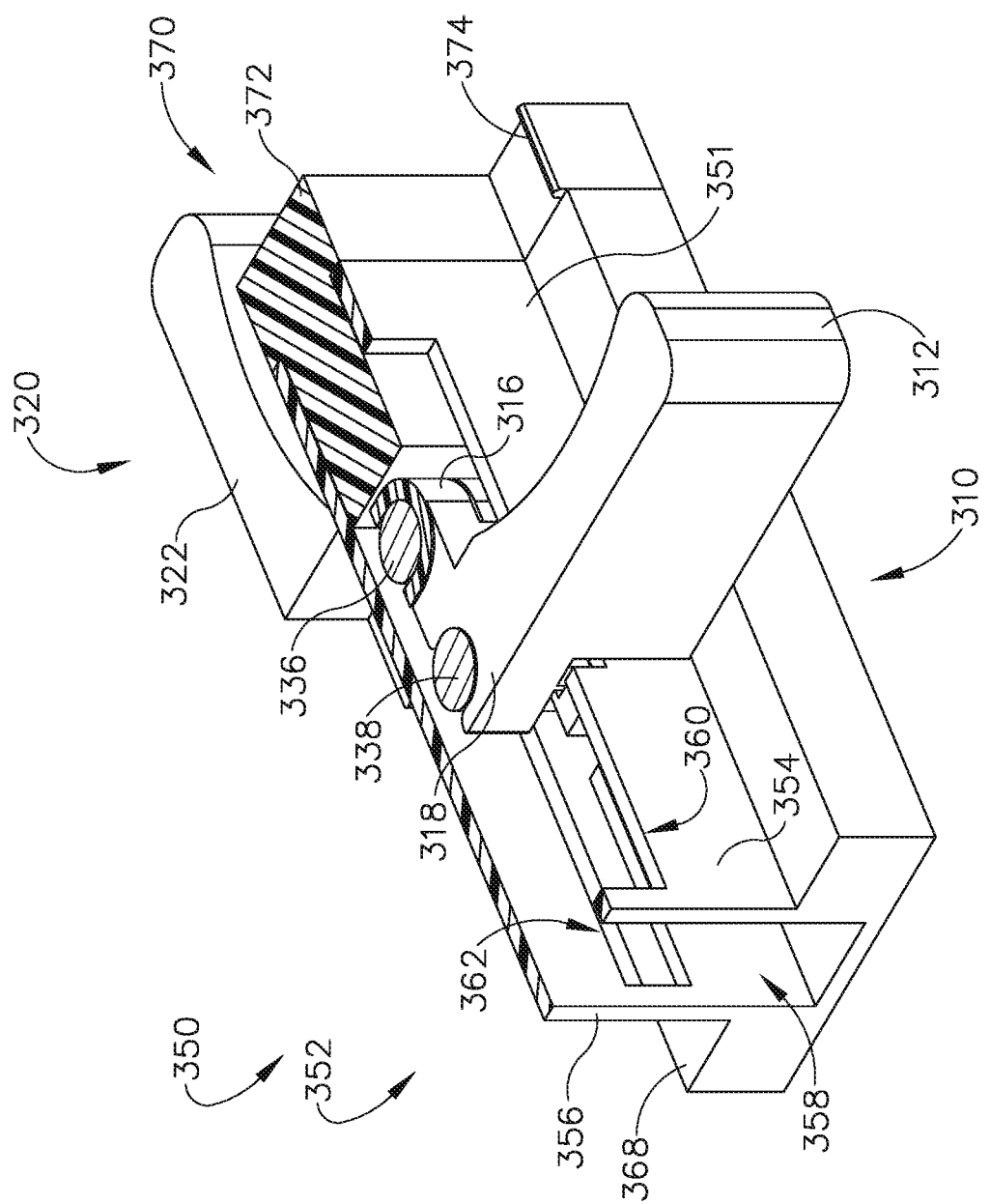

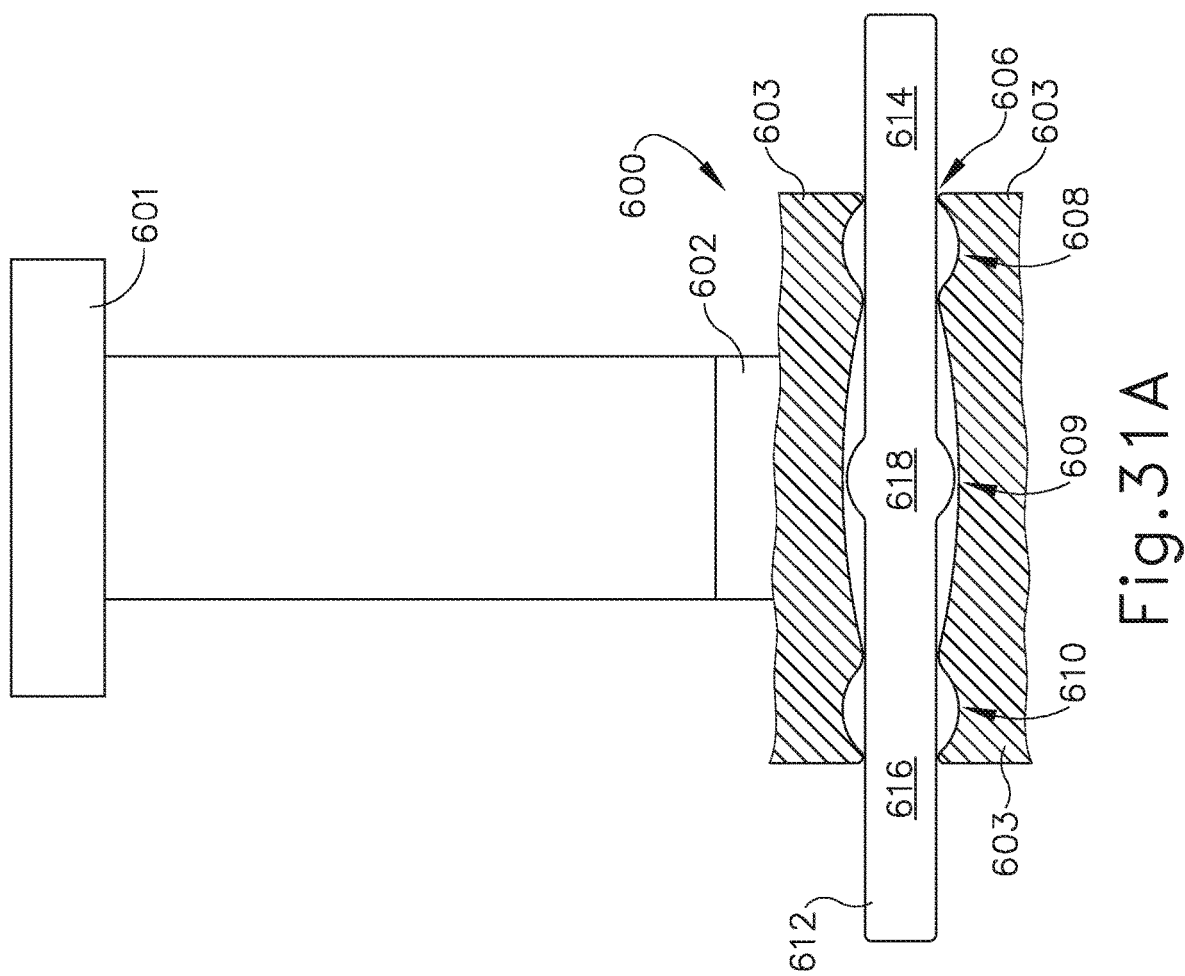

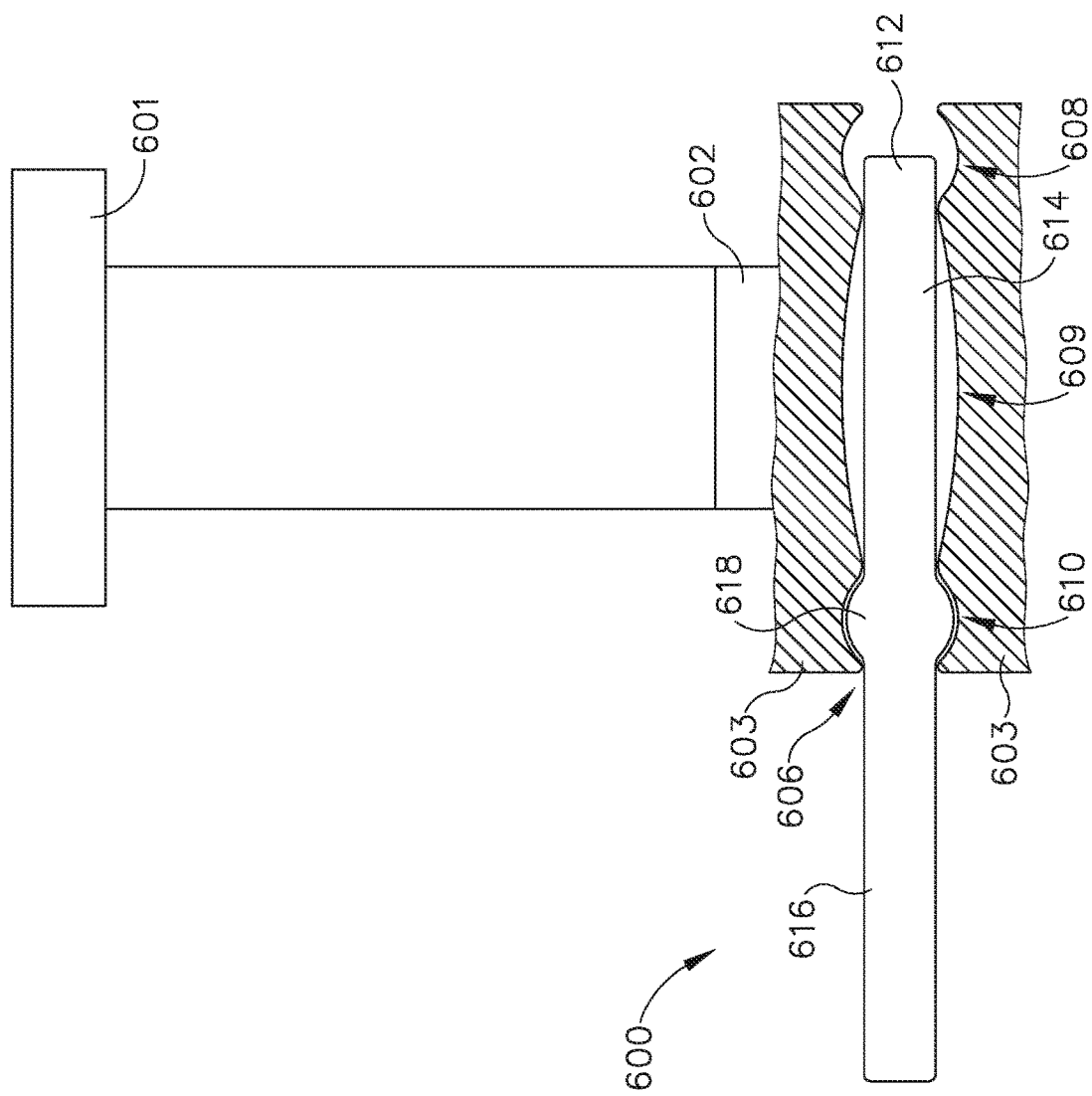

FIRING LEVER ASSEMBLY FOR LINEAR SURGICAL STAPLER

BACKGROUND

In some surgical operations, such as a gastrointestinal anastomosis, it may be desirable to clamp down on one or more layers of tissue, cut through the clamped layers of tissue and drive staples through the layers of tissue to substantially seal the severed layers of tissue together near the severed ends of the tissue layers. One such instrument that may be used in such operations is a linear cutting stapler. A linear cutting stapler generally includes a first jaw, a second jaw, a lever for clamping the first jaw relative to the second jaw, an anvil associated with either the first jaw or the second jaw, a staple cartridge associated with the jaw opposing the staple anvil, and a firing assembly movable relative to the rest of the linear cutting stapler. The first jaw and the second jaw may pivot relative each other in order to grasp tissue between the jaws. Staples are arranged in the staple cartridge such that a portion of firing assembly may actuate through the staple cartridge to drive staples out of staple cartridge, through the tissue, and against anvil while also severing tissue captured between the staple cartridge and the staple anvil.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7 depicts an exploded view of a staple sled assembly of the surgical stapling instrument of FIG. 1;

FIG. 8 depicts a perspective view of the staple sled assembly of FIG. 7;

FIG. 9 depicts a perspective view of an anvil assembly of the surgical stapling instrument of FIG. 1;

FIG. 20A depicts a cross-sectional perspective view of the firing assembly of FIG. 12 being assembled, taken along line 20-20 of FIG. 12, where the first lever of FIG. 17 is aligned for initial insertion within the proximal end of the first portion of FIG. 12, where a distal cap is decoupled from the first portion;

FIG. 23B depicts a cross-sectional perspective view of the firing assembly of FIG. 12, taken along line 23-23 of FIG. 12, where the first lever of FIG. 17 is in a laterally extended, pre-fired, configuration;

FIG. 31A depicts a top plan view of an alternative firing assembly that may be readily incorporated into either surgical stapling instrument of FIG. 1 or FIG. 25, where a firing lever is in a neutral configuration;

FIG. 31B depicts a top plan view of the firing assembly of FIG. 31A, were the firing lever of FIG. 31A is in a first firing configuration;

Figure 1:
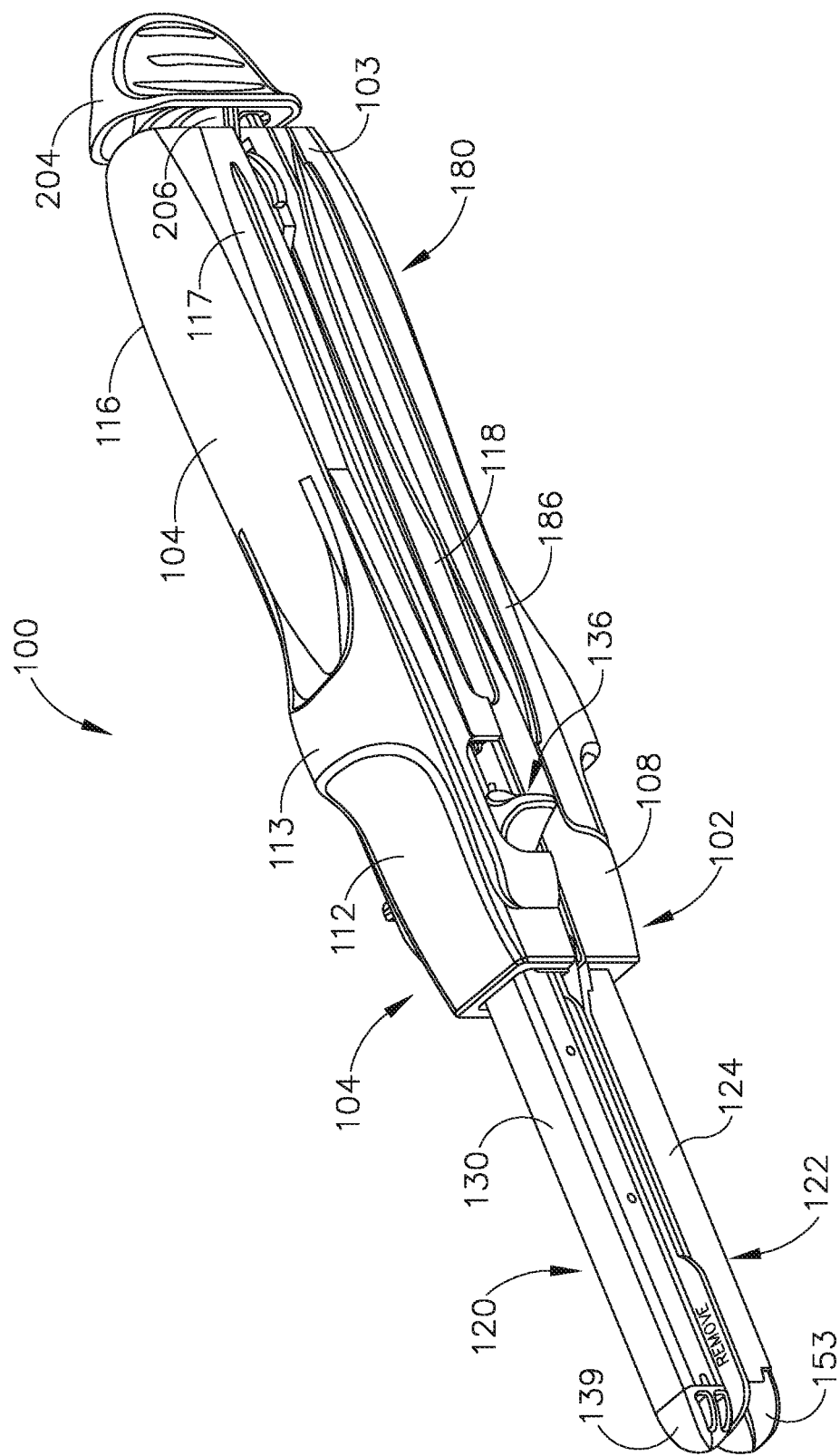
FIG. 1 depicts a perspective view of an exemplary surgical stapling instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal," "distal," "upper," and "lower" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. The terms "proximal," "distal," "upper," and "lower" are thus relative terms and not intended to unnecessarily limit the invention described herein.

I. Overview of Exemplary Linear Cutting Stapler

FIG. 1 depicts an exemplary surgical linear cutting stapler (100) that may be used for any suitable procedure, such as a gastrointestinal anastomosis. Linear cutting stapler (100) includes a first portion (102) having a staple cartridge channel (122), a second portion (104) having an anvil channel (130), a staple cartridge assembly (150) that may selectively couple with cartridge channel (122) of first portion (102), and a firing assembly (200). As will be described in greater detail below, first portion (102) and staple cartridge assembly (150) may pivotably couple with second portion (104) to form an end effector (120) capable of clamping, severing, and stapling tissue captured between opposing halves of end effector (120).

As best seen in FIGS. 3-6, firing assembly (200) includes an actuating beam (202), a staple sled assembly (160)

housed within staple cartridge assembly (150), an actuator (204) (also referred to as a "firing knob"), and a pivot arm (206). Actuating beam (202) extends from a distal end (201) to a proximal end (203). Actuating beam (202) is slidably housed within first portion (102). Pivot arm (206) connects actuator (204) with distal end (201) of actuating beam (202). Actuator (204) and pivot arm (206) may pivot from a proximal position (shown in FIG. 1) to either lateral side of actuating beam (202) (shown in FIG. 11A), thereby enabling an operator to actuate firing assembly (200) from either a first side (116) or a second side (117) of instrument (100) when portions (102, 104) are properly coupled and end effector (120) is in the fully closed position. It should be understood when instrument (100) is properly coupled and end effector (120) is in the fully closed position, first portion (102) and second portion (104) define a slot (118) dimensioned to accommodate translation of actuator (204). In the current example, as will be described in greater detail below, actuating beam (202) is operable to couple with staple sled assembly (160) when staple cartridge assembly (150) is suitably coupled with first portion (102) such that actuator (204) may slide along first side (116) or second side (117) of instrument (100), thereby driving actuating beam (202) and staple sled assembly (160) distally through cartridge assembly (150) to fire instrument (100).

While in the present example, actuator (204) is configured to pivot to either side (116, 117) of instrument (100) to drive actuating beam (202), this is merely optional, as actuator (204) may slidably couple with first portion (102) or second portion (104) through any means apparent to one having ordinary skill in the art in view of the teachings herein. In one example, actuator (204) may strictly associate with first side (116) or second side (117) such that actuator (204) may not pivot when end effector (120) is in the fully closed position. In another example, there may be an actuator (204) positioned on both first side (116) and second side (117), such that instrument (100) may include two actuators (204).

Figure 3:
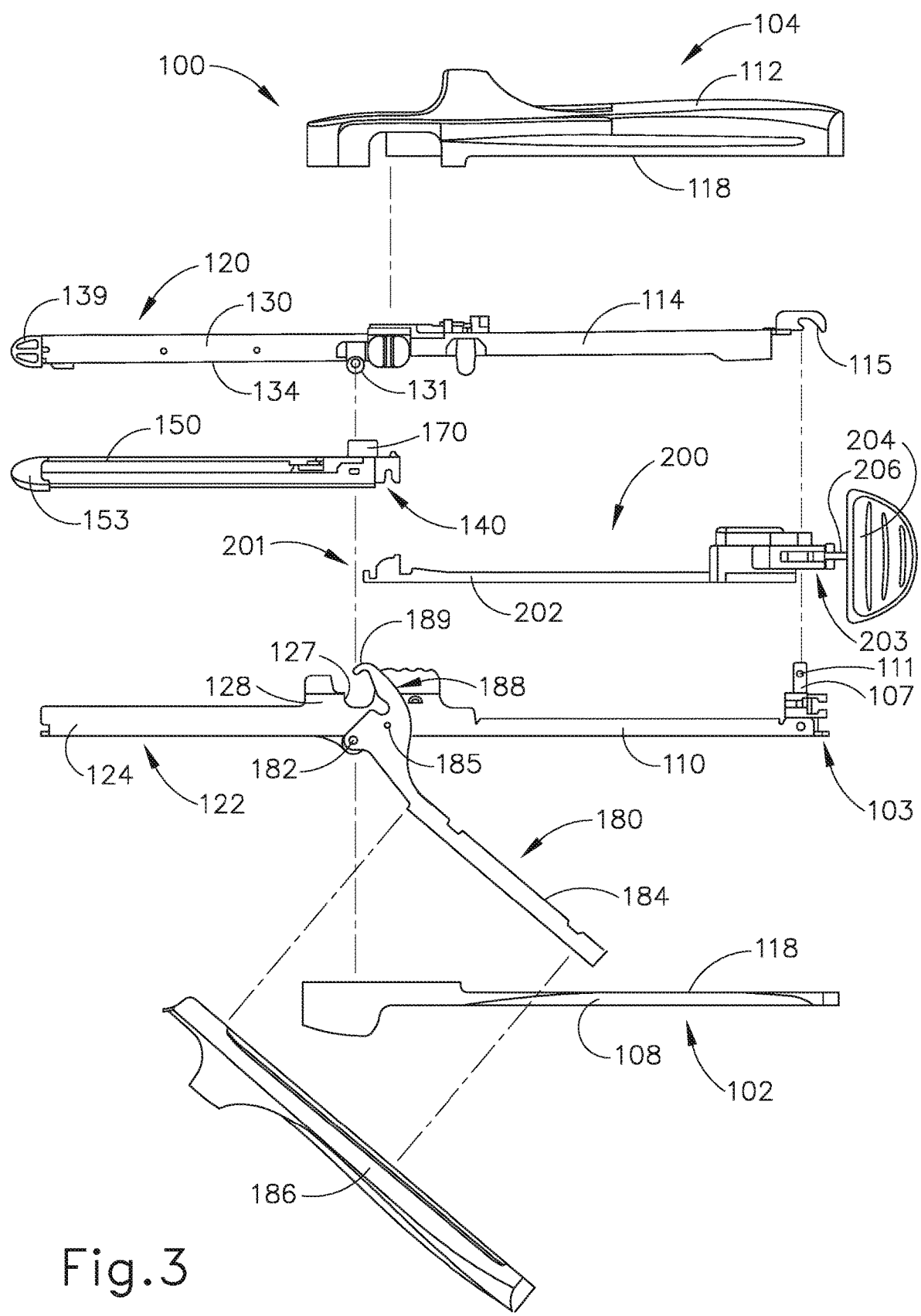
FIG. 3 depicts an exploded elevational side view of the surgical stapling instrument of FIG. 1.

As seen in FIG. 3, first portion (102) includes a first proximal frame (110), staple cartridge channel (122), and a latching lever (180). First proximal frame (110) extends from a proximal end (103) distally into staple cartridge channel (122). In the present example, first proximal frame (110) and staple cartridge channel (122) are formed integrally so as to define an elongate cartridge channel member having a unitary construction. Latching lever (180) is pivotably coupled to either staple cartridge channel (122) or first proximal frame (110) via a pin (182). First proximal frame (110) may be coupled with a handle cover (108) configured to promote sufficient grip such that an operator may control instrument (100) while the operator performs a suitable procedure. Handle cover (108) may couple with first proximal frame (110) by any suitable means as would be apparent to one having ordinary skill in the art in view of the teachings herein. Alternatively, handle cover (108) may be unitarily coupled with first proximal frame (110) or even omitted.

First proximal frame (110) defines a channel that slidably houses actuating beam (202) of firing assembly (200). Proximal end (103) includes one or more lateral pins, or projections (111). Projections (111) are configured to receive grooves (115) of second portion (104) in order to initially pivotably couple first and second portions (102, 104). In the current example, projections (111) are raised from the rest of first proximal frame (110) via a post (107), however this is merely optional. For instance, projections (111) may include a single pin extending laterally across side walls of first proximal frame (110). Of course, any suitable means of initially pivotably couplings first portion (102) and second portion (104) may be used as would be apparent to one having ordinary skill in the art in view of the teachings herein.

Figure 2:
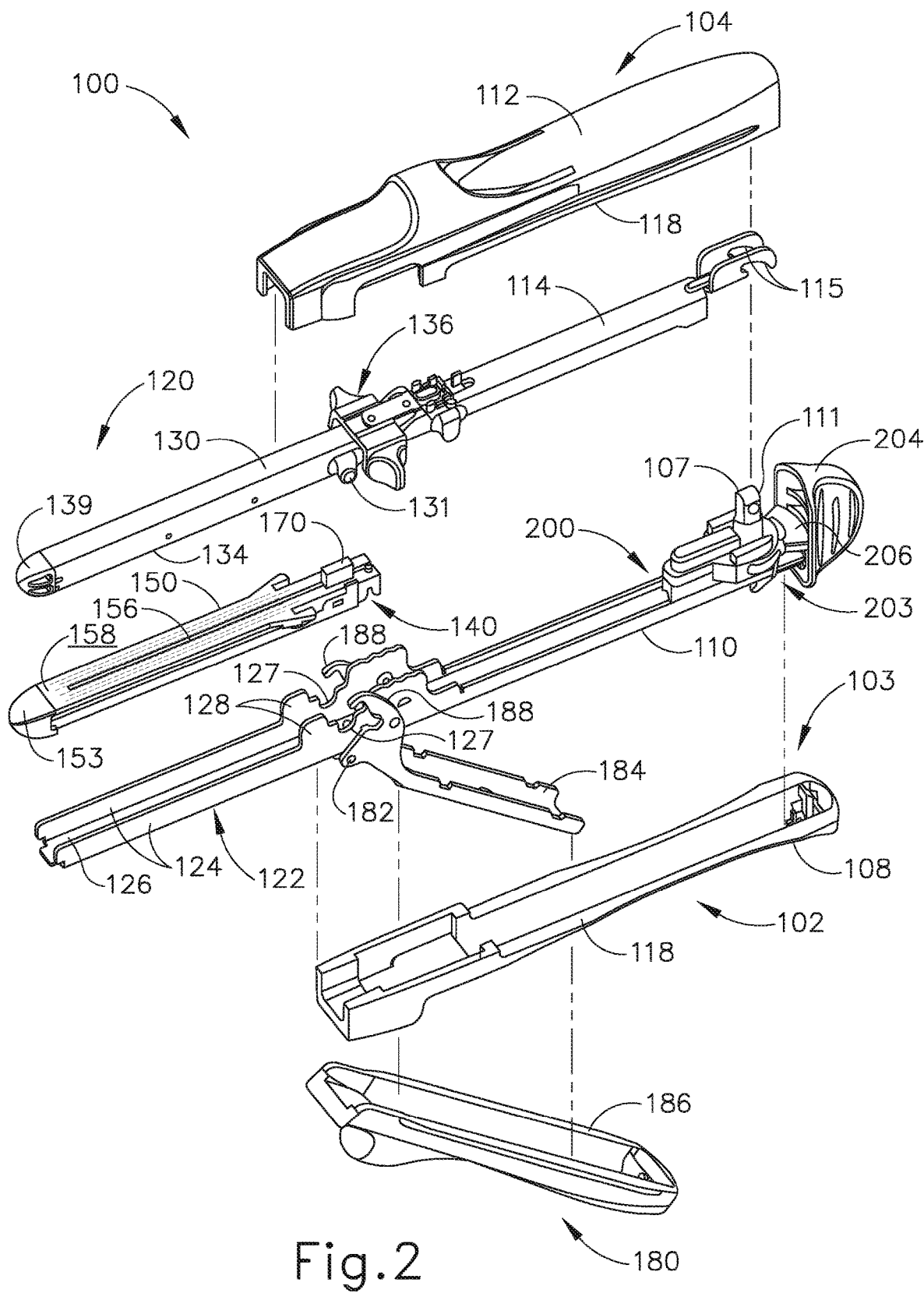
FIG. 2 depicts an exploded perspective view of the surgical stapling instrument of FIG. 1.
Figure 4:
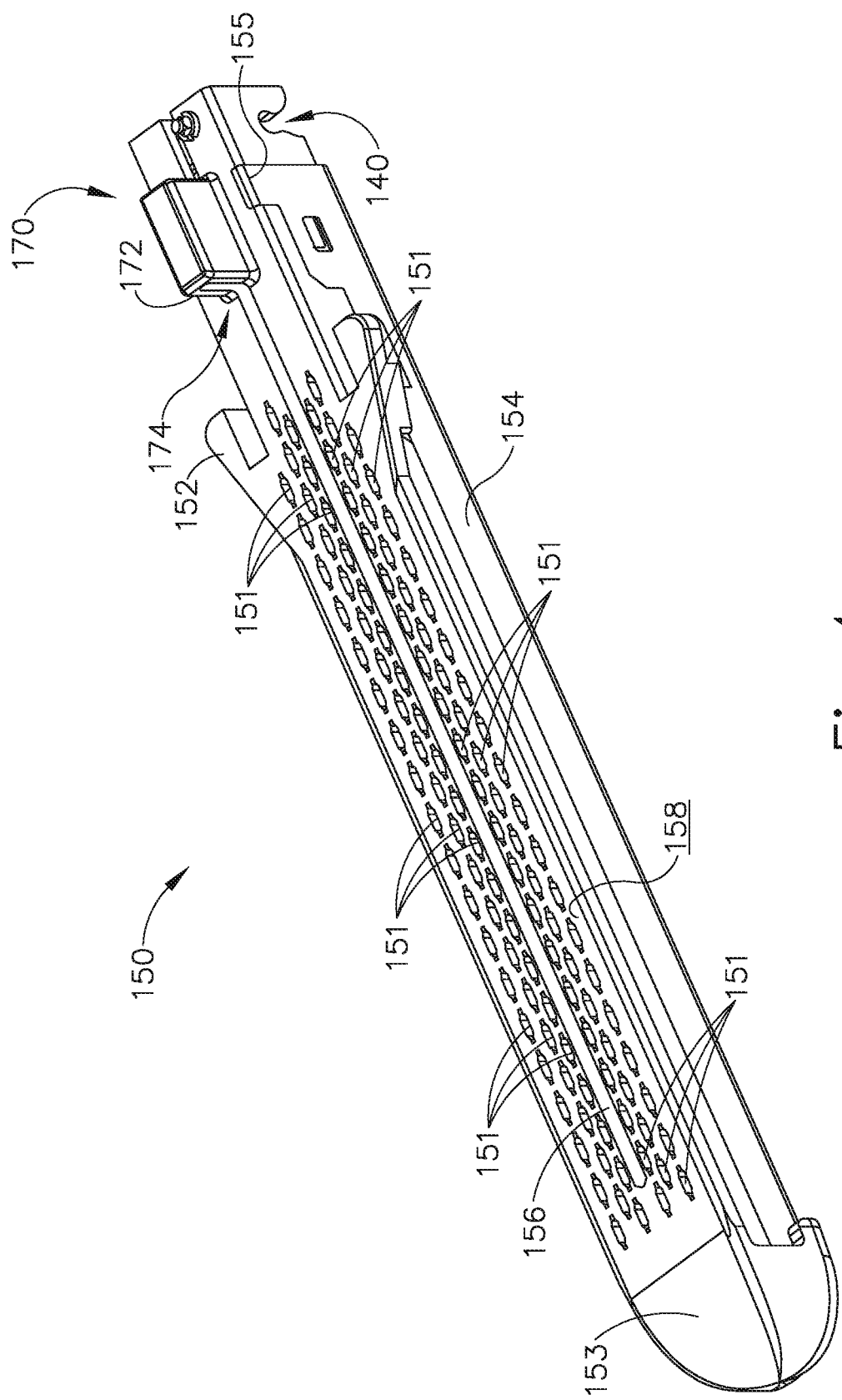
FIG. 4 depicts a perspective view of a staple cartridge assembly of the surgical stapling instrument of FIG. 1.

As briefly mentioned above, staple cartridge channel (122) extends distally from first proximal frame (110). As seen in FIG. 2, staple cartridge channel (122) is dimensioned to selectively couple and decouple with staple cartridge assembly (150). Staple cartridge channel (122) includes a bottom wall (126), and two opposed side walls (124) extending from opposite ends of bottom wall (126). Walls (124, 126) are dimensioned to receive at least a portion of staple cartridge assembly (150), as seen in FIG. 4. Additionally, side walls (124) include inwardly extending lateral projections (not shown) configured to receive coupling cutouts (140) defined by a proximal end of staple cartridge assembly (150). Coupling cutouts (140) may be dimensioned for a snap-fitting or press-fitting with inwardly extending lateral projections (not shown) of side walls (124) such that an operator may selectively attach and detach staple cartridge assembly (150) to staple cartridge channel (122). While coupling cutouts (140) and inwardly extending lateral projections (not shown) are used to selectively couple staple cartridge assembly (150) with staple cartridge channel (122), any other suitable coupling means may be used as would be apparent to one having ordinary skill in the art in view of the teachings herein. Side walls (124) of staple cartridge channel (122) also include side flanges (128) each defining a notch or recess (127). Recesses (127) are dimensioned to receive latch projections (131) of second portion (104) when second portion (104) pivots such that end effector (120) is in a fully closed position (as shown in FIG. 10D) relative to first portion (102).

As briefly mentioned above, latching lever (180) is pivotably coupled to the rest of first portion (102) via pivot pin (182). Latching lever (180) includes a proximal extending arm (184) and a distal latch body (188). Proximal extending arm (184) may be pivoted about pin (182) toward first proximal frame (110) in order to pivot distal latch body (188) toward staple cartridge channel (122) such that distal latch body (188) may engage and pivot second portion (104) toward first portion (102) to transition end effector (120) from a partially closed position (as shown in FIG. 10C) to a fully closed position (as shown in FIG. 10D).

Proximally extending arm (184) may be coupled with an arm cover (186) to promote sufficient grip such that an operator may grasp arm (184) while the operator performs a suitable procedure. Arm cover (186) may be coupled with proximal extending arm (184) by any suitable means as would be apparent to one having ordinary skill in the art in view of the teachings herein. Alternatively, arm cover (186) may be unitarily coupled with proximally extending arm (184) or even omitted.

Distal latch body (188) includes a pair of hooks (189). Distal latch body (188) also defines a corresponding pair of latch cutouts (185) located proximally relative to hooks (189). As will be described is greater detail below, each hook (189) is dimensioned to initially make contact with and then capture a respective latch projection (131) of second portion (104) such that distal latch body (188) may wrap around at least a portion of each latch projection (131) to further pivot second portion (104) toward first portion (102). As will also be described in greater detail below, each latch cutout (185) is dimensioned to receive a respective latch projection (131) when end effector (120) is in the closed position relative to first portion (102).

Figure 5:
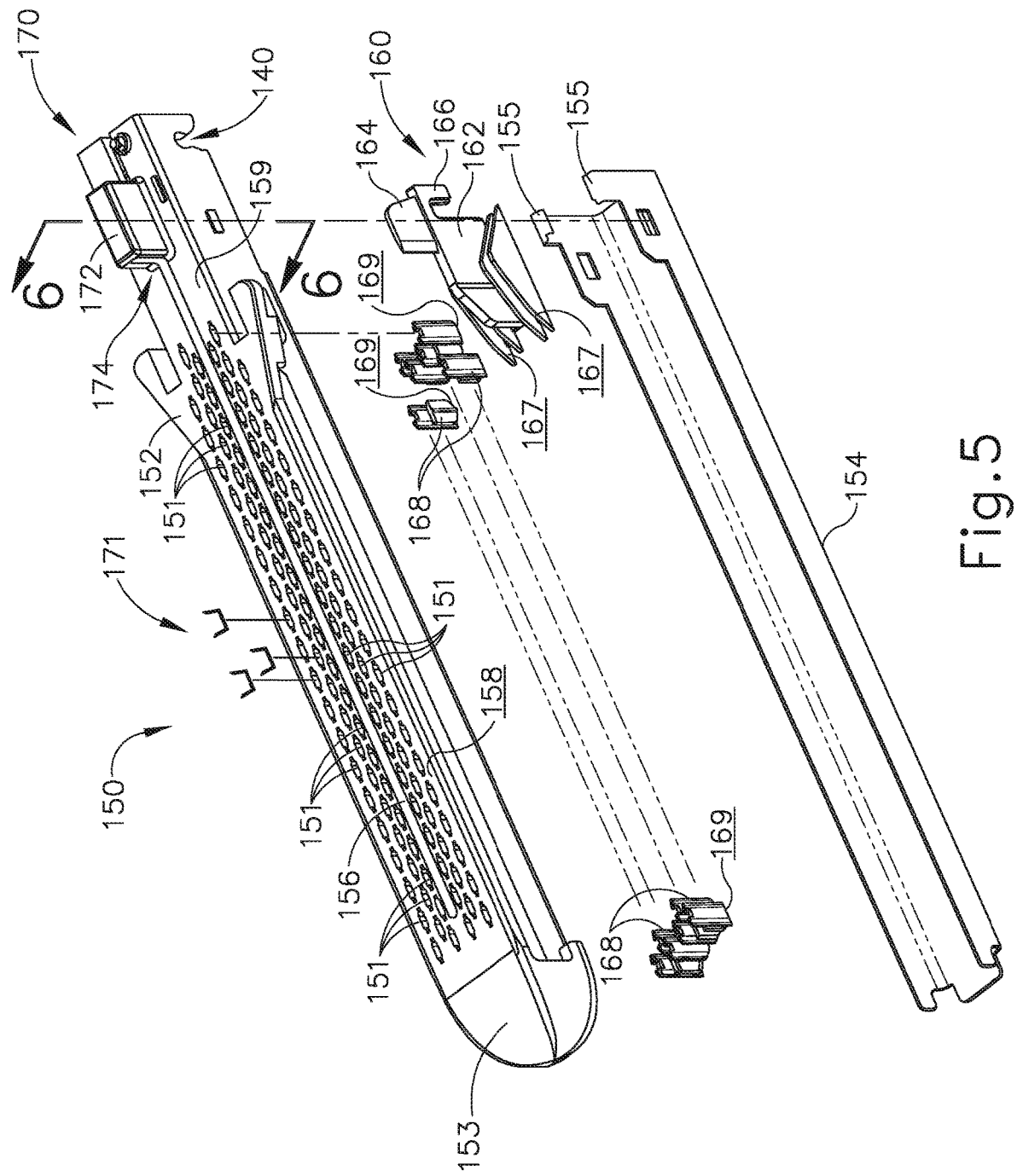
FIG. 5 depicts an exploded view of the staple cartridge assembly of FIG. 4.
Figure 6:
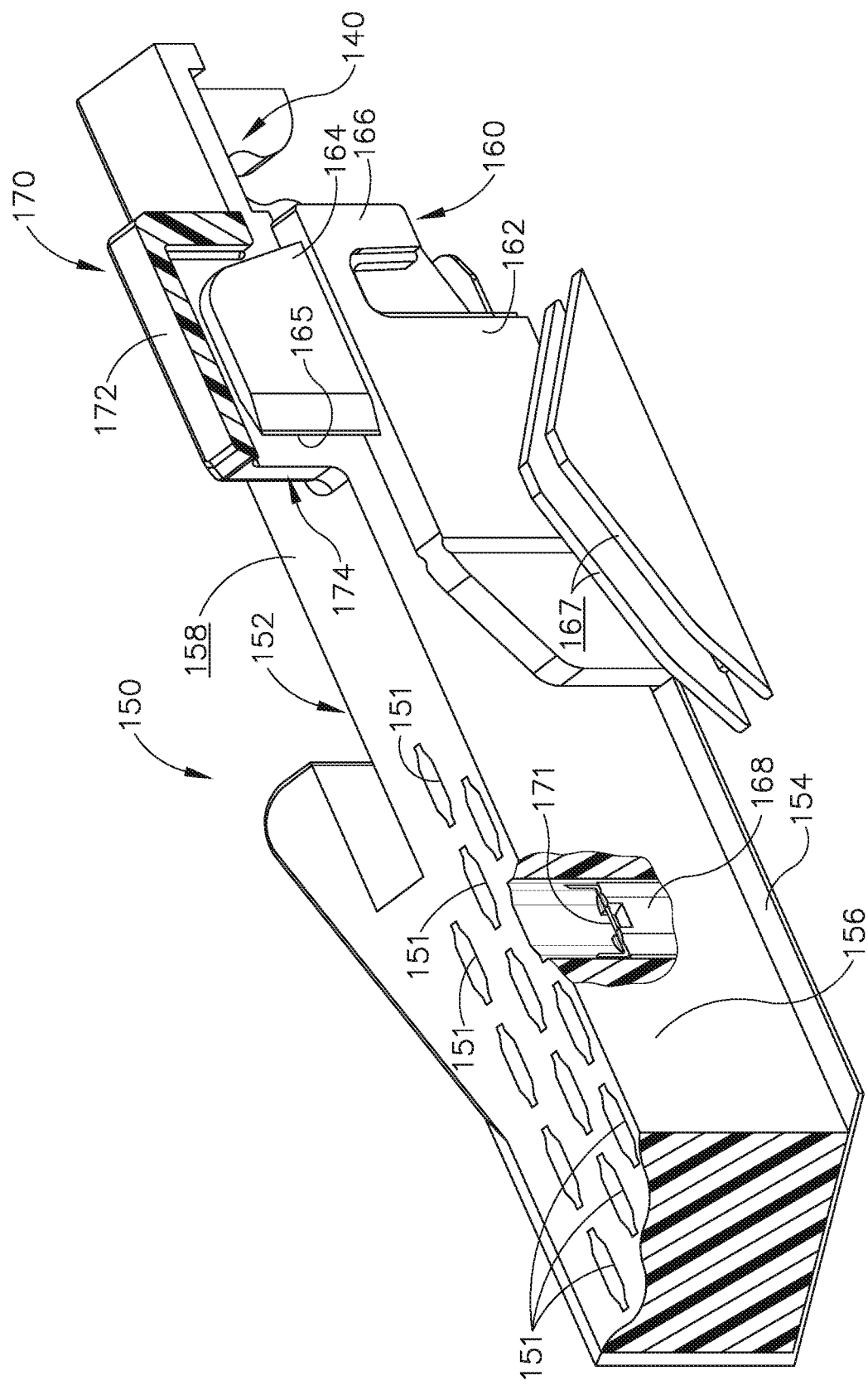
FIG. 6 depicts a cross-sectional perspective view of the staple cartridge assembly of FIG. 4, taken along line 6-6 of FIG. 5.

As best seen in FIGS. 4-6, staple cartridge assembly (150) includes a cartridge body (152), a pan (154), and a plurality of staple drivers (168), each configured to drive a respective staple (171). Cartridge body (152) defines a plurality of staple cavities (151), a slot (156), and coupling cutouts (140). Staple drivers (168) and respective staples (171) are slidably housed within a corresponding staple cavity (151). When first portion (102) and second portion (104) are coupled together, staple cartridge assembly (150) and staple cartridge channel (122) form a portion of end effector (120). As will be described in greater detail below, staple cartridge assembly (150) is configured to house or receive staple sled assembly (160) of firing assembly (200) such that staple sled assembly (160) may actuate through cartridge assembly (150) in order to simultaneously sever and staple tissue captured between the two halves of end effector (120).

As mentioned above, coupling cutouts (140) of cartridge body (152) may be dimensioned for a snap-fitting with inwardly extending lateral projections (not shown) of side walls (124) of staple cartridge channel (122) such that an operator may selectively attach and detach staple cartridge assembly (150) to staple cartridge channel (122). Cartridge body (152) includes a distal nose (153). When staple cartridge assembly (150) is properly coupled with cartridge channel (122), distal nose (153) may extend distally from cartridge channel (122) to provide an atraumatic tip.

Additionally, cartridge body (152) includes a staple deck (158). Staple deck (158) partially defines staple cavities (151) such that staple cavities (151) extend from an interior of cartridge body (152) toward an open end at staple deck (158). Staple cavities (151) each house a corresponding staple driver (168) and staple (171). Similarly, staple deck (158) partially defines slot (156) that extends from an interior of cartridge body (152) toward an open end at staple deck (158). Slot (156) is dimensioned to slidably receive a portion of a sled body (162) and cutting member (164) of staple sled assembly (160) such that cutting member (164) may sever tissue as staple sled assembly (160) slides distally through cartridge body (152).

Pan (154) may include flexible arms (155). Flexible arms (155) may be configured to engage cartridge body (152) such that pan (154) may couple with cartridge body (152) in a snap-fit or press-fit relationship. Pan (154) may couple with cartridge body (152) after staple drivers (168) and staples (171) have been inserted into respective staple cavities (151). Pan (154) may therefore act as a floor for staple drivers (168).

In the current example, cartridge body (152) includes a sled assembly housing (170) located near the proximal end of staple cartridge assembly (150). Sled assembly housing (170) is configured to initially house staple sled assembly (160) of firing assembly (200). Sled assembly housing (170) includes a body (172) defining a cavity (174) having a distally facing opening. Body (172) and cavity (174) are dimensioned to house a cutting member (164) of sled assembly (160) prior to firing, therefore acting as a sheath for cutting member (164). When fired, cutting member (164) may exit sled assembly housing (170) via the distally facing opening of cavity (174).

As seen best in FIGS. 7 and 8, sled assembly (160) includes a sled body (162) and a cutting member (164). Cutting member (164) includes a cutting edge (165) and a lock arm (166). Sled body (162) defines a cutout (161) and a slot (163). Slot (163) is dimensioned to receive a portion of cutting member (164) such that cutting member (164) and sled body (162) may actuate together. Cutting member (164) may couple with sled body (162) via an inference fit with slot (163), through use of adhesives, or any other suitable manner was would be apparent to one having ordinary skill in the art in view of the teachings herein. Alternatively, cutting member (164) may couple with sled body (162) though any suitable manner as would be apparent to one having ordinary skill in the art in view of the teachings herein, such as being unitarily connected, welding, etc. Cutout (161) is dimensioned to couple with distal end (201) of actuating beam (202) when staple cartridge assembly (150) is properly attached to staple cartridge channel (122). Therefore, when properly coupled, actuating beam (202) may drive sled assembly (160) longitudinally through cartridge body (152). It should be understood that since actuating beam (202) is coupled with sled assembly (160) during exemplary use, actuating beam (202) is also dimensioned to slide within slot (156) defined by cartridge body (152).

Sled body (162) also includes a plurality of cam surfaces (167) dimensioned to slide longitudinally within respective elongate grooves (not shown) that pass through staple cavities (151) of cartridge body (152). In particular, cam surfaces (167) are configured to engage and cam against sloped surfaces (169) of staple drivers (168) within staple cavities (151) in order to actuate staple drivers (168) toward staple deck (158). Staple drivers (168) then drive corresponding staples (171) through staple cavities (151) away from staple deck (158).

As mentioned above, staple sled assembly (160) is configured to couple with the rest of firing assembly (200) when staple cartridge assembly (150) is suitably coupled with staple cartridge channel (122). In the current example, staple sled assembly (160) of firing assembly (200) is associated with cartridge assembly (150) such that after cartridge assembly (150) is used and disposed of, so is staple sled assembly (160). Therefore, when an additional cartridge assembly (150) is loaded into staple cartridge channel (122), a new staple sled assembly (160) will be present. However, this is merely optional. For instance, staple sled assembly (160) may be fixed or otherwise coupled to the rest of firing assembly (200) such that the same staple sled assembly (160) may be used multiple times with multiple staple cartridge assemblies (150). In such examples, cartridge body (152) would not need a sled assembly housing (170). Various ways in which staple sled assembly (160) may be incorporated into either staple cartridge assembly (150), staple cartridge channel (122), or first proximal frame (110) will be apparent to one having ordinary skill in the art in view of the teachings herein.

As shown in FIGS. 2 and 3, second portion (104) of instrument (100) includes a second proximal frame (114), anvil channel (130), latch projections (131), and an anvil plate (134). Second proximal frame (114) extends from a proximal end defining grooves (115) in anvil channel (130). In the present example, second proximal frame (114) and anvil channel (130) are formed integrally so as to define an elongate anvil channel member having a unitary construction. Second proximal frame (114) may be coupled with a handle cover (112) configured to promote sufficient grip such that an operator may control instrument (100) while the operator performs a suitable procedure. Handle cover (112) and second proximal frame (114) may couple with each other by any suitable means as would be apparent to one having ordinary skill in the art in view of the teachings herein. Alternatively, handle cover (112) may be unitarily coupled with second proximal frame (114) or even omitted. Second proximal frame (114) may also define a channel configured to enable portions of firing assembly (200) to actuate relative to first portion (102) and second portion (104) when end effector (120) is in the fully closed position (as shown in FIG. 10D).

Second portion (104) terminates distally in a distal nose (139). Distal nose (139) may extend distally from anvil channel (130) to provide an atraumatic tip. As shown in FIG. 9, proximal end of anvil plate (134) defines a recess (179) dimensioned to receive sled assembly housing (170) when first portion (102) and second portion (104) are pivoted toward each other. As will be described in greater detail below, latch projections (131) extend laterally away from anvil channel (130) and are dimensioned to interact with distal latch body (180) to draw anvil plate (134) toward staple cartridge assembly (150).

Anvil plate (134) defines a plurality of staple forming pockets (132) and a slot (133). Staple forming pockets (132) are positioned along anvil plate (134) such that each staple forming pocket (132) aligns with a corresponding staple cavity (151) when anvil channel (130) is pivoted toward staple cartridge channel (122) to the fully closed position (as shown in FIGS. 1, 10D, and 11A-B). Therefore, when cam surfaces (167) of sled body (162) actuate staple drivers (168) in accordance with the description above, staples (171) are driven through staple cavities (151) away from staple deck (158), through tissue, and against a corresponding staple forming pocket (132) such that staples (171) transform from a general "U" shape into a general "B" shape in order to suitably staple tissue. Slot (133) is dimensioned to laterally align with slot (156) of staple cartridge assembly (150) when anvil channel (130) is pivoted to the fully closed position (as shown in FIGS. 1, 10D, 11A-11B). Slot (133) is dimensioned to slidably receive a portion of cutting member (164) as staple sled assembly (160) is driven through staple cartridge assembly (150) such that cutting member (164) may sever tissue captured between anvil surface (134) and staple deck (158) during exemplary use.

As seen best in FIG. 9, second portion (104) of instrument (100) of the present example further includes a staple height adjustment mechanism (136). Adjustment mechanism (136) is operatively coupled with anvil plate (134), for example via one or more camming features (not shown), and includes a pair of user-engageable projections (138). Adjustment mechanism (136) is selectively movable relative to anvil channel (130) between two or more longitudinal positions to raise or lower anvil plate (134) relative to anvil channel (130), and thereby adjust a gap distance (or "tissue gap") between anvil plate (134) and staple deck (158) when first and second instrument portions (102, 104) are coupled together in a fully closed position. A larger gap distance, and thus a greater staple height, may be provided for stapling tissues of greater thicknesses. Similarly, a smaller gap distance, and thus a smaller staple height, may be provided for stapling tissues of lesser thicknesses. It will be appreciated that staple height adjustment mechanism (136) is merely optional and may be omitted in other examples. In some versions of instrument (100), the anvil surface, shown in the form of anvil plate (134), may be fixed relative to anvil channel (130). For instance, the anvil surface may be formed integrally with anvil channel (130).

Surgical linear cutting stapler (100) may be further configured and operable in accordance with one or more teachings of U.S. Pat. No. 7,905,381, entitled "Surgical Stapling Instrument with Cutting Member Arrangement," issued Mar. 15, 2011; U.S. Pat. No. 7,954,686, entitled "Surgical Stapler with Apparatus for Adjusting Staple Height," issued Jun. 7, 2011; U.S. Pat. No. 8,348,129, entitled "Surgical Stapler Having A Closure Mechanism," issued Jan. 8, 2013; and U.S. Pat. No. 8,789,740, entitled "Linear Cutting and Stapling Device with Selectively Disengageable Cutting Member," issued Jul. 29, 2014. The disclosure of each of these references is incorporated by reference herein.

Figure 10A:
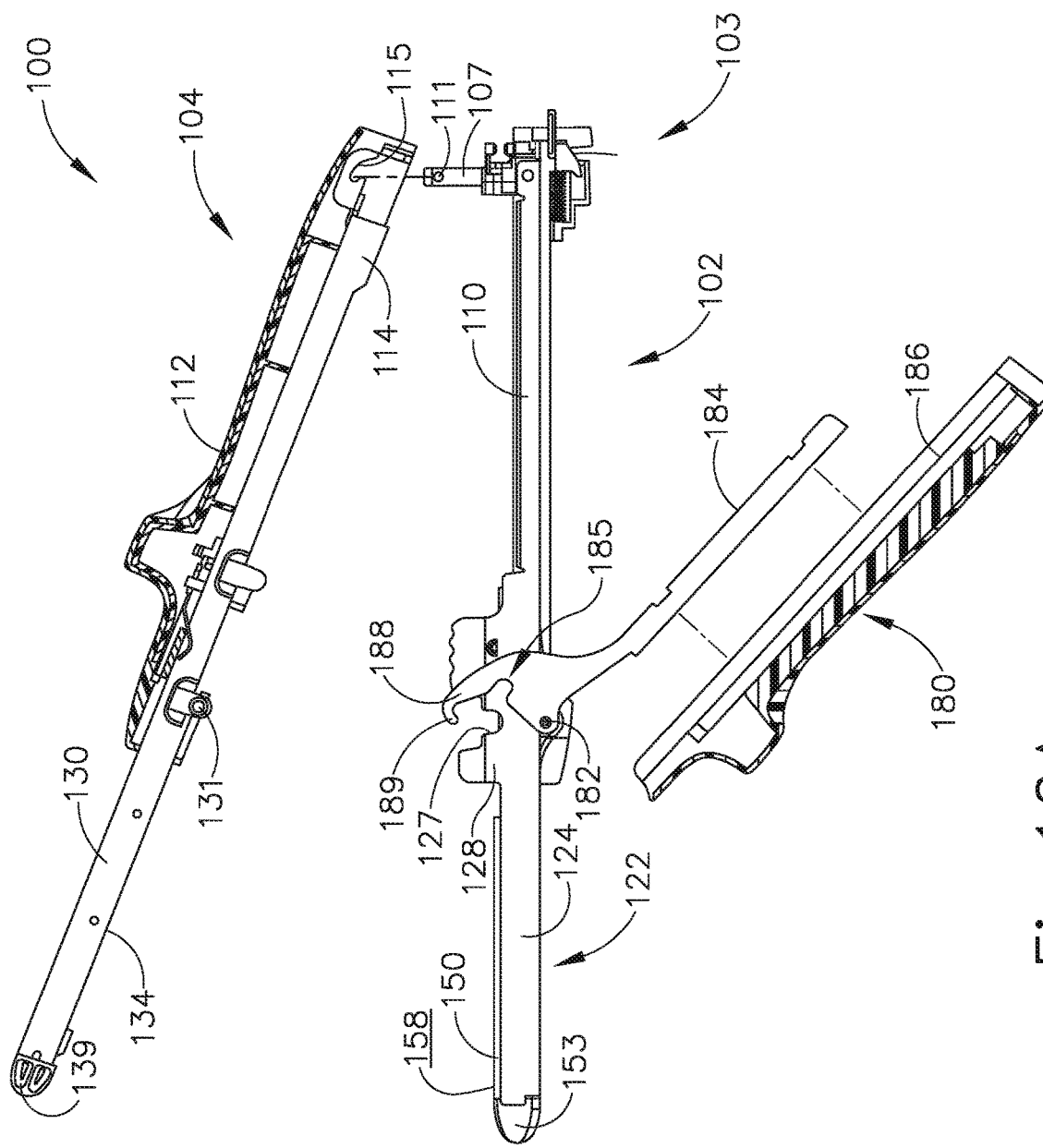
FIG. 10A depicts a cross-sectional side view of the surgical stapling instrument of FIG. 1, where a first portion and a second portion are decoupled from each other, and where an arm cover of the second portion is shown detached from the first portion for illustrative purposes.
Figure 10B:
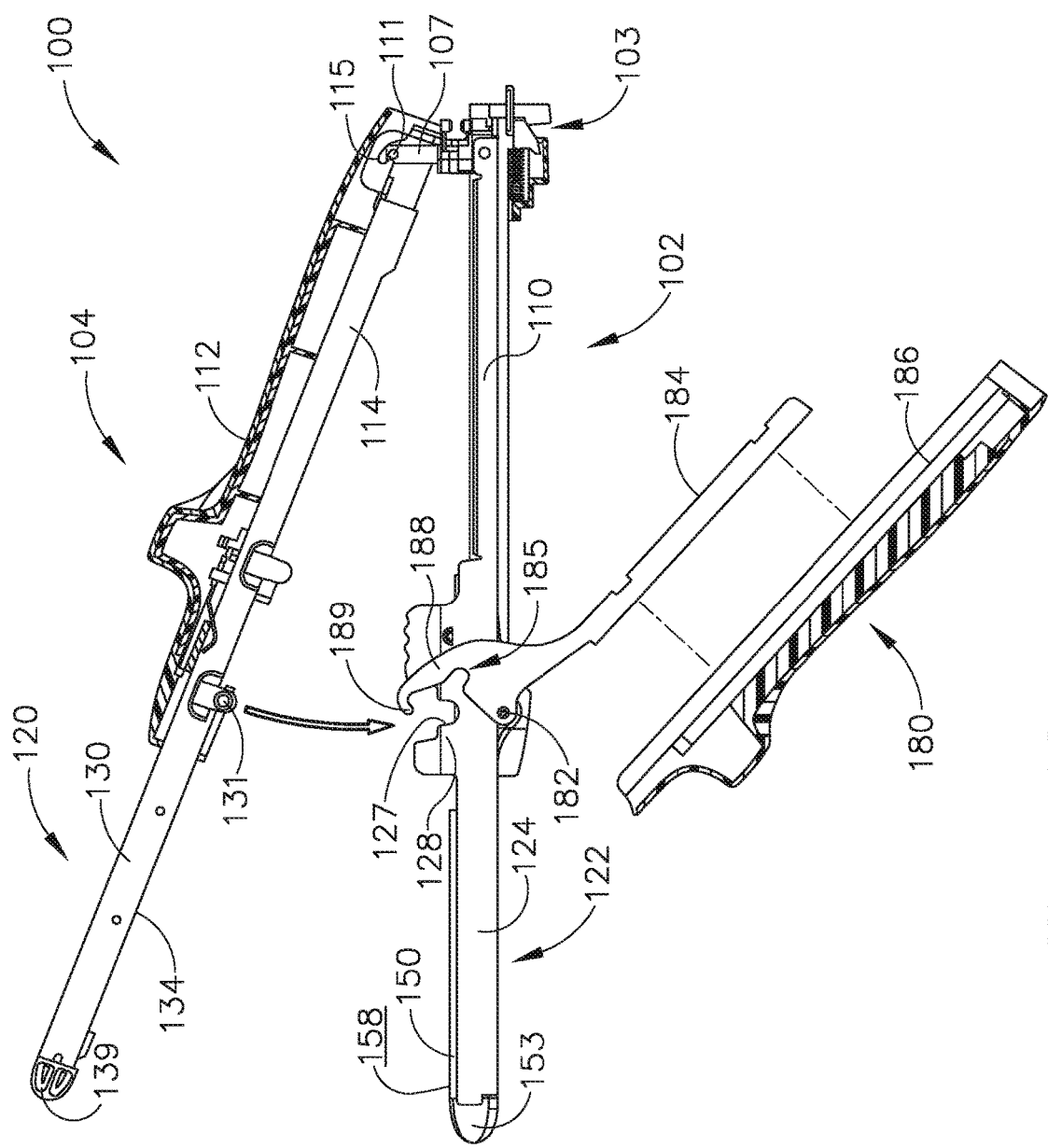
FIG. 10B depicts a cross-sectional side view of the surgical instrument of FIG. 1, where the first portion and the second portion of FIG. 10A are coupled with each other in an opened position.
Figure 10C:
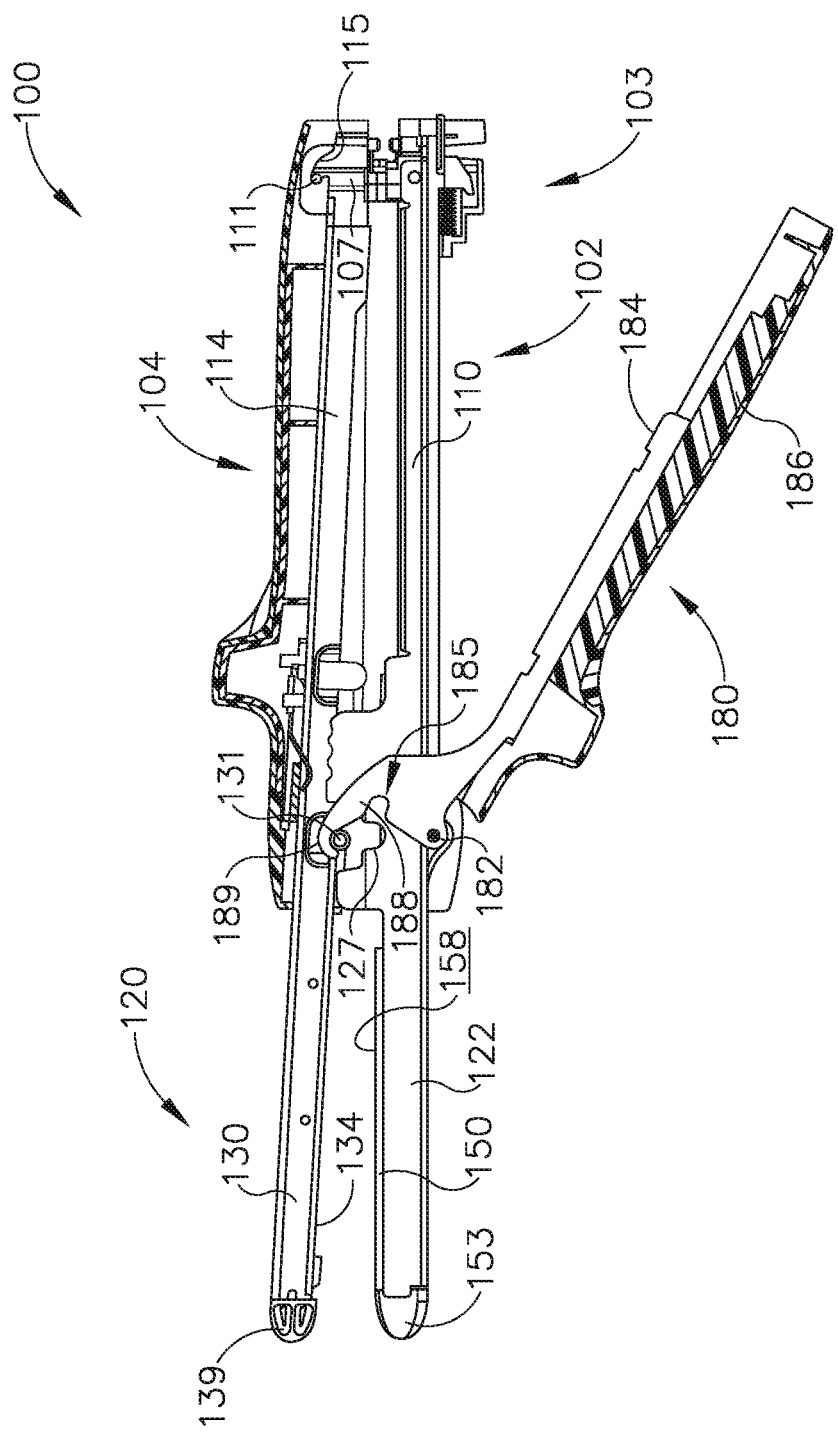
FIG. 10C depicts a cross-sectional side view of the surgical instrument of FIG. 1, where the first portion and the second portion of FIG. 10A are coupled with each other in a partially closed position.
Figure 10D:
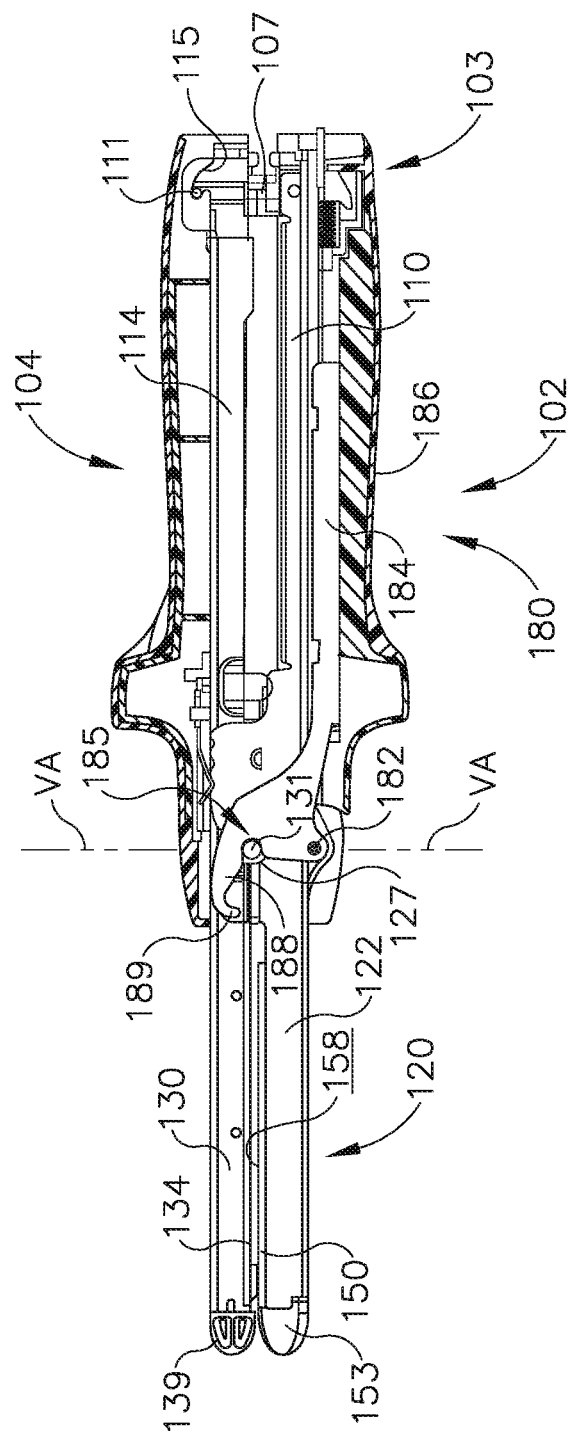
FIG. 10D depicts a cross-sectional side view of the surgical instrument of FIG. 1, where the first portion and the second portion of FIG. 10A are coupled with each other in a fully closed position.
Figure 11A:
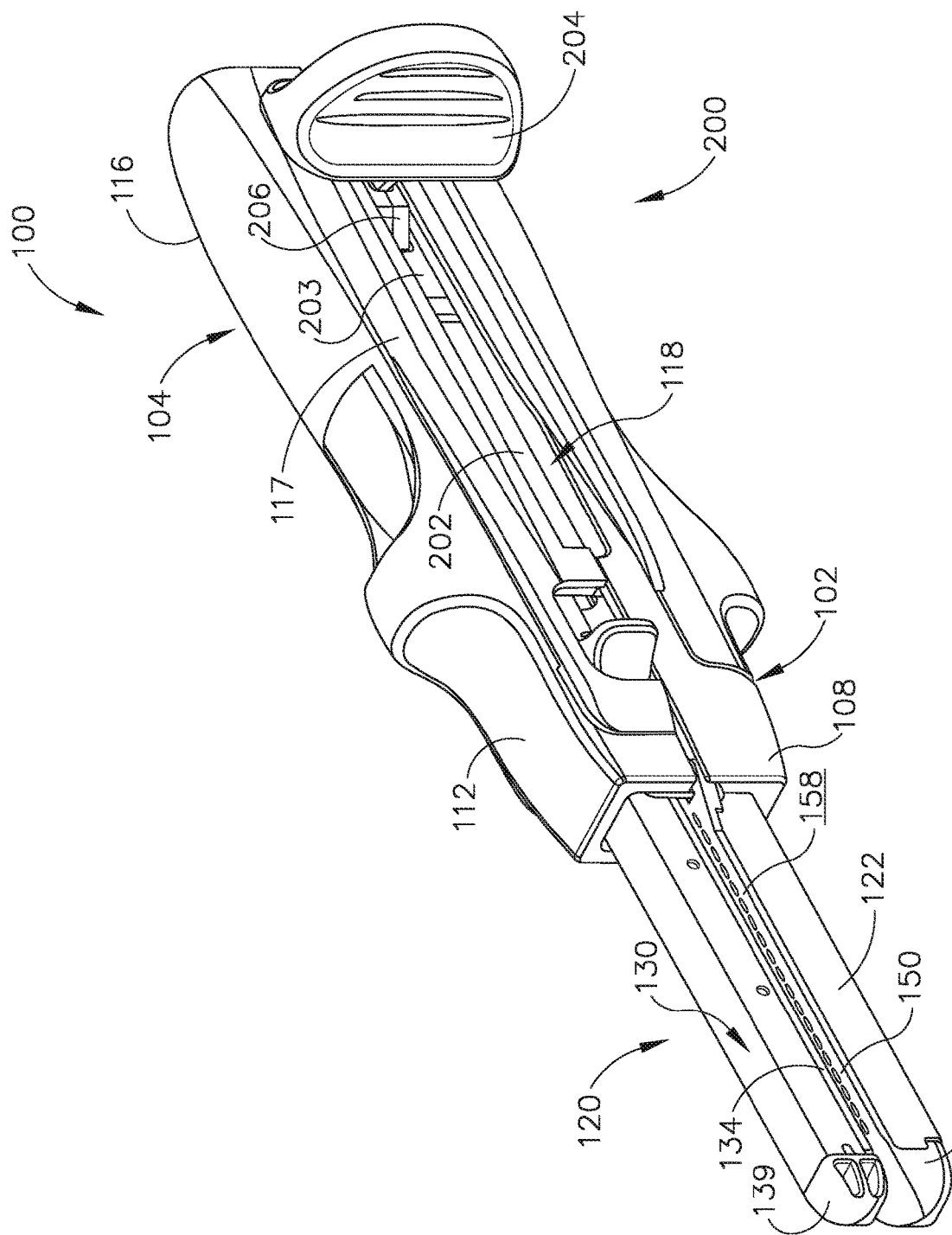
FIG. 11A depicts a perspective view of the surgical instrument of FIG. 1, where a firing assembly is in a pre-fired position.
Figure 11B:
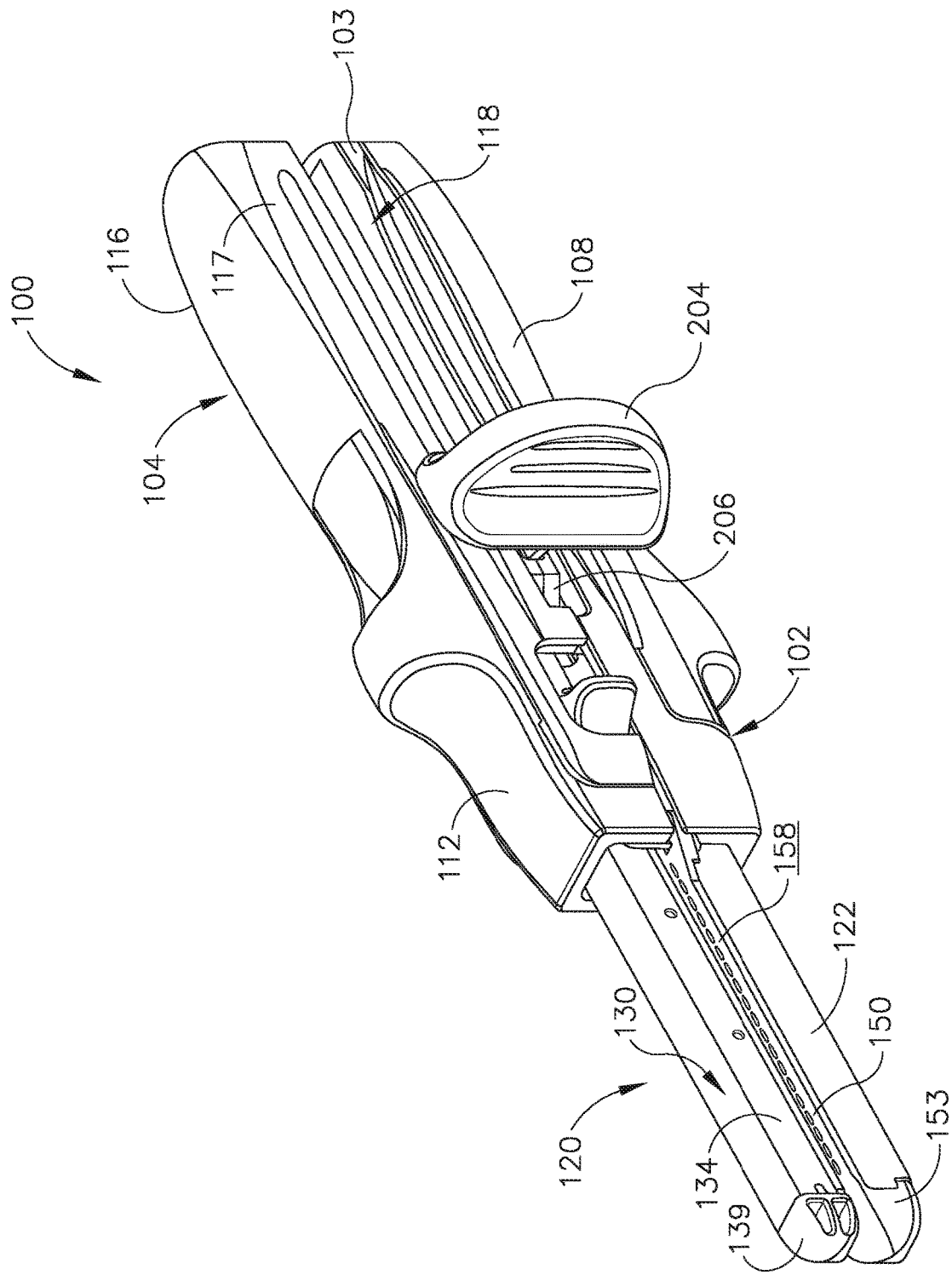
FIG. 11B depicts a perspective view of the surgical instrument of FIG. 1, where the firing assembly of FIG. 11A is in a fired position.

FIGS. 10A-11B show an exemplary use of instrument (100). In particular, FIGS. 10A-10D show an exemplary coupling of first portion (102) with second portion (104), and pivoting first portion (102) and second portion (104) such that end effector (120) transitions from an open position (FIG. 10B), to a partially closed position (FIG. 10C), and finally to a fully closed position (FIG. 10D). FIGS. 11A-11B show an exemplary firing of instrument (100) when end effector (120) is in a fully closed position.

FIG. 10A shows first portion (102) completely detached from second portion (204). Additionally, staple cartridge assembly (150) is suitably attached to staple cartridge channel (122) in accordance with the description above. At this point during a procedure, such as during a gastrointestinal anastomosis, an operator may desire to place lumens of tissue over and past distal noses (139, 153) of second portion (104) and cartridge assembly (150), respectively, such that lumens of tissue are suitably associated with both anvil plate (134) and cartridge assembly (150). At this point, an operator may align grooves (115) of second portion (104) with corresponding lateral projections (111) of first portion (102) in preparation of initially pivotally coupling first portion (102) with second portion (104).

Next, as shown in FIG. 10B, an operator may insert lateral projections (111) into corresponding grooves (115) such that first portion (102) and second portion (104) are pivotally coupled, but end effector (120) is in an open position. First portion (102) and second portion (104) may pivot relative to each other about the axis defined by lateral projections (111). At this point, latching lever (180) is not in contact with any portion of second portion (104). Additionally, latching lever (180) is in an open position such that proximal extending arm (184) is pivoted away from first proximal frame (110).

Next, as shown in FIG. 10C, an operator may initially pivot anvil channel (130) and anvil plate (134) toward cartridge channel (122) and staple cartridge assembly (150), and partially pivot latching lever (180) such that hooks (189) initially contact latch projections (131). At this point, end effector (120) is in the partially closed position. As best shown between FIGS. 10C-10D, after hooks (189) initially contact latch projections (131), an operator may further rotate proximal extending arm (184) toward first proximal frame (110), causing distal latch body (188) to drive latch projections (131) along the surfaces of distal latch body (188) toward latch cutouts (185). As latch projections (131) are driven toward latch cutouts (185), anvil channel (130) and anvil plate (134) rotate further toward cartridge channel (122) and staple cartridge assembly (150) such that end effector (120) is in the closed position. Additionally, latch projections (131) are also driven toward recesses (127) of staple cartridge channel (122) such that each latch projection (131) is encompassed by a combination of the respective latch cutout (185) and recess (127), effectively latching end effector (120) into the closed position. Latch cutouts (185) and recesses (127) may be dimensioned to interface with latch projections (131) while end effector (120) is in the fully closed position such that latch projections (131) and pivot pin (182) extend along a vertical axis (VA) that is substantially perpendicular with the longitudinal axis of instrument (100). This may provide a mechanical advantage for an enhanced closure force during suitable use.

FIGS. 11A-11B show an exemplary firing of instrument (100) with end effector (120) in the fully closed position. As best seen in FIG. 11A, an operator may pivot actuator (204) to either side (116, 117) of instrument (100). In the present example, actuator (204) has been pivoted to second side (117) of instrument (100). Next, operator may push actuator (204) distally toward end effector (120) within slot (118), such that actuating beam (202) and sled (160) are fired, thereby stapling and severing tissue captured between stapling deck (158) and anvil plate (134) in accordance with the description above. Once instrument (100) has been fired, an operator may pull actuator (204) proximally back to the position shown in FIG. 11A, then rotate actuator (204) back to the position shown in FIG. 1, therefore completing a firing stroke. An operator may then pivot latching lever (180) such that proximally extending arm (184) is pivoted away from first proximal frame (110) in order to open end effector (120) from the fully closed position to the partially closed position. An operator may further pivot latching lever (180) such that distal latch body (188) no longer captures latch projections (131). Then an operator may decouple first portion (102) and second portion (104) from each other and replace staple cartridge assembly (150), if desired.

II. Exemplary Linear Cutting Stapler with Duel Sided Firing Levers

As mentioned above, an actuator (204) may be pivotably coupled to distal end (201) of actuating beam (202) via pivot arm (206). Therefore, an operator may pivot actuator (204) from the fully proximal position as shown in FIG. 1 to either first side (116) or second side (117) in order to actuate firing assembly (100). However, since pivot arm (206) connects actuator (204) to actuating beam (202), the force from pushing actuator (204) to translate actuating beam (202) may cause pivot arm (206) to break or snap due to the forces imparted on pivot arm (206) during firing. Because actuator (204) is laterally offset from actuating beam (202) during firing, a bending moment within pivot arm (206) may be induced, which may also lead to breaking or snapping pivot arm (206) during firing. Because pivot arm (206) is dimensioned to pivot to either lateral side (116, 117) of instrument, it may difficult to structurally reinforce pivot arm (206) on one lateral side (116, 117) to prevent breaking during exemplary use, as this may disrupt pivot arm (206) from rotating toward the opposite lateral side (116, 117) of instrument (100).

Alternatively, as mentioned above, actuator (204) may be strictly limited to one lateral side (116, 117) of instrument, thereby allowing the arm or beam that connects actuator (204) to actuating beam (202) to be structurally reinforced. However, having a single actuator (204) limited to one side of instrument may limit the amount of ways an operator may grasp first portion (102) and second portion (104) of instrument (100) during firing. For example, in some instances an operator may find it more convenient to actuate firing assembly (200) on lateral side (116, 117) of instrument (100) opposite to which actuator (204) is slidable coupled.

Alternatively, as also mentioned above, instrument (100) may have two actuators (204) attached to proximal end (201) of actuating beam (202), where one actuator (204) in located on first side (116), and the other actuator (204) is located on second side (117). However, since both actuators (204) are attached to proximal end (201) of actuating beam (202), when an operator grasps one actuator (204) with a first hand to fire actuating beam (202), the actuator (204) located on the other lateral side of instrument (100) also travels with actuating beam (202). Translation of the non-grasped actuator (204) may interfere with the grasp an operator has on first and second portions (102, 104) of instrument (100) with a second hand. For instance, the non-grasped actuator (204) may slide against the palm of the second hand that controls first and second portions (102, 104).

Therefore, it may be desirable to provide a firing assembly having a pair of actuators, where one actuator is accessible from an opposite side of a linear stapler as compared to the other actuator. In addition, it may be desirable during exemplary use such that where the actuator not grasped remains in the proximal position while the grasped actuator drives the actuating beam in accordance with the description above. Alternatively, it may be desirable to provide a firing assembly having a pair of actuators, where one actuator is accessible from each lateral side and both actuators are coupled to the actuating beam. However, unlike the example described above, it may be further desirable such that the non-grasped actuator extends laterally inward toward the actuating beam to provide an unobtrusive profile as to not interfere with the grasping of first and second portions (102, 104) during exemplary use.

Figure 12:
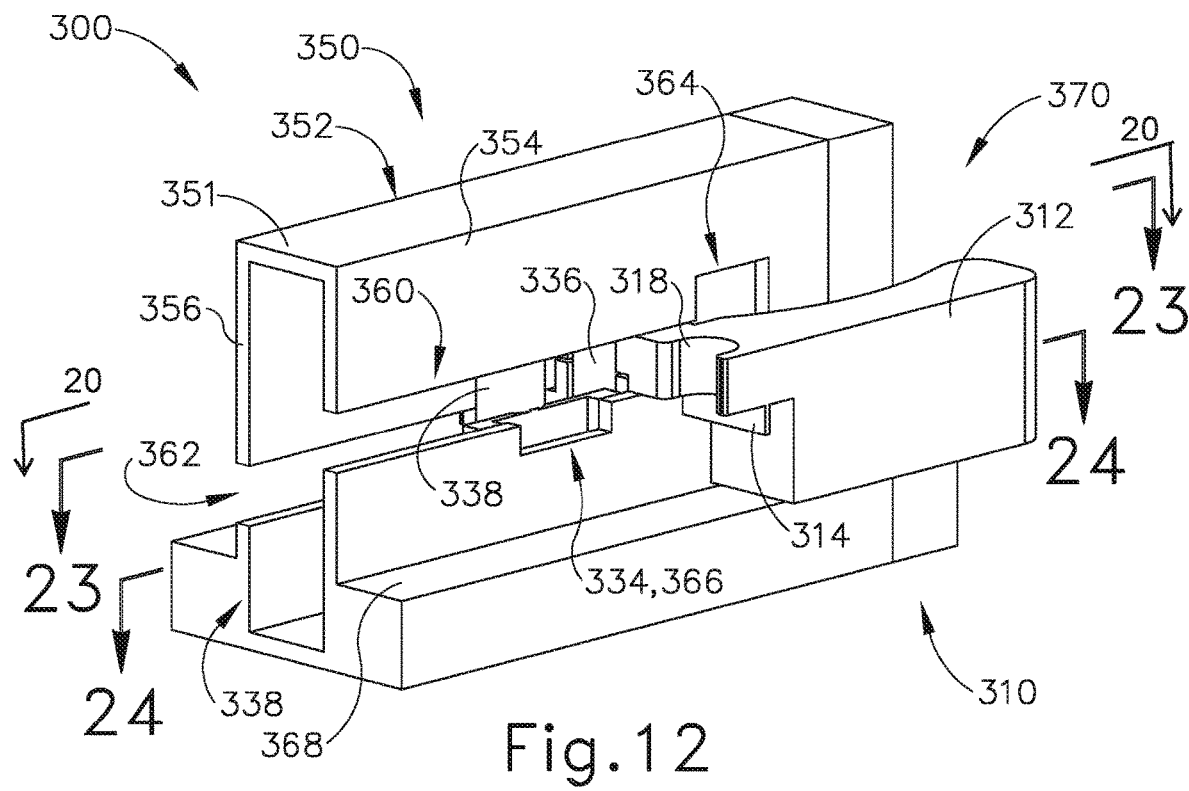
FIG. 12 depicts a perspective view of an alternative proximal end of an alternative first portion and a firing assembly that may be readily incorporated into the surgical stapling instrument of FIG. 1.
Figure 13:
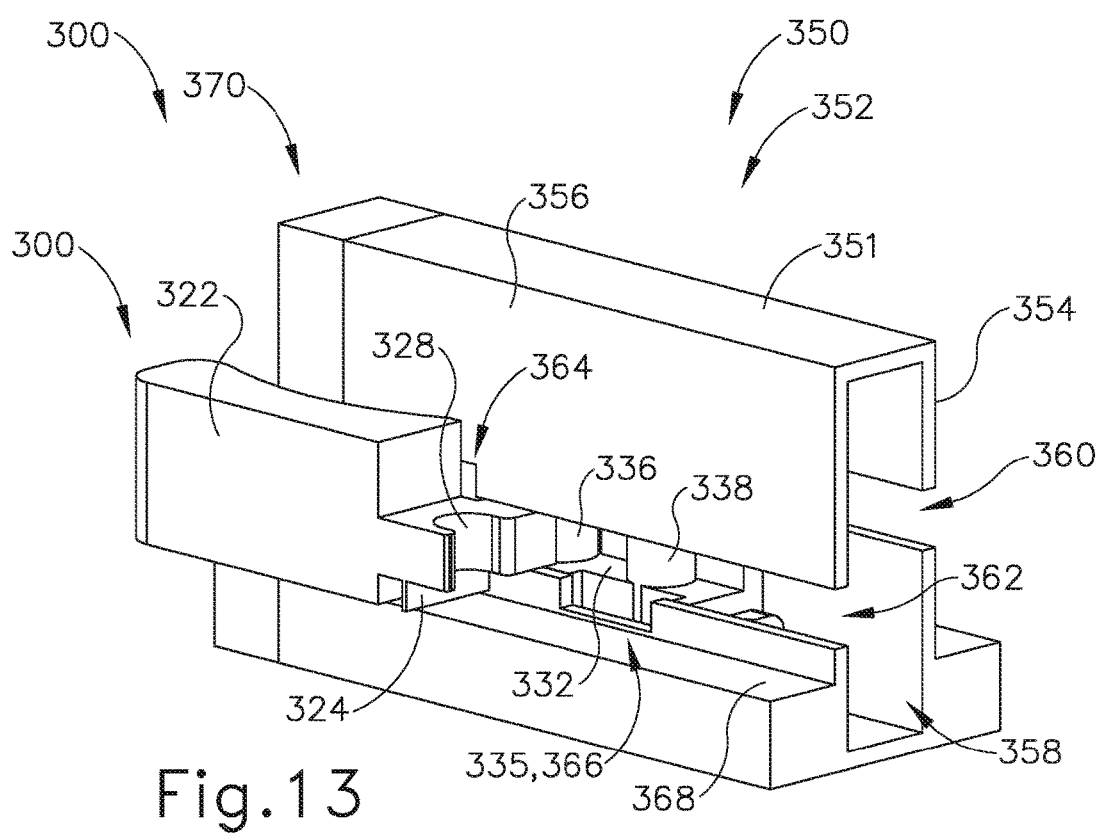
FIG. 13 depicts another perspective view of the firing assembly of FIG. 12.
Figure 14:
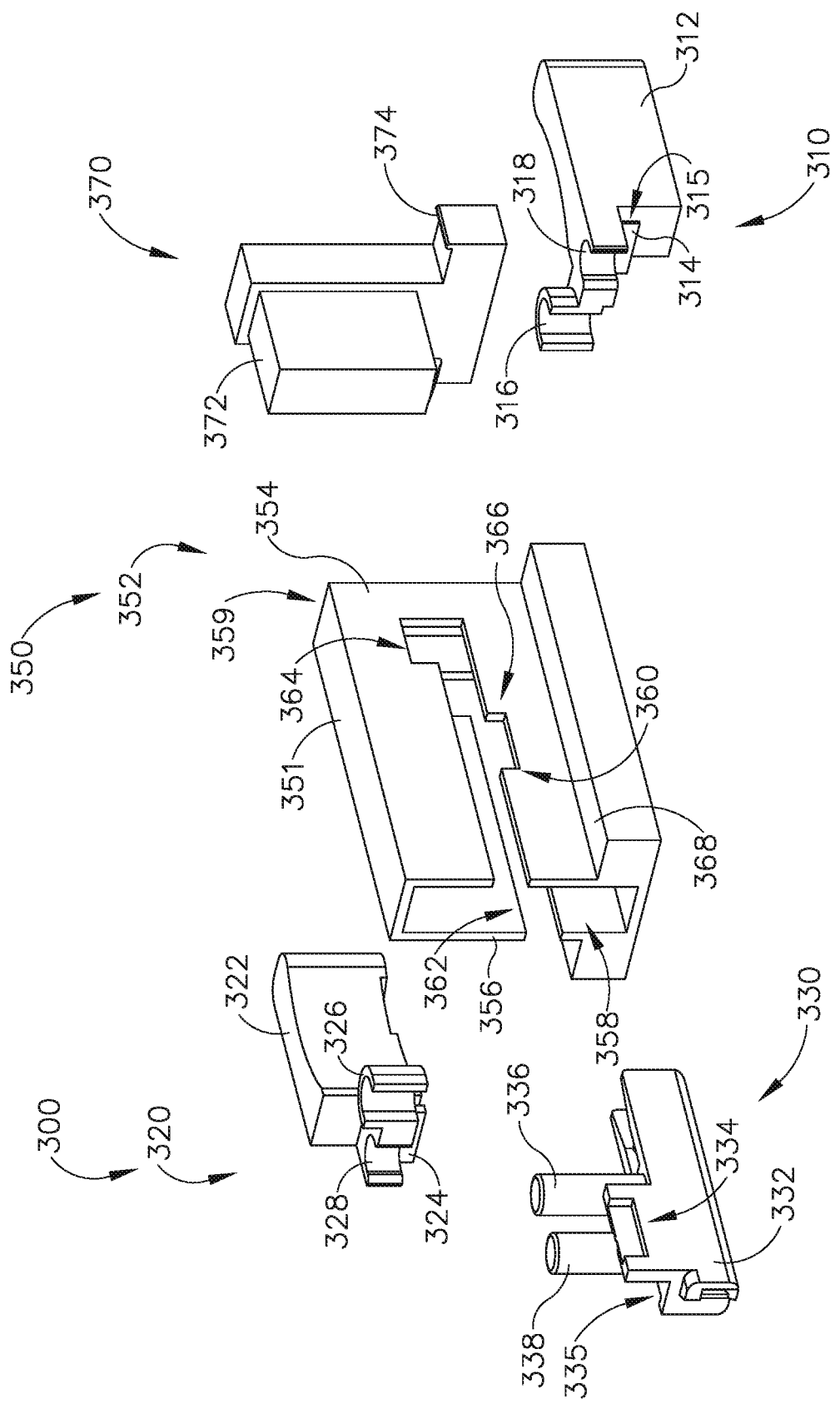
FIG. 14 depicts an exploded perspective view of the firing assembly of FIG. 12.

A. Exemplary Firing Assembly Having Duel Sided Firing Levers with Independent Actuation FIGS. 12-14 show an exemplary alternative firing assembly (300) and an exemplary alternative proximal end (352) of an exemplary alternative first portion (350) that may be readily incorporated into instrument (100) in replacement of firing assembly (200), and proximal end (103) of first portion (102) described above, respectively. First portion (350) includes a first proximal frame (351) and a proximal cap (370), while firing assembly includes a first lever (310) (i.e. actuator or firing knob), a second lever (320) (i.e. actuator or firing knob), and an actuating beam (330) extending distally into staple sled assembly (342).

Figure 23A:
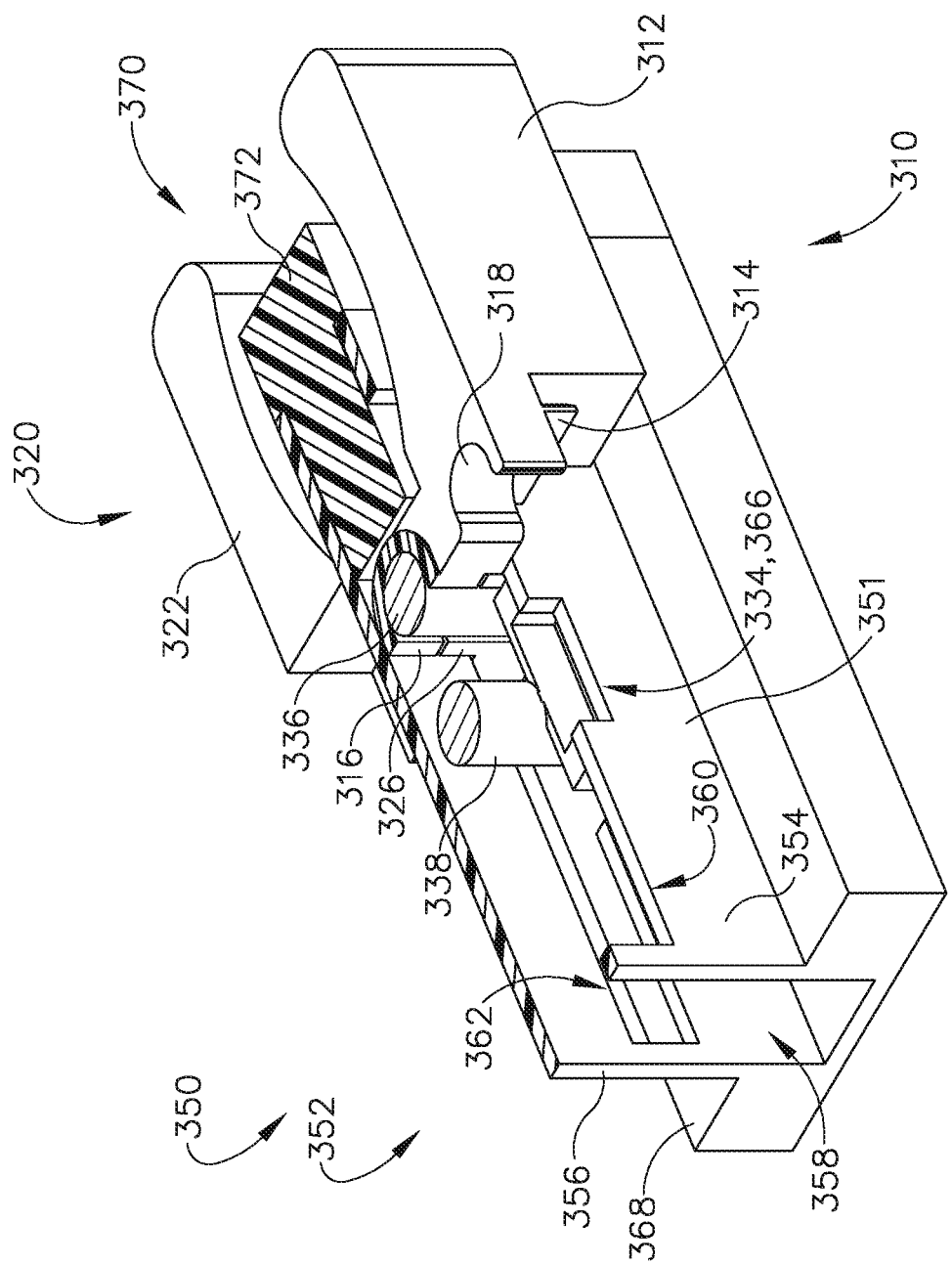
FIG. 23A depicts a cross-sectional perspective view of the firing assembly of FIG. 12, taken along line 23-23 of FIG. 12, where the first lever of FIG. 17 and the second lever of FIG. 19 are both in a locked, pre-fired, configuration.
Figure 24A:
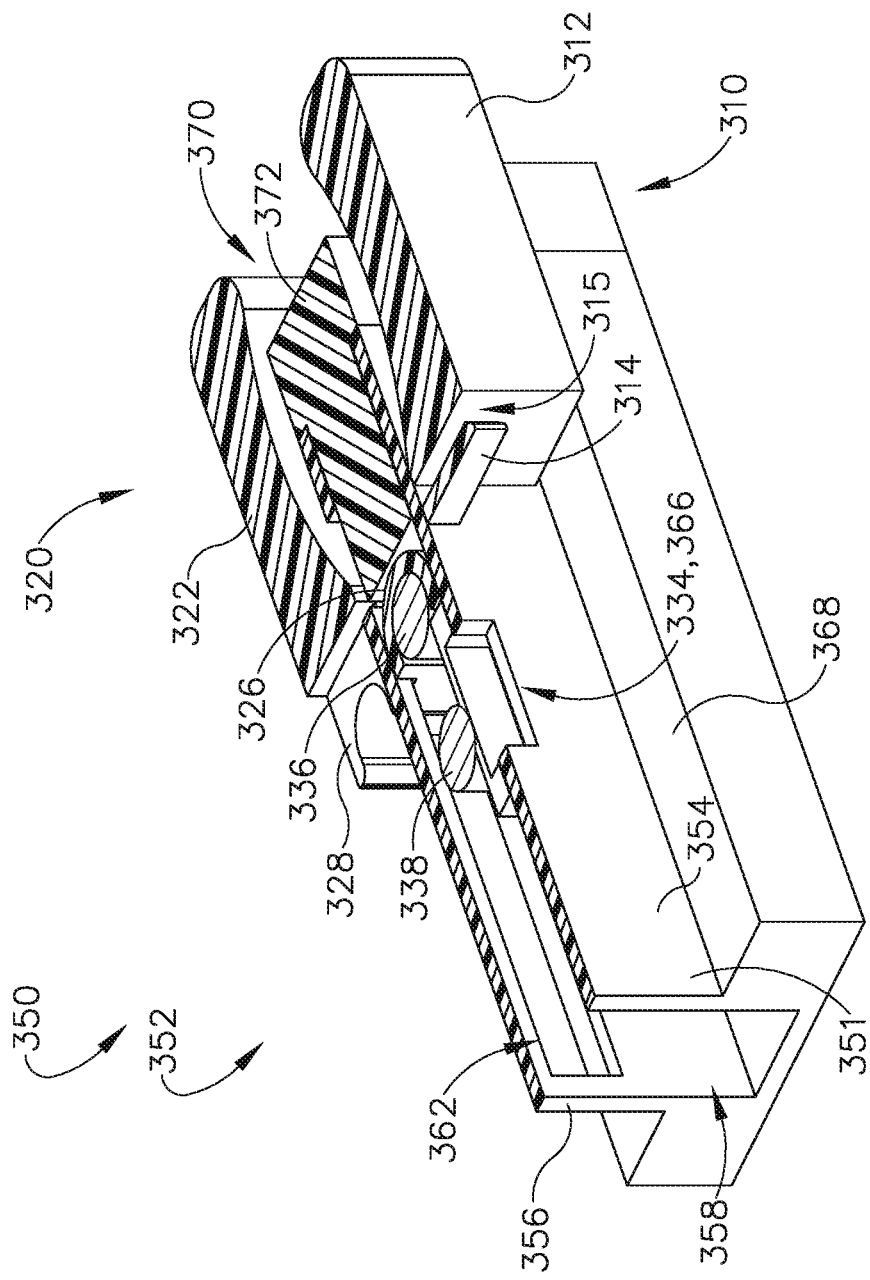
FIG. 24A depicts a cross-sectional perspective view of the firing assembly of FIG. 12, taken along line 24-24 of FIG. 12, where the first lever of FIG. 17 and the second lever of FIG. 19 are both in the locked, pre-fired, configuration.
Figure 24B:
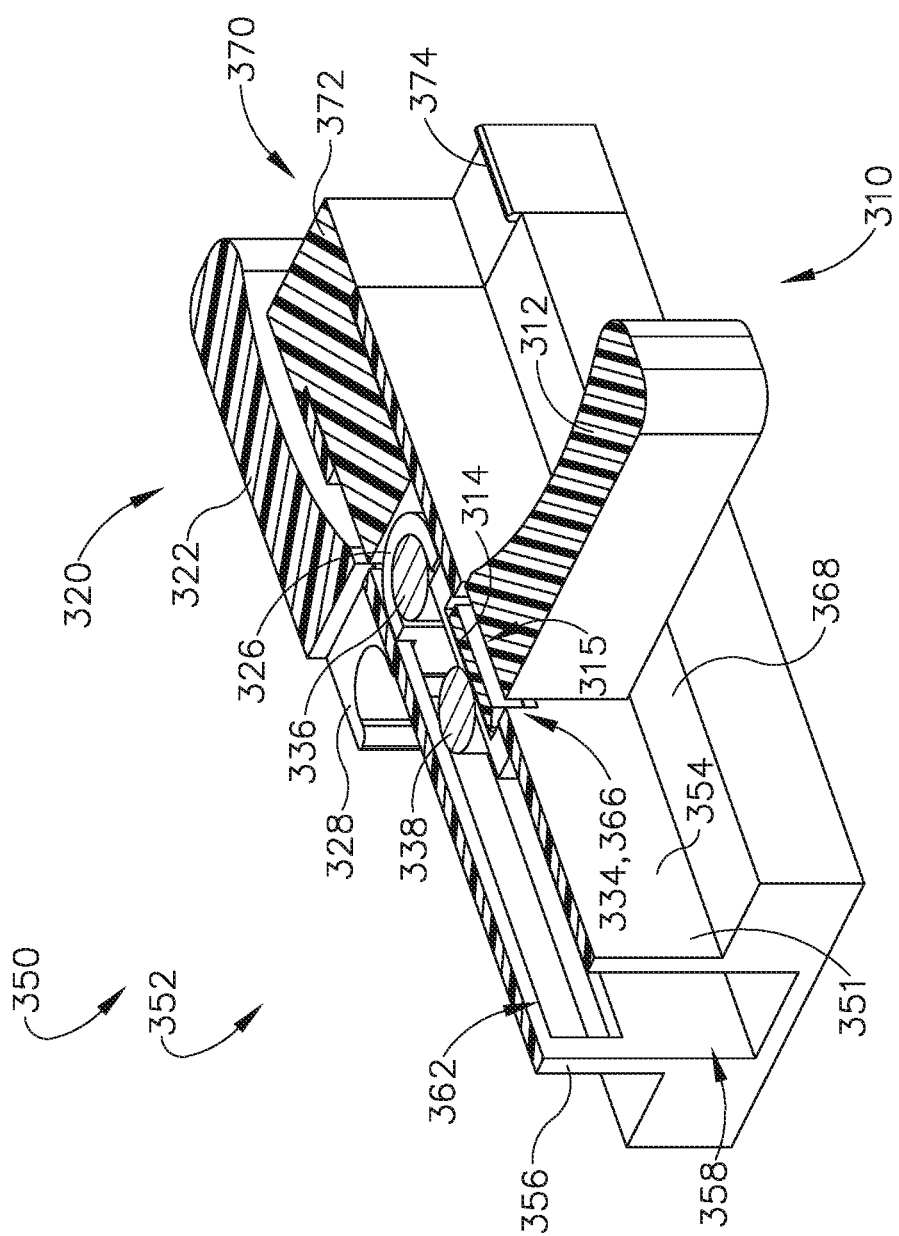
FIG. 24B depicts a cross-sectional perspective view of the firing assembly of FIG. 12, taken along line 24-24 of FIG. 12, where the first lever of FIG. 17 is in a laterally extended, pre-fired, configuration.

As will be described in greater detail below, first lever (310) and second lever (320) are associated with opposite sides of first portion (350). First lever (310) and second lever (320) are configured to pivot from a fully proximal position (as shown in FIGS. 12-13, 23A, and 24A), to a pre-fired lateral position (as shown in FIGS. 23B and 24B) independently of each other. Additionally, as will be described in greater detail below, first lever (310) and second lever (320) are configured to longitudinally actuate between the pre-fired lateral position and a fired position, independently of one another, in order to drive actuating beam (330) and staple sled assembly (342) to staple and sever tissue captured between end effector (120) in accordance with the description above. Additionally, the lever (310, 320) not pivoted to the lateral position may remain in the fully proximal position during firing of actuating beam (330). Levers (310, 320) may also be structurally reinforced to help prevent snapping of lever (310, 320). Therefore, an operator may use either lever (310, 320) to fire actuating beam (330) while the other lever (310, 320) remains in an unobstructed position.

Proximal cap (370) includes a stop block (374) and locking protrusions (374). As will be described in greater detail below, stop block (374) is dimensioned to prevent distal translation of first and second lever (310, 320) such that levers (310, 320) may not decouple with first portion (350) after firing assembly (300) and first portion (350) are properly assembled. As will also be described in greater detail below, locking protrusions (374) are configured to interact with selected portions of levers (310, 320) to prevent unwanted or accidental movement of levers (310, 320) relative to first portion (350) when levers (310, 320) are in a fully proximal position.

First proximal frame (351) may be substantially similar to first proximal frame (110) described above, with differences elaborated below. Therefore, first proximal frame (351) may extend distally into staple cartridge channel (122) in order to define an elongate cartridge channel member of unitary construction. Similar to first proximal frame (110) described above, first proximal frame (351) defines a channel (358) that slidably houses an actuating beam (330) of firing assembly (300). Channel (358) terminates at an open proximal end (359) dimensioned to receive stop block (372) of proximal cap (370). While not shown, proximal end (352) may include one or more lateral pins in order to initially pivotably couple with second portion (104).

First proximal frame (351) includes a platform (368), a first side (354), and a second side (356). Platform (368) is dimensioned to slidably support first and second levers (310, 320) while firing assembly (300) is actuated. However, it should be understood that platform (368) is entirely optional. While instrument (100) has first portion (102) and second portion (103) cooperatively define slot (118) that accommodates translation of actuator (204), first side (354) of first proximal frame (351) defines an upper slot (360) and second side (356) of first proximal frame (351) defines a lower slot (362). Upper slot (360) and lower slot (362) slidably house first lever (310) and second lever (320), respectively. It should be understood that upper slot (360) and lower slot (362) extend distally along first proximal frame (351) a suitable distance such that actuating beam (330) may complete a firing stroke in accordance with the description above.

As will be described in greater detail below, upper slot (360) and lower slot (362) are vertically offset from one another such that first lever (310) and second lever (320) may suitably couple with actuating beam (330). Both upper slot (360) and lower slot (362) define an initial coupling window (364) and a pivot lock window (366). As will also be described in greater detail below, initial coupling window (364) is dimensioned to receive a portion of levers (310, 320) in order to initially pivotably and slidably couple levers (310, 320) with actuating beam (330). Pivot lock window (366) is dimensioned to receive a portion of levers (310, 320) when levers (310, 320) are pivoted into the laterally extended position.

Figure 15:
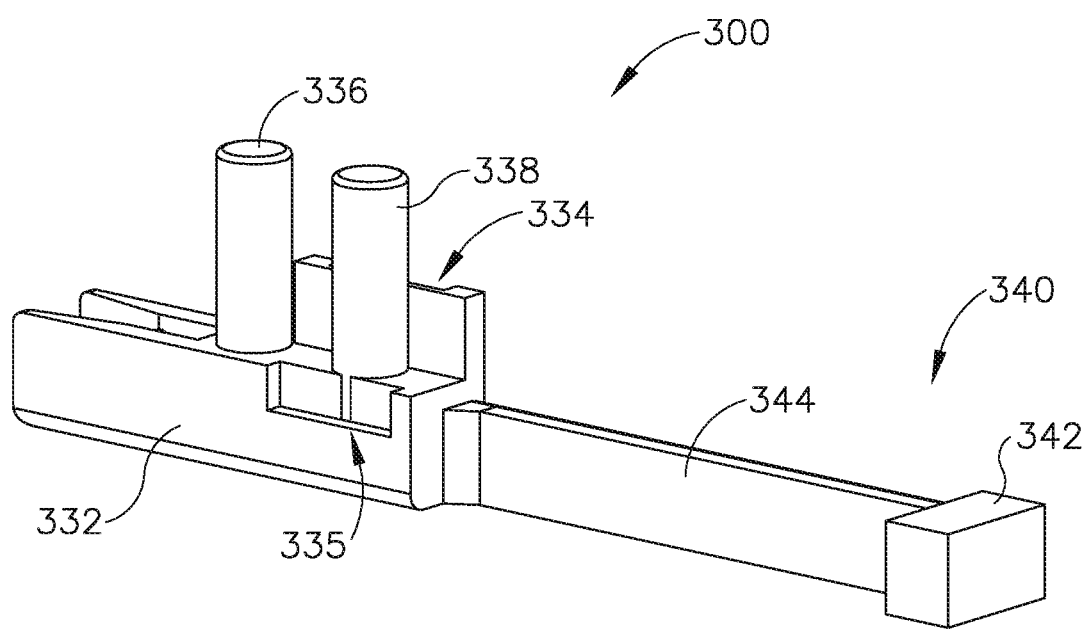
FIG. 15 depicts a perspective view of a proximal body of the actuating beam of the firing assembly of FIG. 12.
Figure 16:
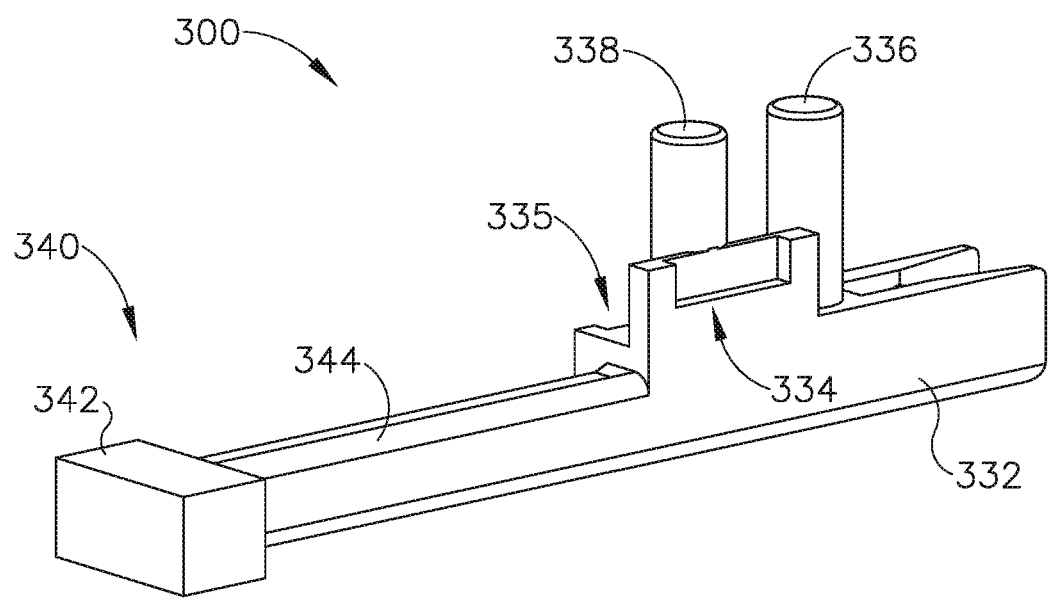
FIG. 16 depicts another perspective view of the proximal body of the actuating beam of FIG. 15.

FIGS. 15-16 show exemplary proximal end of actuating beam (330). Actuating beam (330) is slidably housed within channel (358) of first portion (350). It should be understood that actuating beam (330) and staple sled assembly (342) may be substantially similar to actuating beam (202) and staple sled assembly (160) described above, respectively, with differences elaborated below. Therefore, actuating beam (330) includes a beam portion (344) that extends distally through channel (358) of first portion (250) toward a distal end (340) that is substantially similar to distal end (201) of actuating beam (202) described above. Therefore, distal end (340) of actuating beam (330) may be configured to selectively couple with staple sled assembly (342). Alternatively, distal end of actuating beam (330) may include staple assembly (342). It should be understood that in some figures, beam portion (344) and staple sled assembly (342) are omitted for purposes of clarity.\

As best seen in FIGS. 15-16, proximal end of actuating beam (330) includes a proximal body (332) defining first and second rotational locking pockets (334, 335), a pivoting post (336) extending away from body (332), and a grasping post (338) extending away from body (332). First and second rotational locking pockets (334, 335) are dimensioned to align with pivot lock windows (366) of upper slot (360) and lower slot (362), respectively, when actuating beam (330) is in a pre-fired, proximal position (as shown in FIGS. 12-13, 20A-20D, 23A-23B, and 24A-24B). First and second rotational locking pockets (334, 335) are vertically offset from each other in order to receive respective portions of levers (310, 320) which are also vertically offset from each other when suitably associated with pivoting post (336). As will also be described in greater detail below, pivot lock windows (366) and locking pockets (334, 335) are dimensioned to receive a portion of levers (310, 320), respectively, when levers (310, 320) are pivoted to the lateral, pre-fired, position. Once either lever (310, 320) is in the lateral position and actuated distally, that lever (310, 320) is confined to the laterally extended position relative to actuating beam (330) and first proximal frame (310). As will also be described in greater detail below, pivoting post (336) and grasping post (338) are configured to interact with levers (310, 320) such that levers (310, 320) may drive actuating beam (330) through a firing stroke in accordance with the description above.

Figure 17:
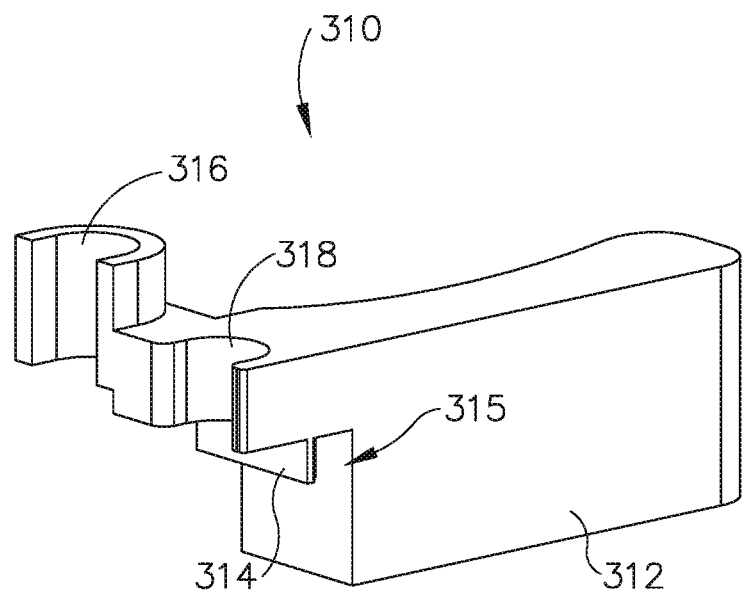
FIG. 17 depicts a perspective view of a first lever of the firing assembly of FIG. 12.
Figure 18:
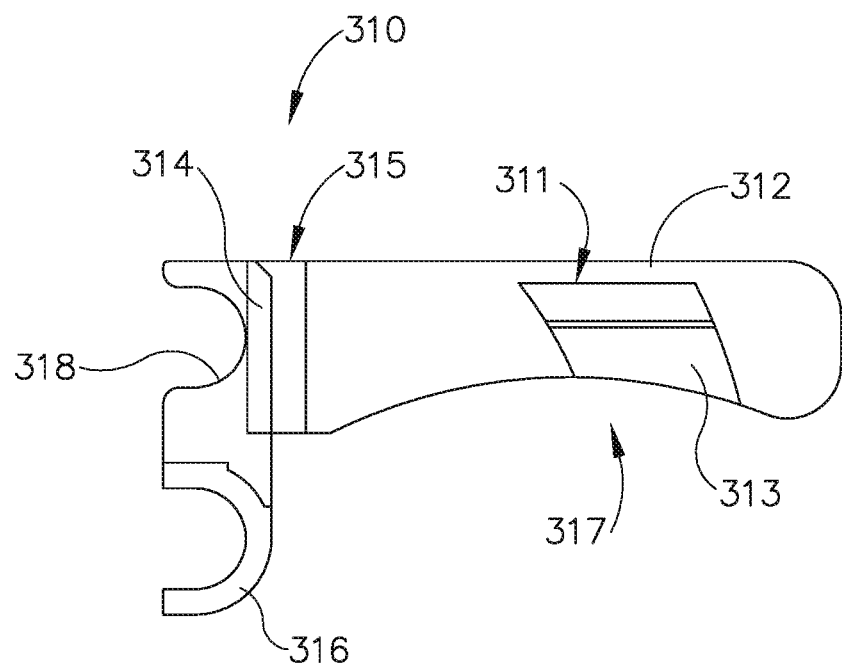
FIG. 18 depicts a bottom plan view of the first lever of FIG. 17.
Figure 19:
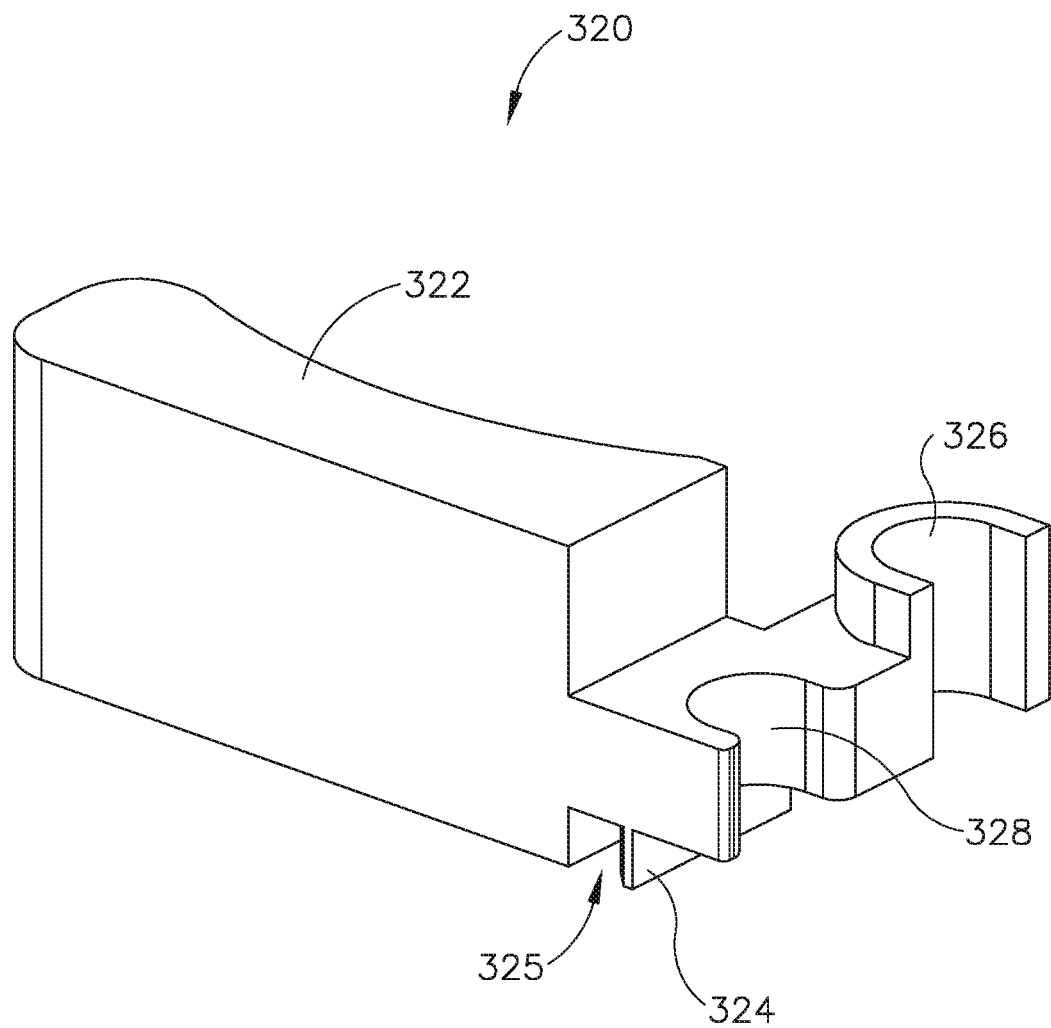
FIG. 19 depicts a perspective view of a second lever of the firing assembly of FIG. 12.

FIGS. 17-18 show first lever (310) while FIG. 19 shows second lever (320). First lever (310) is associated with first side (354) of first proximal frame (351) while second lever (320) is associated with second side (356) of first proximal frame (351). First lever (310) includes a grasping body (312), a rotational lock body (314), a pivoting half sleeve (316), and a firing half sleeve (318). Grasping body (312) of first lever (310) also includes a sloped surface (313) that partially defines a locking recess (311) and an open end (317), which are configured to interact with locking protrusion (374) to selectively lock lever (310) in the fully proximal position.

Pivoting half sleeve (316) is dimensioned to pivotably couple with pivot post (336) when actuating beam (330) is in the proximal position or when first lever (310) is driving actuating beam (330) through a firing stroke. Firing half sleeve (318) is dimensioned to grip grasping post (338) when first lever (310) is pivoted to the lateral position. Interaction between firing half sleeve (318) of first lever (310) and grasping post (338) of actuating beam (330) may provide additionally structure support that may help prevent lever (310) from snapping during exemplary use. Pivoting half sleeve (316) and firing half sleeve (318) are dimensioned for insertion within upper slot (360). While firing half sleeve (318) is dimensioned to pivot into and out of upper slot (360) during exemplary use, pivoting half sleeve (316) is not. When properly assembled, stop block (372) is longitudinally aligned with initial coupling windows (364) such that pivoting half sleeve (316) may not longitudinally align with initial coupling window (364). All other portions of upper slot (360) expect initially coupling window (364) are too small for pivoting half sleeve (316) to travel through. Therefore, when stop block (372) is properly assembled, first lever (310) is constrained within channel (358) due to upper slot (360) and pivoting half sleeve (316).

Figure 23C:
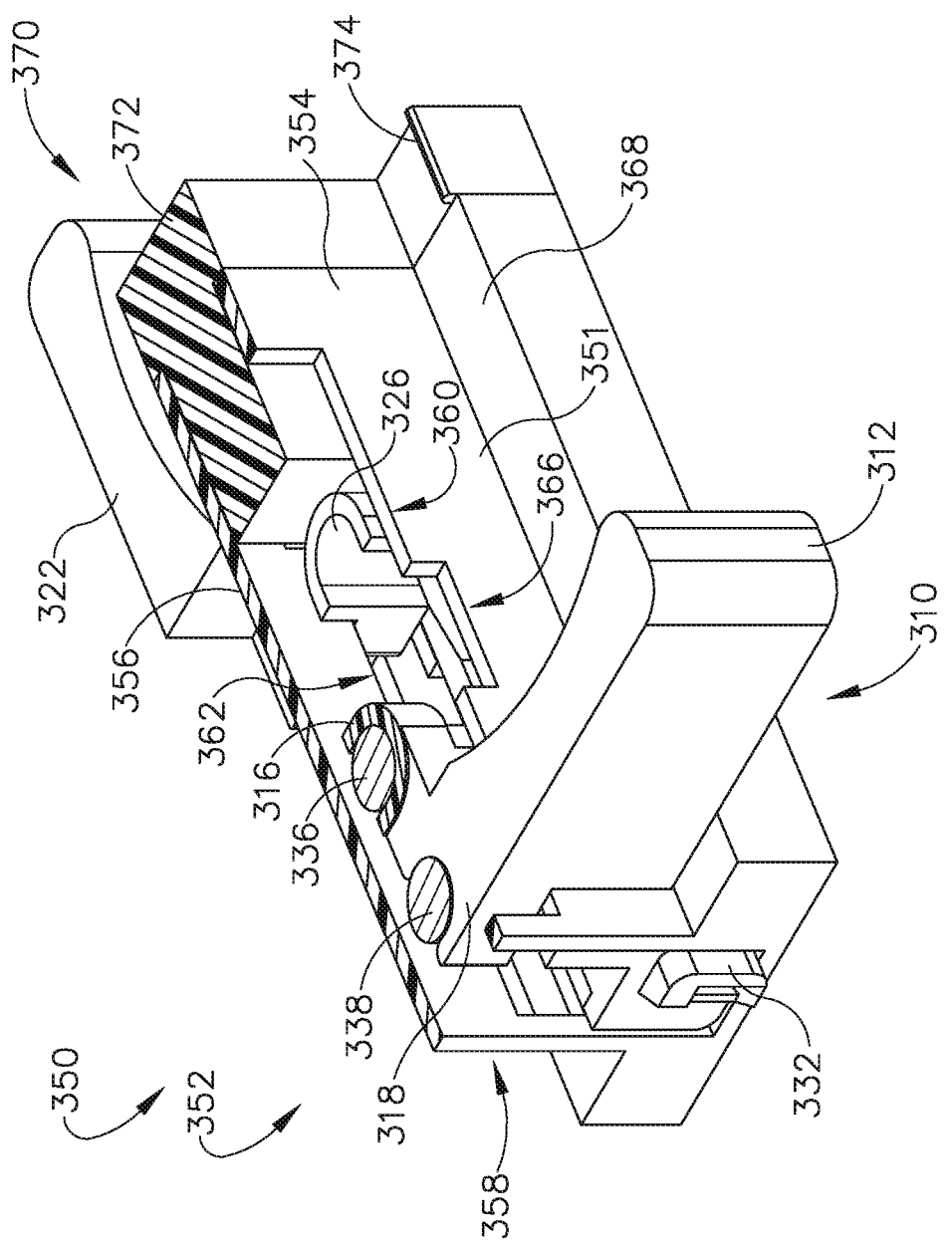
FIG. 23C depicts a cross-sectional perspective view of the firing assembly of FIG. 12, taken along line 23-23 of FIG. 12, where the first lever of FIG. 17 is in a laterally extended, fired, configuration.
Figure 24C:
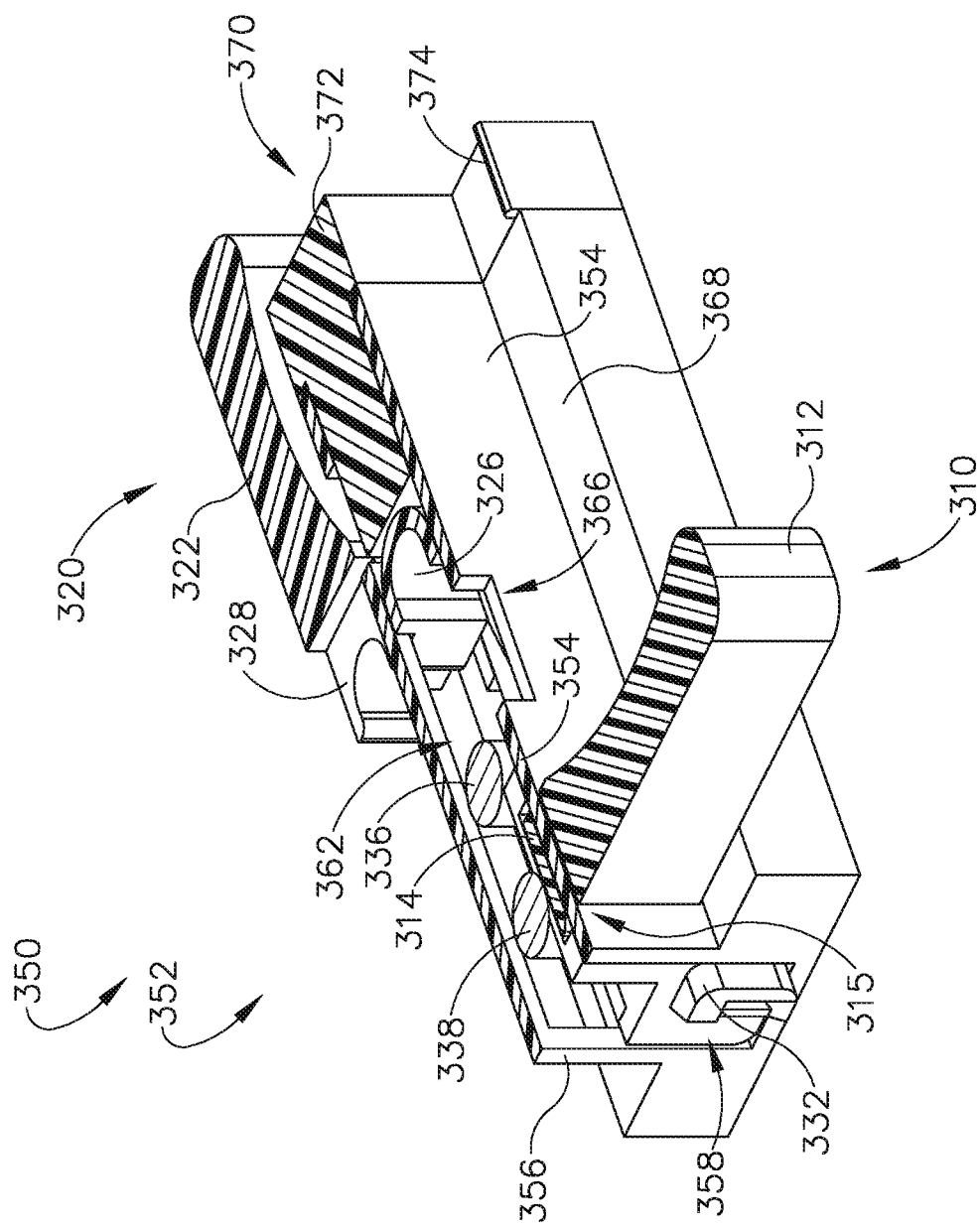
FIG. 24C depicts a cross-sectional perspective view of the firing assembly of FIG. 12, taken along line 24-24 of FIG. 12, where the first lever of FIG. 17 is in a laterally extended, fired, configuration.

Rotational lock body (314) and grasping body (312) cooperatively define a rotational lock channel (315). Rotational lock body (314) is dimensioned for insertion through pivot lock window (366) of upper slot (360) and into first rotational locking pocket (334) when first lever (310) is pivoted from the fully proximal position (as shown in FIGS. 23A and 24A), into the laterally extended, pre-fired, position (As shown in FIGS. 23B and 24B). Rotational lock body (314) is configured to rotationally lock lever (310) when lever (310) is in the laterally extended position and actuated distally (as shown in FIGS. 23C and 24C). In particular, rotational lock body (314) is confined between the interior surface of first side (354) and first rotational locking pocket (334). In other words, when lever (310) is actuated distally while in the laterally extended position, rotation lock channel (315) may receive first side (354) of first proximal frame (351). Therefore, lever (310) may not pivot about pivot post (336) when lever (310) is actuated distally in the laterally extended position. Additionally, when lever (310) is actuated distally while in the lateral extended position, rotational lock body (314) may also provide for structural support in order to help prevent lever (310) from snapping during exemplary use.

Second Lever (320) is substantially similar to first lever (310), with differences elaborated below. Therefore, second lever (320) includes a grasping body (322), a rotational lock body (324), a pivoting half sleeve (326), and a firing half sleeve (328); w which are substantially similar to grasping body (312), rotational lock body (314), pivoting half sleeve (316), and firing half sleeve (318) described above, respectively. Grasping body (322) of second lever (320) also includes a sloped surface (323) that partially defines a locking recess (321) and an open end (327), which are substantially similar to sloped surface (313), locking recess (311), and open end (317) described above, respectively. Additionally, grasping body (322) and rotational lock body (314) define a rotational lock channel (325) that is substantially similar to rotational lock channel (315) described above.

Second lever (320) is different from first lever (310) in that rotational lock body (324), pivoting half sleeve (326), and firing half sleeve (328) are located on a bottom portion of grasping body (322) in order to fit through lower slot (362); while rotational lock body (314), pivoting half sleeve (316), and firing half sleeve (318) are located on a top portion of grasping body (312) in order to fit through upper slot (360). This vertical misalignment allows both pivoting half sleeves (316, 326) to couple with pivoting post (336) when actuating beam (330) is in the proximal, pre-fired position. Additionally, the vertical misalignment allows for both first lever (310) and second lever (320) to simultaneously grasp pivoting post (336) and grasping post (338) if desired. Therefore, if desired, an operator may pivot both levers (310, 320) from the fully proximal position to the laterally extended position such that an operator may actuate both levers (310, 320) in order to drive firing assembly (300).

Figure 20B:
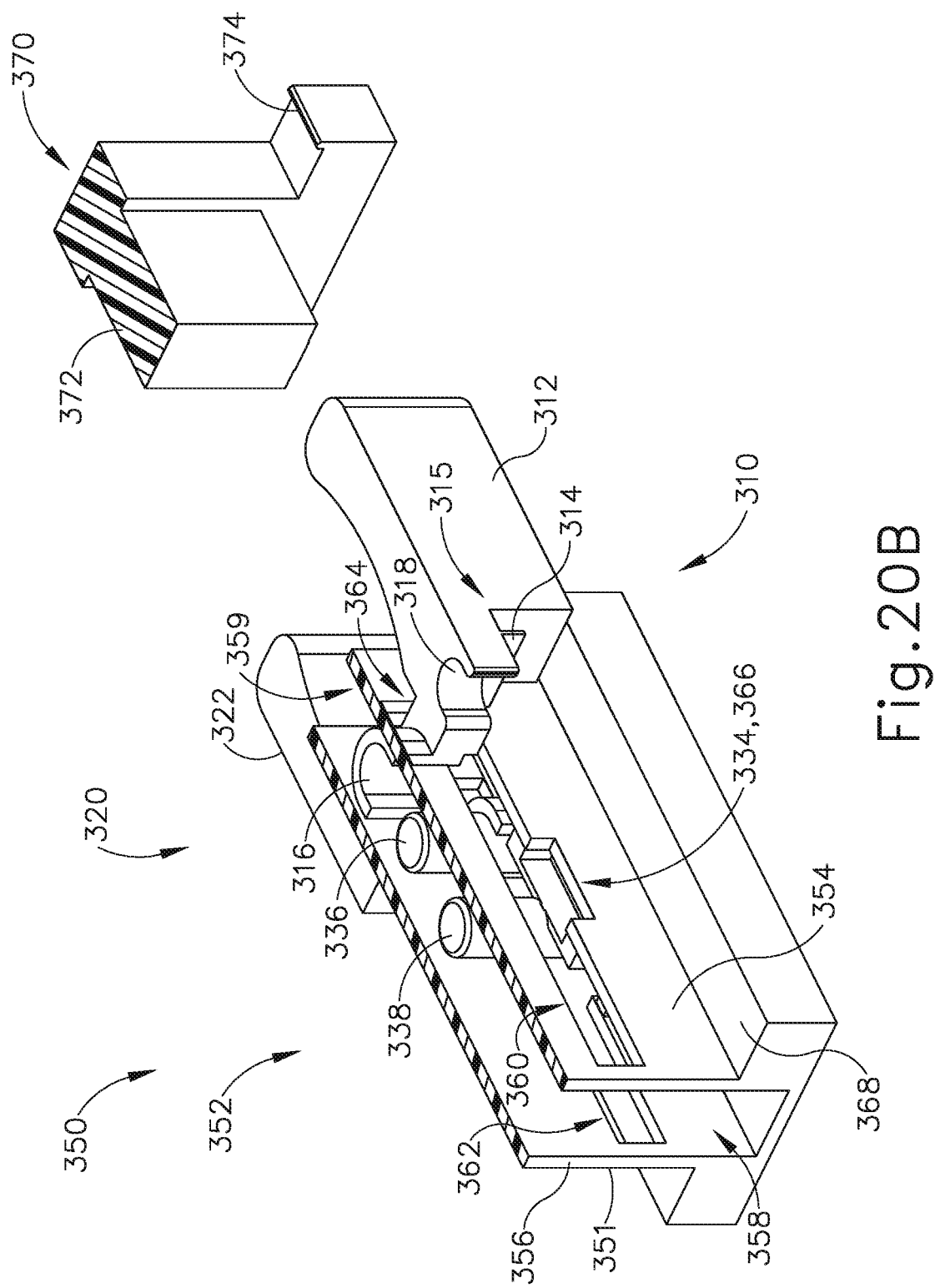
FIG. 20B depicts a cross-sectional perspective view of the firing assembly of FIG. 12 being assembled, taken along line 20-20 of FIG. 12, where the first lever of FIG. 17 is initially inserted within the proximal end of the first portion of FIG. 12, where the distal cap of FIG. 20A is decoupled from the first portion.
Figure 20C:
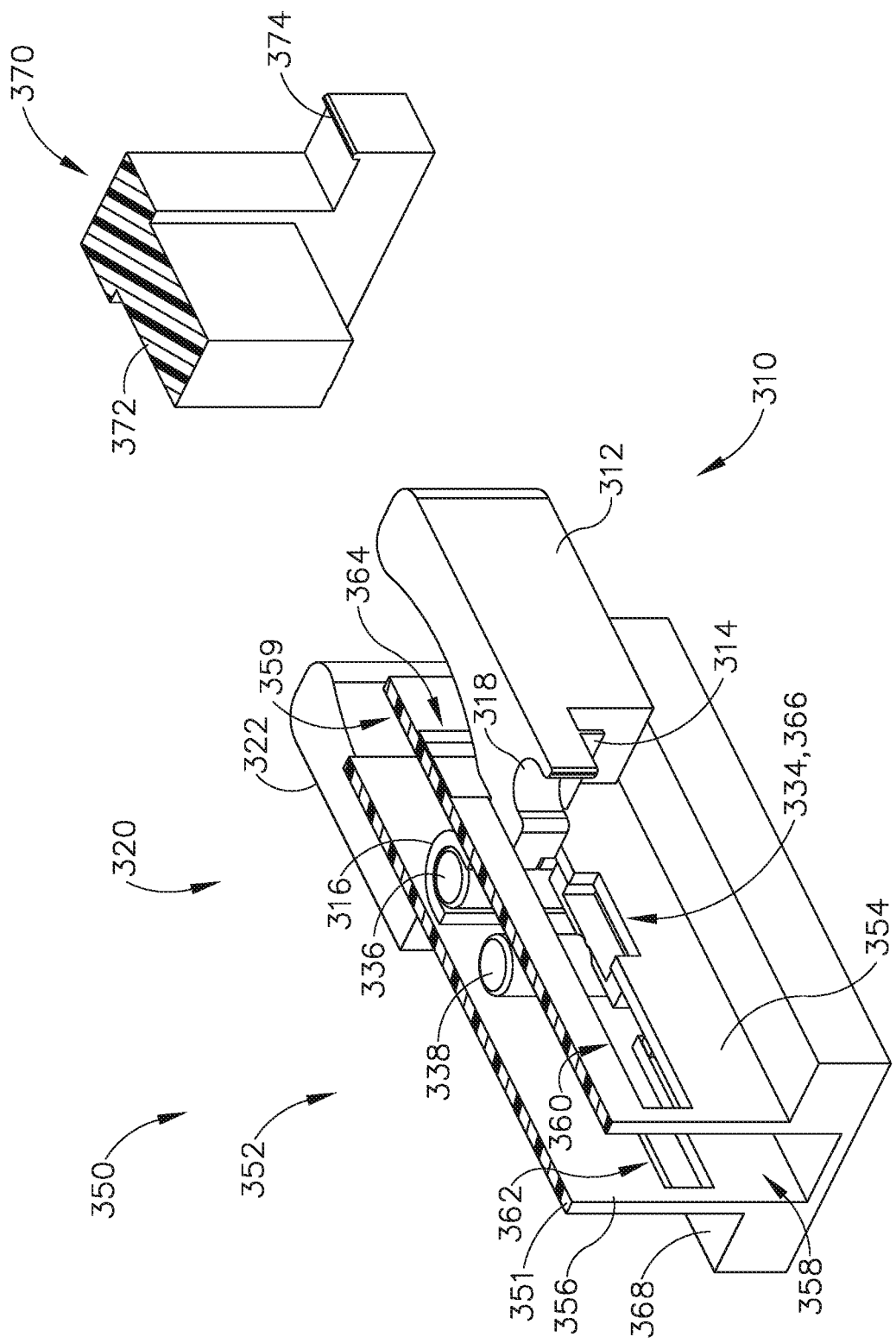
FIG. 20C depicts a cross-sectional perspective view of the firing assembly of FIG. 12 being assembled, taken along line 20-20 of FIG. 12, where the first lever of FIG. 17 is initially pivotably coupled with the proximal body of the actuating beam of FIG. 15, where the distal cap of FIG. 20A is decoupled from the first portion of FIG. 12.
Figure 20D:
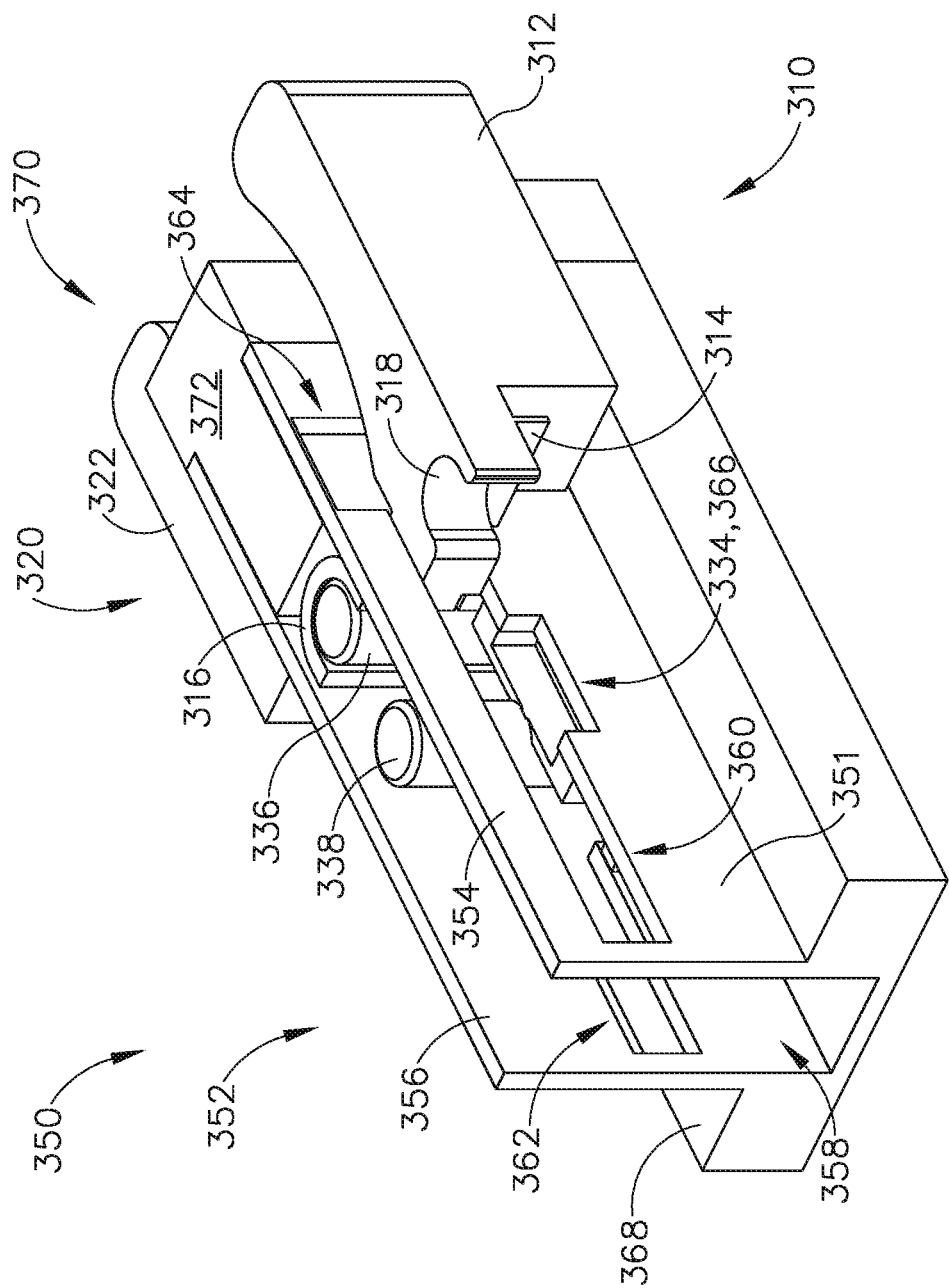
FIG. 20D depicts a cross-sectional perspective view of the firing assembly of FIG. 12 fully assembled, taken along line 20-20 of FIG. 12, where the first lever of FIG. 17 is pivotably coupled with the proximal body of the actuating beam of FIG. 15, where the distal cap of FIG. 20A is coupled with the first portion of FIG. 12.

FIGS. 20A-20D show an exemplary assembling process of attaching first lever (310) with first portion (350) and actuating beam (330). It should be understood that second lever (320) may be assembled with first portion (350) in a substantially similar manner, except second lever (320) is associated with lower slot (362) rather than upper slot (360). FIG. 20A shows proximal cap (370) and first lever (310) detached from first proximal frame (351). Pivoting half sleeve (316) is suitably aligned with initial coupling window (364). Because proximal cap (370) is detached from first proximal frame (351), stop block (372) does not current obstruct lateral access from initial couplings windows (364). Therefore, as best seen in FIG. 20B, pivoting half sleeve (316) may be inserted into channel (358) via initial coupling window (364). Next, as shown in FIG. 20C, lever (310) may be translating proximally such that pivoting half sleeve (316) pivotally couples with pivoting post (336) of actuating beam (330). Next, and shown in FIG. 20D, proximal cap (370) may be coupled with first proximal frame (351) by inserting stop block (372) within open proximal end (359) such that stop block (372) obstructs initial coupling window (364). At this point, first lever (310) is pivotably coupled with pivoting post (336) while slidable coupled with first proximal frame (351) via upper slot (360).

Figure 21:
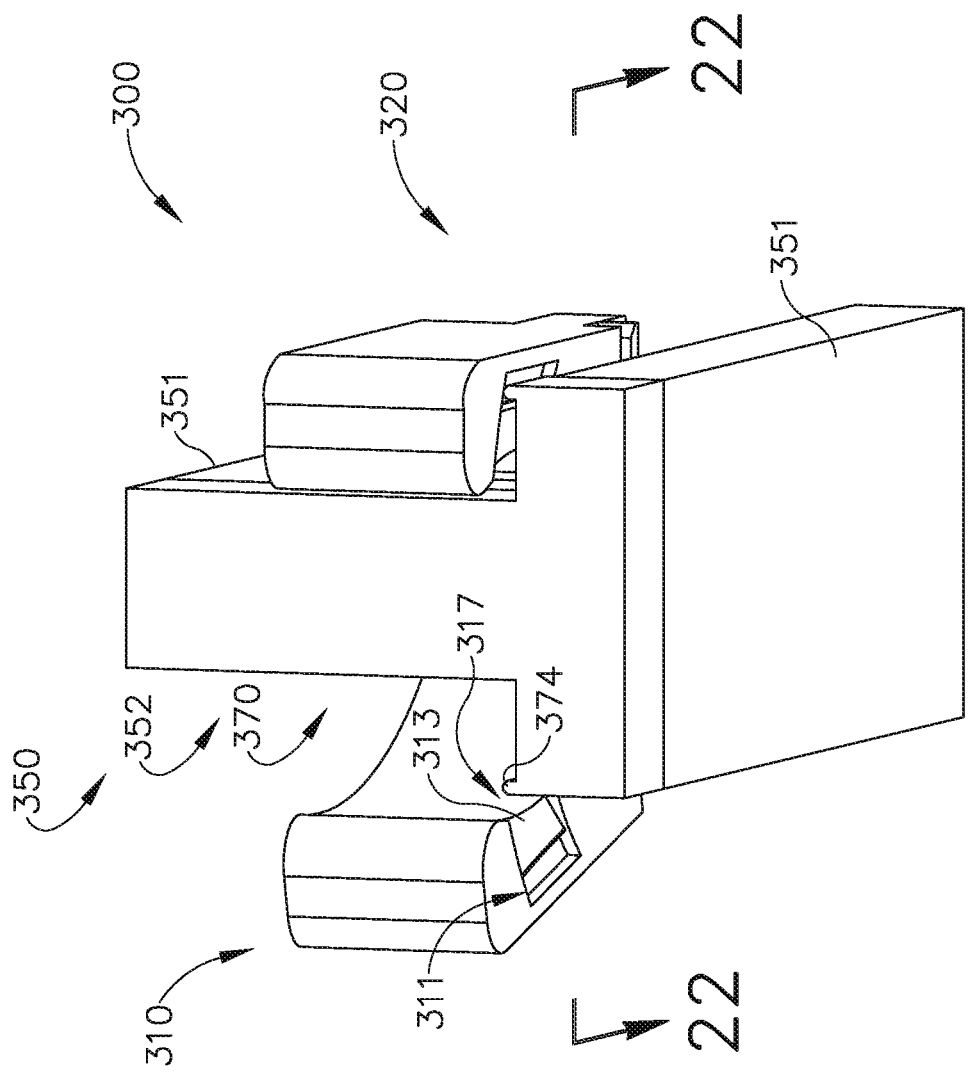
FIG. 21 depicts a perspective view of the firing assembly of FIG. 10, where the first lever of FIG. 17 is in an unlocked lateral position.

As mentioned above, first lever (310) includes sloped surface (313) partially defining locking recess (311) and open end (317); while second lever (320) includes sloped surface (323) partially defining locking recess (321) and open end (327). Locking recesses (311, 321), open ends (317, 327), and sloped surfaces (313, 323) are configured to interact with locking protrusion (374) to selectively lock levers (310, 320) in the fully proximal position to prevent levers (310, 320) from accidentally pivoting or actuating away from the fully proximal position during exemplary use. FIGS. 21-22B show an exemplary use of locking recess (311), sloped surface (313) and open end (317) to selectively lock first lever (310) in the fully proximal position. However, it should be understood that second lever (320) may operator in a substantially similar manner.

Figure 22A:
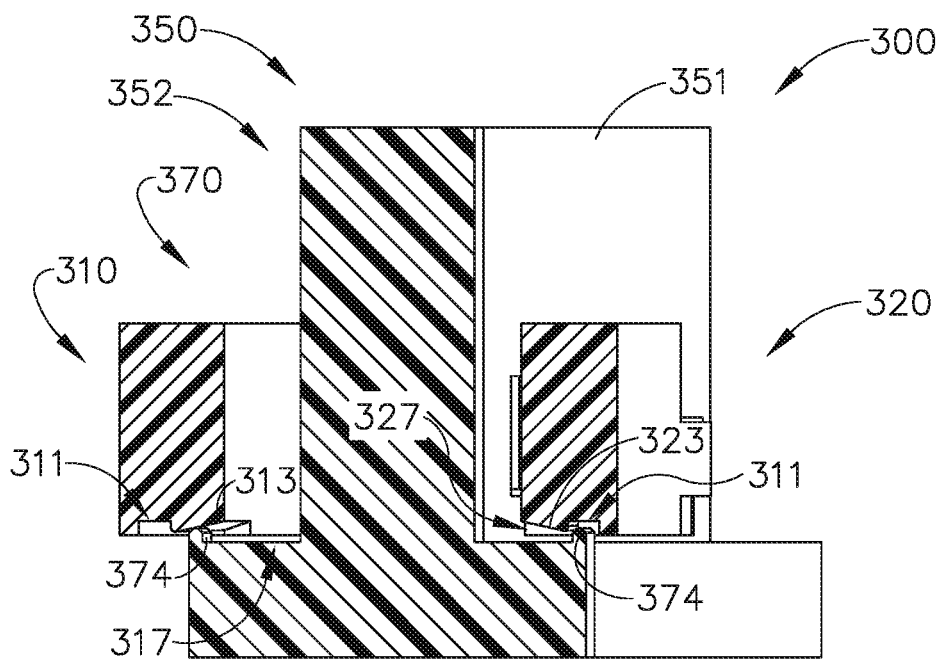
FIG. 22A depicts a cross-sectional perspective view of the firing assembly of FIG. 12, taken along line 22-22 of FIG. 21, where the first lever of FIG. 17 is in another unlocked lateral position.
Figure 22B:
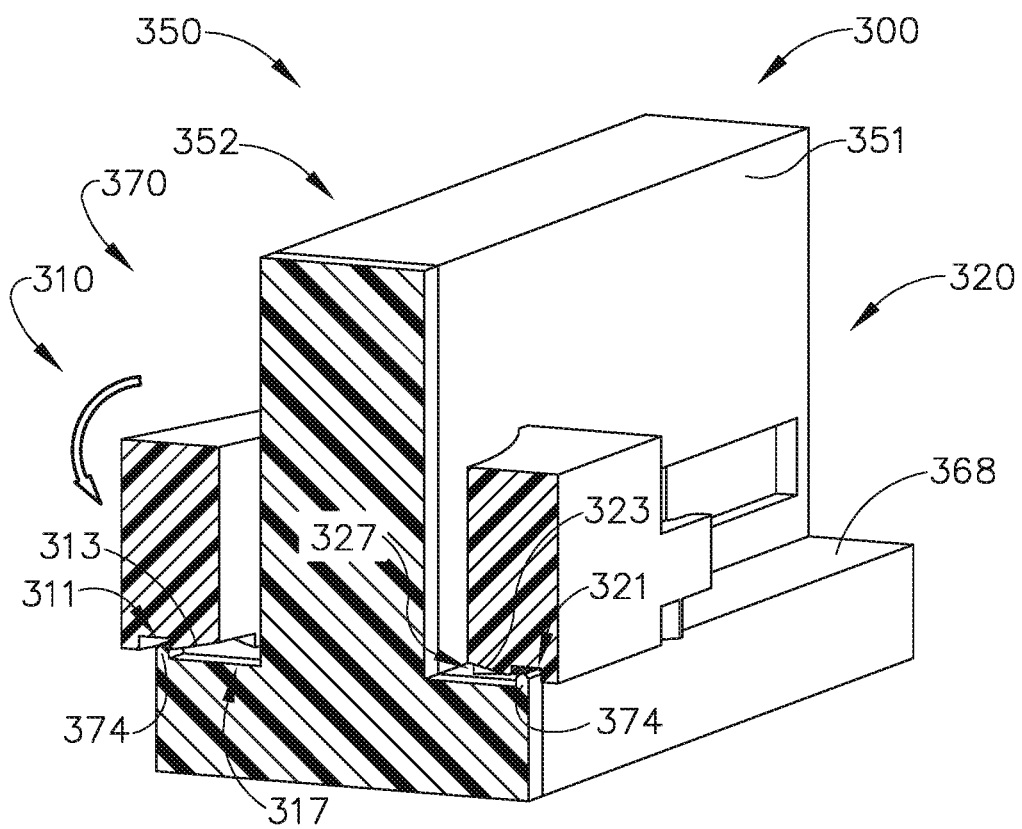
FIG. 22B depicts a cross-sectional perspective view of the firing assembly of FIG. 12, taken along line 22-22 of FIG. 21, where the first lever of FIG. 17 is in a locked position.

As shown in FIG. 22A, open end (317) is dimensioned to receive locking protrusion (374) when lever (310) is pivoted toward the fully proximal position such that locking protrusion (374) may but against sloped surface (313). FIG. 21 shows first lever (310) pivoted to a first partial laterally extended position when locking protrusions (374) is not within opening, As best shown in FIG. 22B, an operator may further pivot lever (310) toward the fully proximal position such locking protrusion (374) no longer abuts against sloped surface (313) but is housed within locking recess (311), effectively locking first lever (310). Interaction between locking protrusion (374) and locking recess (311) may help prevent first lever (310) from accidentally pivoting or actuating away from the fully proximal position. When first lever (310) is locked in the fully proximal position, first lever (310) may not translate distally due to protrusion (374) being housed within locking recess (311). However, if an operator desires to pivot first lever (310) to the laterally extended position, an operator may urge first lever (310) to pivot laterally outwards such that protrusion (374) rides against sloped surface (313) in order to "unlock" first lever (310) from locking protrusion (374). In other words, first lever (310) may pivot between the "locked" position as shown in FIG. 22B and the "unlocked" position as shown in FIG. 21 by via a snap-fit or interference fit mechanism. While in the current example, locking recess (311) and locking protrusion (374) are used to transition lever (310) between a locked and unlocked position, any other suitable means may be used as would be apparent to one having ordinary skill in the art in view of the teachings herein.

FIGS. 23A-24C show an exemplary use of firing assembly (300). FIGS. 23A and 24A show first and second levers (310, 320) both in the proximal, pre-fired, position. It should be understood that at this point, both levers (310, 320) are in a "locked position" in accordance with the description above. Next, after end effector (120) is properly grasping tissue in accordance with the description above, an operator may desire to staple and sever tissue captured between end effector (120). Therefore, as shown between FIGS. 23A-23B and 24A-24B, an operator may pivot lever (310) from the proximal pre-fired, position into the laterally extending, pre-fired position such that grasping half sleeve (318) extends into channel (358) via upper slot (360) to couple with grasping post (338) and rotational lock body (314) is inserted through pivot lock window (366) into first rotational locking pocket (334). It should be understood that while first lever (310) is pivoted into the lateral pre-fired position as shown in FIGS. 23B and 24B, second lever (320) may remain in the "locked" proximal, pre-fired position. In the current example, an operator is using first lever (310) to actuate firing assembly (300), but it should be understood that an operator may also use second lever (320), or even use both levers (310, 320) if desired.

Next, as shown in FIGS. 23C and 24C, and operator may actuate lever (310) and actuating beam (330) distally in order to staple and sever tissue captured between end effector (120) in accordance with the description above. It should be understood that second lever (320) remains in the proximal pre-fired position during the firing process in the current example. Therefore, second lever (320) may not interferer with an operator grasping instrument (100) during exemplary use. It should also be understood that while actuating beam (330) is advanced distally, grasping half sleeve (228) of second lever (220) is no longer coupled with grasping post (338). However, once actuating beam (330) completes a firing cycle and is actuated back into the proximal position, grasping post (338) and grasping half sleeve (228) may recouple.

Figure 25:
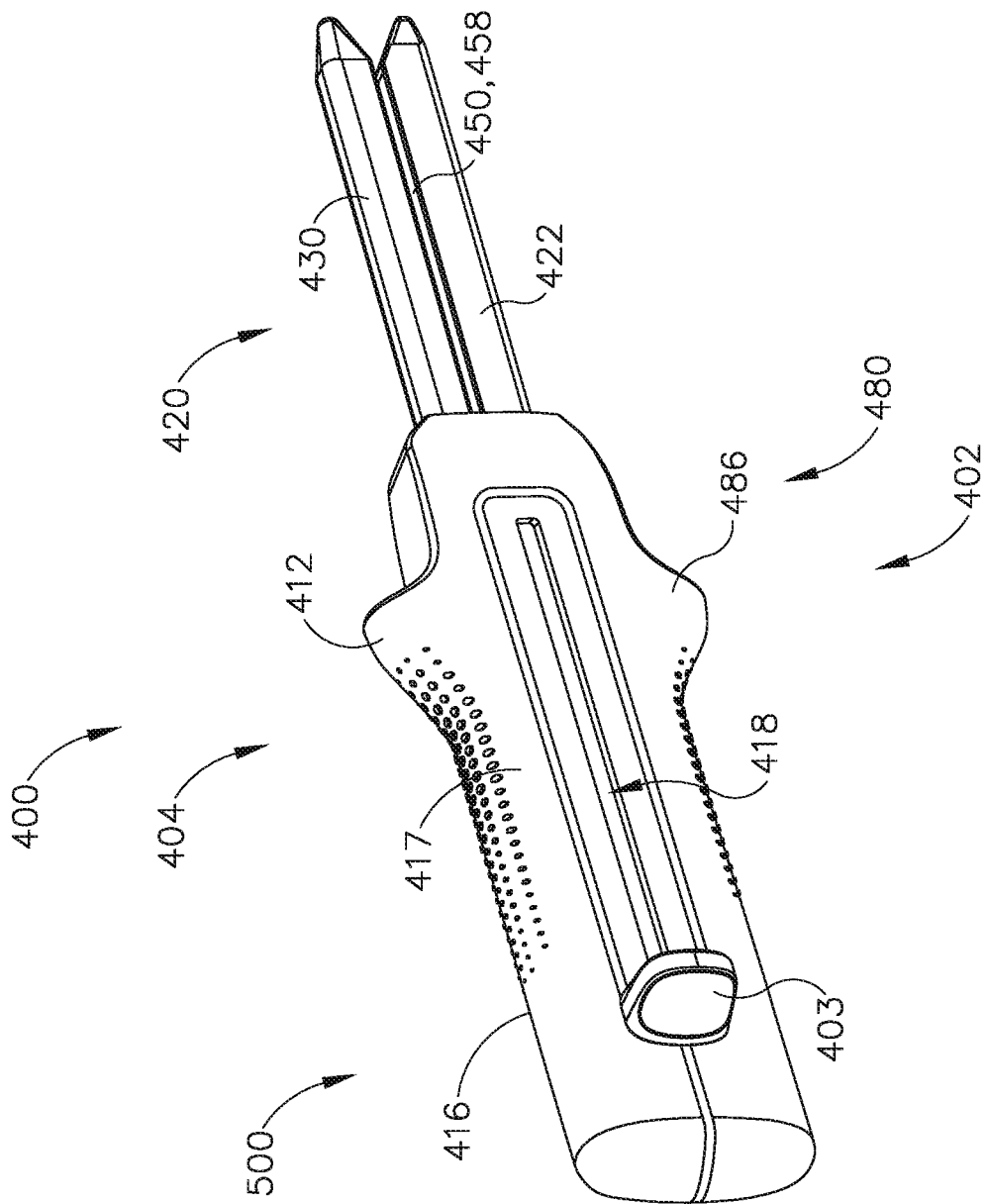
FIG. 25 depicts a perspective view of an alternative exemplary surgical stapling instrument that may be used in replacement of the surgical stapling instrument of FIG. 1.

B. Exemplary Firing Assemblies Having Dual Sided Firing Levers with Unobtrusive Profile FIG. 25 shows an alternative exemplary linear cutting stapler (400) that may used in replacement of linear cutting staple (100) described above. Stapler (400) includes a first portion (402), a second portion (404), and an end effector (420); which are substantially similar to first portion (102), second portion (104), and end effector (120) described above, with differences elaborated below. Therefore, stapler (400) has a first side (416) and a second side (417) defining slot (418) which are substantially similar to first side (116), second side (117), and slot (118) described above. Additionally, instrument (400) has a proximal end (403), an anvil, (430), a staple cartridge channel (422), a staple cartridge assembly (450), a staple deck (458), a latching lever (480), and an arm cover (486) which are substantially similar to proximal end (103), anvil, (130), staple cartridge channel (122), staple cartridge assembly (150), staple deck (158), latching lever (180), and arm cover (186) described above, respectively.

Stapler (400) in the current example has a firing assembly (500) comprising a proximal body (503), an actuating beam (502), and a staple sled assembly (501). Actuating beam (5020 and staple sled assembly (501) may be substantially similar to actuating beam (202) and staple sled assembly (160) described above. However, proximal body (503) defines a transverse channel (505) that slidable houses a sliding coupling arm (506). Sliding coupling arm (506) includes a first pin (508) and a second pin (509). First pin (508) is associated with a first lever (510) located on first side (416) while second pin (509) is associated with second lever (514) located on second side (417). As will be described in greater detail below, first lever (510) and second lever (514) are both coupled with proximal body (503) and actuating beam (502) such that both levers (510, 520) actuate with actuating beam (502) and staple sled assembly (501) during exemplary use. However, as will also be described in greater detail below, first lever (510) and second lever (514) are pivotably coupled with pins (508, 509) respectively, such that when one lever (510, 514) is pivoted to a laterally extended position, the other lever (510, 514) is pivoted inward into a non-obtrusive position such that during a firing stroke in accordance with the description above, the inward pivoted lever (510, 514) does not interfere with an operator grasping instrument (400).

Figure 26A:
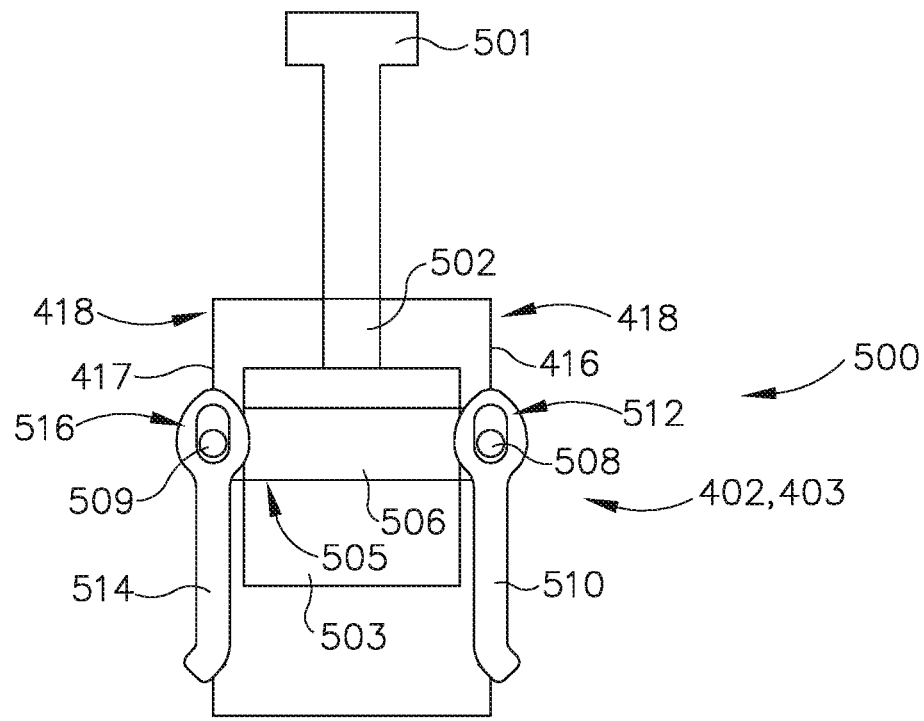
FIG. 26A depicts a top plan view of a firing assembly of the surgical stapling instrument of FIG. 25, where a first and second lever are both in a fully proximal, pre-fired, configuration.
Figure 26B:
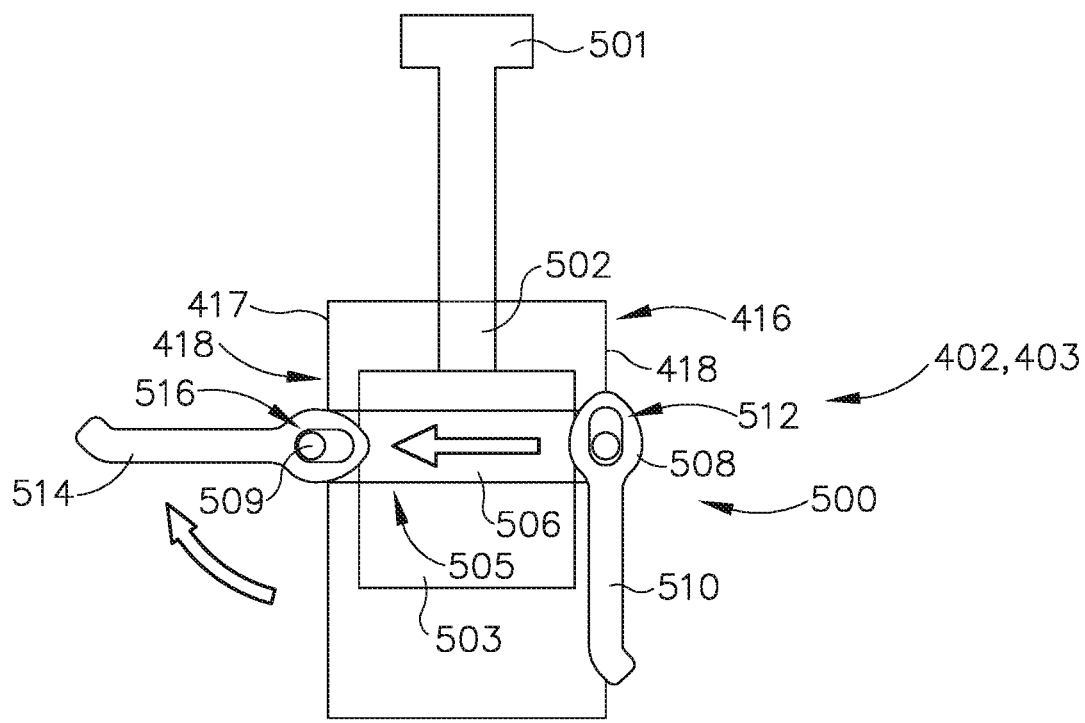
FIG. 26B depicts a top plan view of the firing assembly of FIG. 26A, where the first lever of FIG. 26A is in a laterally extended, pre-fired, configuration.

In particular, each lever (510, 520) defines a cam slot (512, 516) and houses pin (508, 509) respectively. Cam slots (512, 516) are configured to make contact with pins (508, 509) when a respective lever is pivoted to the laterally extended position. For example, FIG. 26A shows first lever (510) and second lever (514) both in a proximal, pre-fired, position. As shown in FIG. 26B, an operator may pivot second lever (514) into a laterally extended position in preparation of actuating second lever (514) to actuate firing assembly (500). When second lever (514) is pivoted into the laterally extended position, cam slot (516) makes contact with pin (509), thereby pushing pin (509) laterally away from proximal body (503). As a result, sliding coupling arm (506) slides within transverse channel (505) of proximal body (503), thereby sliding pin (508) toward proximal body (503). Pin (508) thereby makes contact with cam slot (512) in order to rotate lever (510) toward proximal body (503) into a non-obtrusive profile during firing. Therefore, when a user actuates second lever (514) to actuate firing assembly (500) in accordance with the description above, first lever (510) may not interfere with grasping of instrument (400).

Figure 26C:
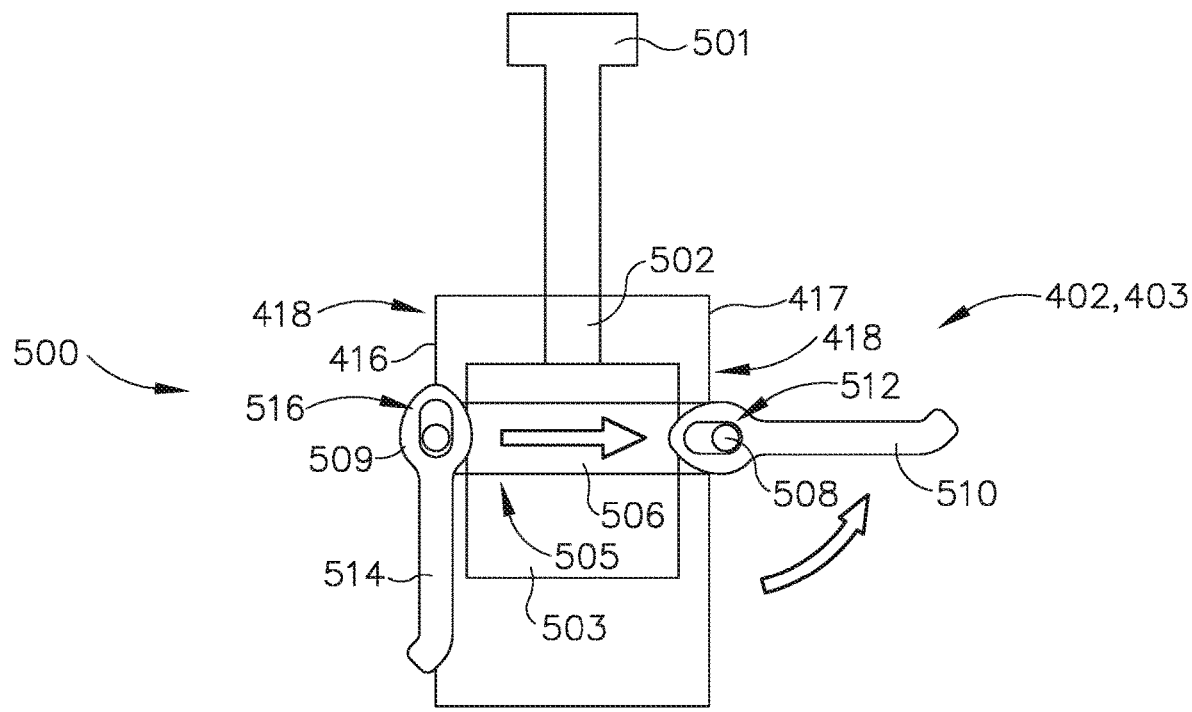
FIG. 26C depicts a top plan view of the firing assembly of FIG. 26A, where the second lever of FIG. 26A is in a laterally extended, pre-fired, configuration.

As shown in FIG. 26C, an operator may pivot first lever (510) into a laterally extended position in preparation of actuating second lever (510) to actuate firing assembly (500). When first lever (510) is pivoted into the laterally extended position, cam slot (512) makes contact with pin (508), thereby pushing pin (508) laterally away from proximal body (503). As a result, sliding coupling arm (506) slides within transverse channel (505) of proximal body (503), thereby sliding pin (509) toward proximal body (503). Pin (509) thereby makes contact with cam slot (516) in order to rotate lever (514) toward proximal body (503) into a non-obtrusive profile during firing. Therefore, when a user actuates first lever (510) to actuate firing assembly (500) in accordance with the description above, second lever (514) may not interfere with grasping of instrument (400).

Figure 27:
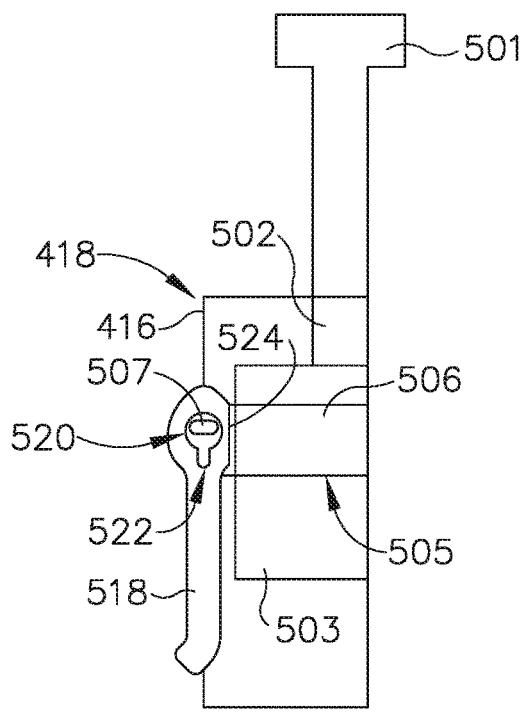
FIG. 27 depicts a top plan view of an alternative lever that may be readily incorporated into the firing assembly of FIG. 26A.

FIG. 27 shows an alternative lever (518) that may be readily incorporated into firing assembly (500) in replacement of levers (510, 514) described above. Alternative lever (518) in the current example may be substantially similar to levers (510, 514) described above, except that lever (518) defines a cam slot (520) and a locking slot (522), while sliding couple arm (506) has an alternative pin (507). Alternative lever (518) may work substantially similar to levers (510, 514) described above in that when pivoted from into the laterally extended position, cam slots (520) will interact with pin (507) in order to actuate sliding coupling arm (506) in accordance with the description above. However, once lever (518) is pivoted into the laterally extended position, pin (507) may enter into locking slot (522), thereby helping lock the angular position of lever (518) during exemplary use.

Figure 28:
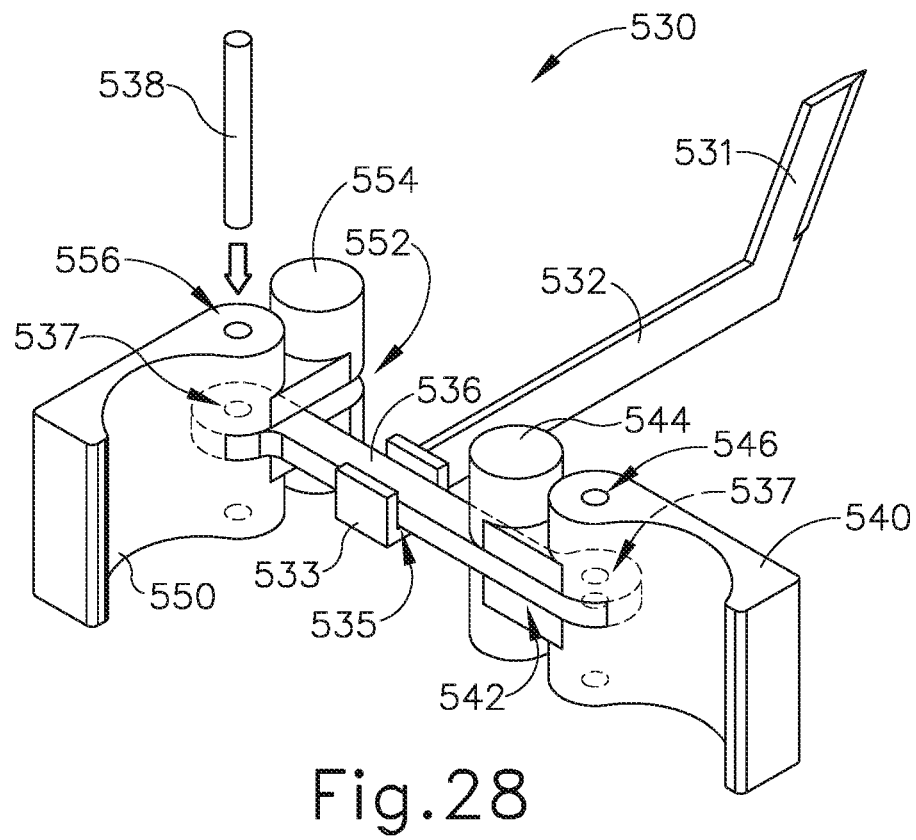
FIG. 28 depicts a perspective view of an alternative firing assembly that may be readily incorporated into either surgical stapling instrument of FIG. 1 or FIG. 25.
Figure 29:
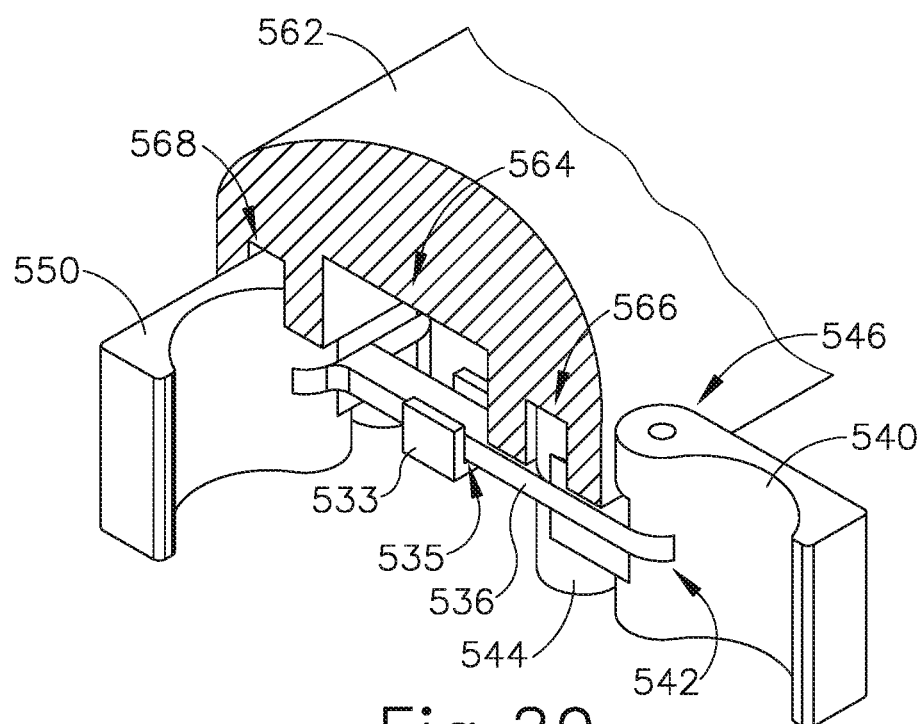
FIG. 29 depicts a perspective view of the firing assembly of FIG. 28 partially actuated distally toward a fired configuration within an alternative first portion that may be readily incorporated into either surgical stapling instrument of FIG. 1 or FIG. 25.

FIGS. 28-29 show an alternative firing assembly (530) that may be used with an alternative first portion (562). Firing assembly (530) and first portion (562) may be readily incorporated into instrument (400) in replacement of firing assembly (500) and first portion (402) described above, respectively. Firing assembly (530) includes a first firing lever (540), a second firing lever (550), includes a proximal body (533), an actuating beam (532), and a staple sled assembly (531). Actuating proximal body (533), beam (532), and staple sled assembly (531) may be substantially similar to proximal body (503), actuating beam (502), and staple sled assembly (501) described above, respectively.

Proximal body (533) defines a transverses channel (535) that slidably houses a sliding coupling arm (536). Sliding coupling arm (536) defines a pin hole (537) on opposite sides, each configured to receive a pin (538). First lever (540) and second lever (550) each define a pin hole (546, 556) dimensioned to revive pin (538) as well. Therefore, pin (538) couples levers (550, 540) with sliding coupling arm (536). Levers (540, 550) each define a reception slot (542, 552) dimensioned to receive a portion of sliding coupling arm (536) when the respective lever (540, 550) is in a laterally extended position. Additionally, each lever (540, 550) includes a camming body (544, 554), respectively. When a respective lever (540, 550) is pivoted into the laterally extended position, camming body (544) may abut against appropriate elements of first portion (562), thereby causing sliding coupling arm (536) to translate within transverse channel (535), pulling the lever (540, 550) not pivoted into the laterally extended position into a non-obtrusive position. As best seen in FIG. 29, first portion (562) defines a firing channel (562) that slidable receives actuating beam (532), a first lever channel (564), and a second lever channel (568). The lever (550) not rotated into the laterally extended position may be housed entirely within lever channel (568) during the actuation of firing assembly (530). As best seen in FIG. 29, the lever (540) in the laterally extended position may only have camming body (544) within firing channel (566) during actuating of firing assembly (530)

Figures 30A, 30B:
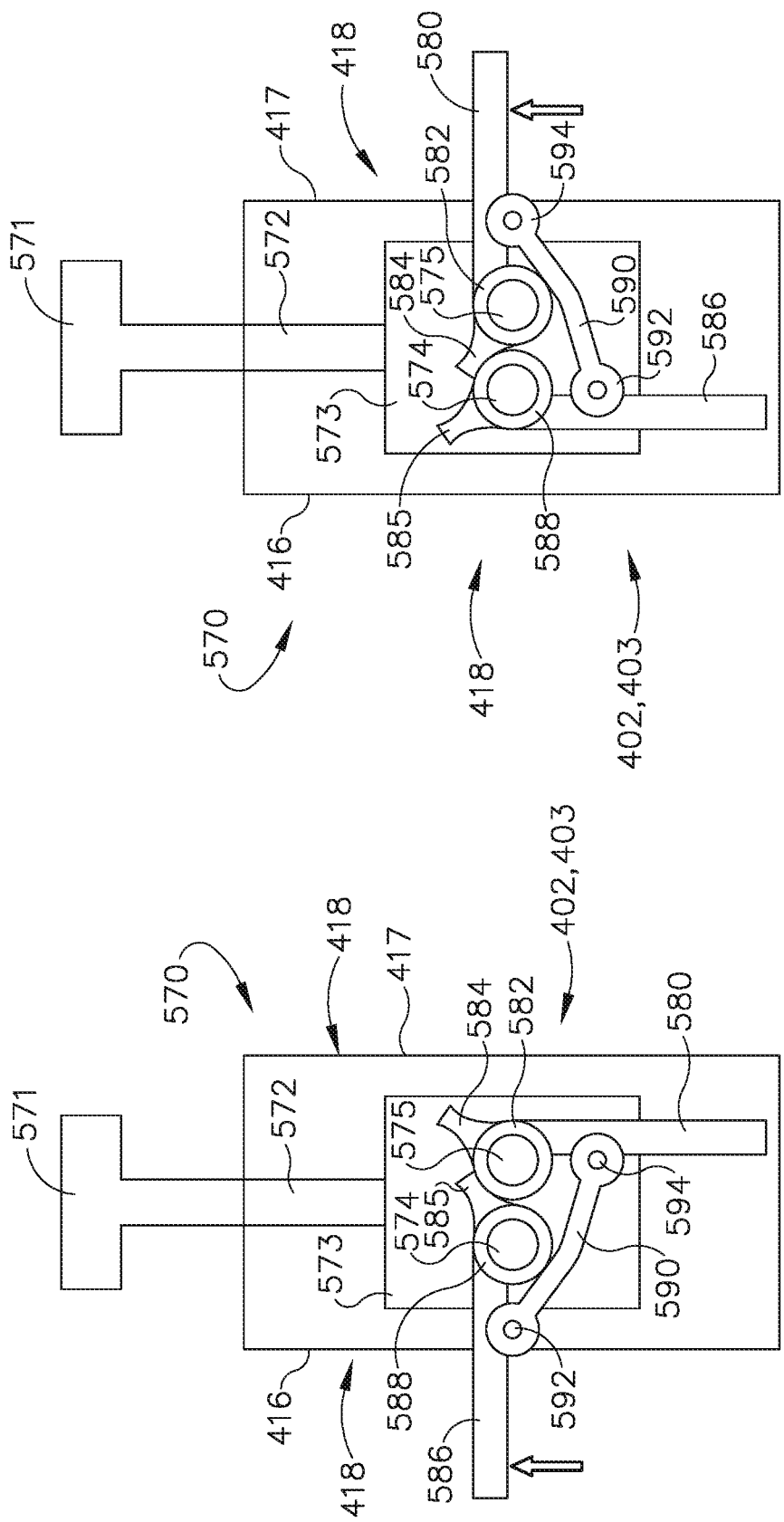
FIG. 30A depicts a top plan view alternative firing assembly that may be readily incorporated into either surgical stapling instrument of FIG. 1 or FIG. 25, where a first lever is in a fully proximal, pre-fired, configuration, where a second lever is in a laterally extended, pre-fired, configuration.
FIG. 30B depicts a top plan view of the firing assembly of FIG. 30A, where the first lever is in a laterally extended, pre-fired, configuration, where the second lever is in a fully proximal, pre-fired, configuration.

FIGS. 30A-30B show an alternative firing assembly (570) that may be readily incorporated into instrument (400) described above. Firing assembly (570) includes a proximal body (573), an actuating beam (572), a staple sled assembly (571), a first firing lever (580), a second firing lever (586), and a linkage arm (590) coupled to each firing lever (580, 586) via connecting ends (594, 592). Proximal body (573) includes pivots posts (574, 575) which are pivotably coupled with couplings sleeves (588, 582) of firings levers (586, 582). Therefore, actuation of levers (586, 582) drives proximal body (573), actuating beam (572), and staple sled assembly (571). Additionally, both levers (580, 586) actuate with actuating beam (572) and staple sled assembly (571) during exemplary use. However, first lever (580) and second lever (586) are pivotably coupled with posts (574, 575) such that when one lever (580, 586) is pivoted to a laterally extended position, the other lever (580, 586) is pivoted inward into a non-obtrusive position such that during a firing stroke in accordance with the description above, the inward pivoted lever (580, 586) does not interfere with an operator grasping instrument (400). As best seen between FIGS. 30A-30B, when one lever (580, 586) is pivoted to the laterally extended outward position, linkage arm (590) rotates the other lever (580, 586) to a non-obtrusive position. Each lever (580, 586) has a contoured contact body (584, 858) dimensioned to abut against each other when levers (580, 586) pivot to relative to each other between the positions shown in FIGS. 30A-30B.

Figure 31C:
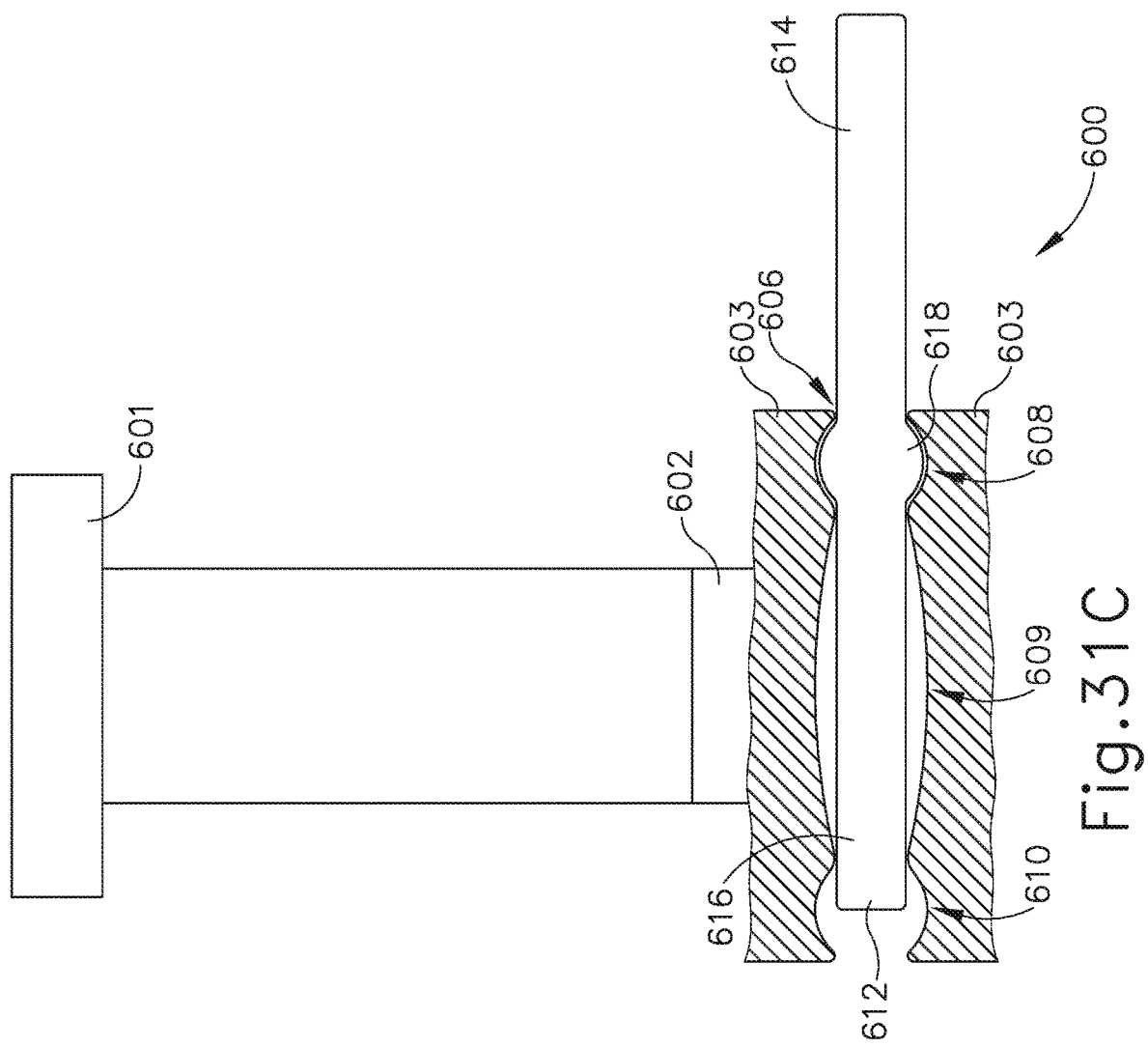
FIG. 31C depicts a top plan view of the firing assembly of FIG. 31A, where the firing lever of FIG. 31A is in a second firing configuration.

FIGS. 31A-31C show an alternative firing assembly (600) that may be readily incorporated into instrument (400) described above. Firing assembly (600) includes a proximal compliant lever retaining body (603), an actuating beam (602), a staple sled assembly (601), and a firing lever (612). Actuating beam (602) and staple sled assembly (601) are substantially similar to actuating beam (502) and staple sled assembly (501) described above. As will be described in greater detail below, firing lever (510) is configured to slide laterally within proximal compliant lever retaining body (603) such that firing lever (510) may be accessible from either side (416, 417) of instrument (400). Proximal body (603) defines a transverse channel (606) having a first side compliant chamber, a middle compliant chamber (609) and a second side compliant chamber (610). Proximal body (603) is made from a resilient material. Each compliant chamber (608, 609, 610) is configured to house a middle protrusion (618) of firing lever (612).

Firing lever (612) includes a first lateral side (614), a second lateral side (616), and middle protrusion. As best seen between FIGS. 31A-31C, firing lever (612) may slide within transverse channel (606) from a middle position (FIG. 31A), a first lateral position (FIG. 31B), and a second lateral position (FIG. 31C). As will be discussed in greater detail below, an operator may push and/or pull lever (612) between each position in order to access first lateral side (614) or second lateral side (616) for actuating firing assembly (600).

While in the middle position, middle protrusion (618) may be located within middle compliant chamber (609). The interior surfaces of proximal body (603) defining middle compliant chamber (609) are configured to engage middle protrusion (618) such that lever (612) remains stationary relative to proximal body (603). At this point, first lateral side (614) or second lateral side (616) may be partially within transverse channel (606). However, proximal body (603) is sufficiently compliant and resilient such that if an operator desires, they may slide firing lever (612) to either lateral side of proximal body (603) such that middle protrusion (618) slides within either first side compliant chamber (608) of second side compliant chamber (610). In such an instance, the interior or proximal body (603) defining transverse channel (606) may expand such that middle protrusion (618) may slide within chamber (608, 609, 610). Once middle production (618) is within either chamber (608, 609, 610) and an operator stops pushing/pulling lever (612), the compliant and/or resilient nature or proximal body (603) will reengage middle protrusion (614) of lever (612). Therefore, an operator may push/pull lever (612) laterally such that either first lateral side (614) or second lateral side (616) is exposed for grasping and firing actuating beam (602) and staple sled assembly (601).

Figure 32:
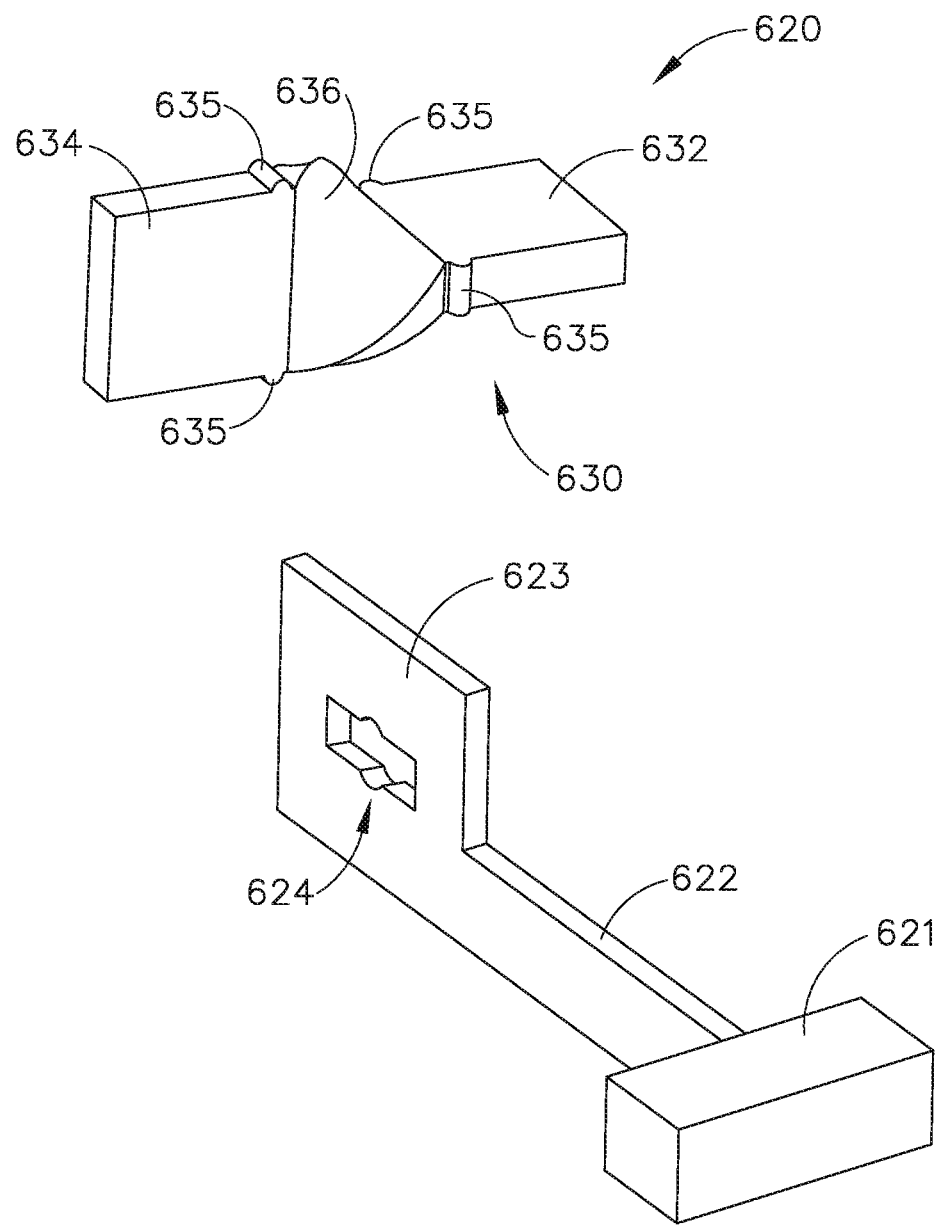
FIG. 32 depicts an exploded perspective view of an alternative firing assembly that may be readily incorporated into either surgical stapling instrument of FIG. 1 or FIG. 25.
Figure 33A:
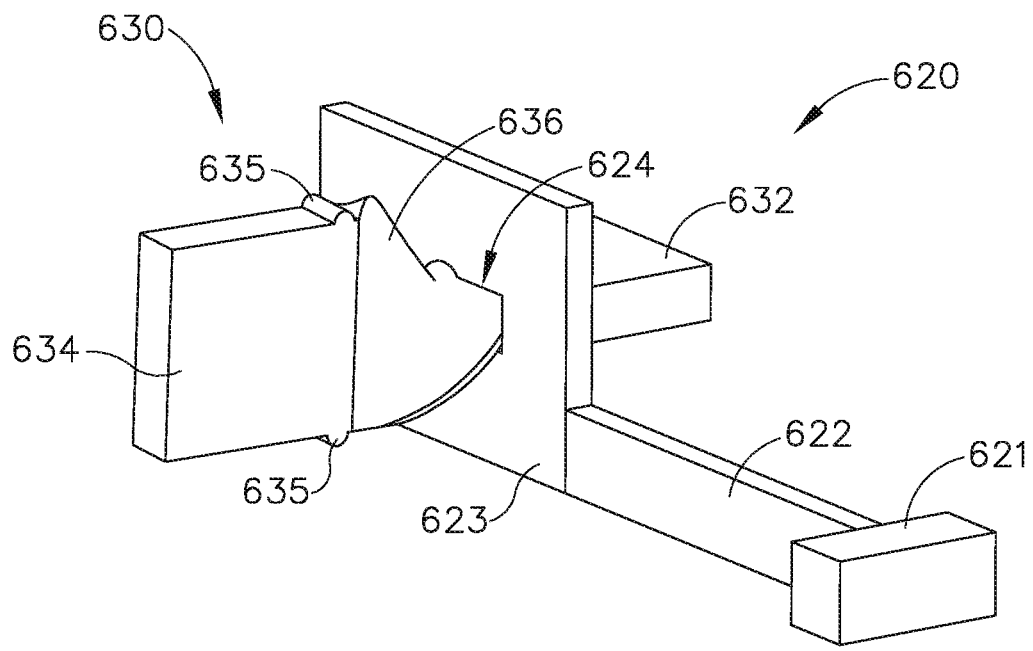
FIG. 33A depicts a perspective view of the firing assembly of FIG. 32; where a firing lever is in a first lateral configuration.
Figure 33B:
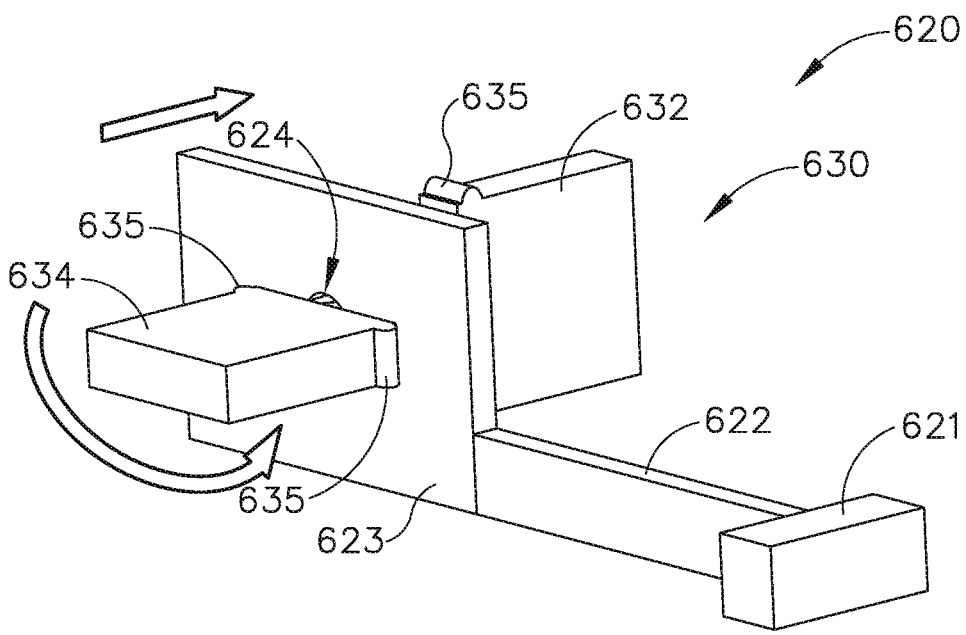
FIG. 33B depicts a perspective view of the firing assembly of FIG. 32, where the firing lever of FIG. 33A is in a second lateral configuration.

FIGS. 32-33 show another firing assembly (620) that may be readily incorporated into instrument (400). Firing assembly (600) includes a proximal body (623) defining a cam slot (624), an actuating beam (622) coupled to proximal body (623), a staple sled assembly (621) coupled with actuating beam (622), and a firing lever (630). Actuating beam (622) and staple sled assembly (621) may be substantially similar to actuating beam (502) and staple sled assembly (501) described above. As will be described in greater detail below, a portion of firing lever (630) is slidable coupled within the confines of cam slot (624) such that when firing lever (630) is pushed or pulled laterally, firing lever (330) rotates.

Firing lever (630) includes a first firing arm (632), a second firing arm (634), a torsional portion (636) located between first firing arm (632) and second firing arm (634), and lateral protrusions (635) located along portions of first firing arm (632) and second firing arm (634) adjacent to torsional portion (636). Torsional portion (636) is within the confines of cam slot (624) such that an operator may push or pull firing lever (630) such that torsional portion (636) and cam slot (624) interact with each other in order to rotate firing lever (630) relative to proximal body (623). In particular, when firing lever (630) is in the position shown in FIG. 33A, second firing arm (634) may be grasped for actuating firing assembly (620). When firing lever (630) is in the position shown in FIG. 33B, first firing arm (632) may be grasped for actuating firing assembly (620). Therefore, an operator may push/pull on firing lever (630) toward the side in which an operator wishes to grasp firing lever (630).

Lateral protrusion (635) are dimensioned to prevent firing lever (630) from disassociating with proximal body (623).

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, the apparatus comprising: (a) a handle assembly, wherein the handle assembly comprises: (i) a first lateral side, (ii) a second lateral side, (iii) a first arm, (iv) a second arm, wherein the second arm is configured to pivotably couple with the first arm at a proximal pivot location, and (v) a latching lever pivotably coupled with the first arm at a distal pivot location; (b) an end effector, wherein the end effector comprises: (i) a first jaw extending distally from the first arm, and (ii) a second jaw extending distally from the second arm, wherein the second jaw is configured to pivot relative to the first jaw between an open configuration, a partially closed configuration, and a fully closed configuration, wherein the latching lever is configured engage the second arm or the second jaw to pivot the second jaw from the partially closed configuration toward the fully closed configuration; and (c) a firing assembly configured to sever tissue captured between the first jaw and the second jaw in the fully closed configuration, wherein the firing assembly comprises: (i) an actuating beam slidable relative to the handle assembly and the end effector, (ii) a proximal body coupled to the actuating beam, wherein the proximal body is slidably housed within either the first arm or the second arm, (iii) a first lever associated with the first lateral side configured to move between a first laterally extending position and a first non-obtrusive position, wherein the first lever is configured to drive the actuating beam and the proximal body relative to the handle assembly in the first laterally extending position, and (iv) a second lever associated with the second lateral side configured to move between a second laterally extending position and a second non-obtrusive position, wherein the second lever is configured to drive the actuating beam and the proximal body relative to the handle assembly in the second laterally extending position.

Example 2

The apparatus of Example 1, wherein the proximal body comprises a first post and a second post.

Example 3

The apparatus of Example 2, wherein the first lever comprises pivoting connector and a grasping connector, wherein the pivoting connector is configured to pivotably couple the first lever with the first post while the proximal body is in a proximal position.

Example 4

The apparatus of Example 3, wherein the grasping connector is configured to couple with the second post in the first laterally extending position, wherein the grasping connector is configured to decouple with the second post in the first non-obtrusive position.

Example 5

The apparatus of Example 4, wherein the first lever is configured to drive the actuating beam independently of the second lever.

Example 6

The apparatus of any one or more of Examples 4 through 5, wherein the first arm defines an upper slot on the first lateral side and a lower slot on the second lateral side, wherein the grasping connector is first configured to pass through the upper slot of the first lateral side when moving between the first lateral position and the first non-obtrusive position.

Example 7

The apparatus of any one or more of Examples 1 through 6, wherein the proximal body defines a rotational locking pocket configured to receive a portion of the first lever in the first lateral position.

Example 8

The apparatus of any one or more of Examples 1 through 7, wherein the first lever is configured to selectively lock into the non-obtrusive position via a snap-fit connection.

Example 9

The apparatus of any one or more of Examples 1 through 8, wherein the first lever and the second lever are configured to actuate together with the proximal body relative to the handle assembly.

Example 10

The apparatus of Example 9, wherein the proximal body defines a transverse channel, wherein the first lever and the second lever are connected with each other by a linkage arm.

Example 11

The apparatus of any one or more of Examples 9 through 10, wherein the proximal body defines a transverse channel, wherein the first lever and the second lever are connected to each other by a sliding coupling arm.

Example 12

The apparatus of Example 11, wherein the first lever defines a first cam slot, wherein the first lever is coupled with the sliding coupling arm via a first pin and the first cam slot.

Example 13

The apparatus of Example 12, wherein the second lever defines a second cam slot, wherein the second lever is coupled with the sliding coupling arm via a second pin and the second cam slot.

Example 14

The apparatus of any one or more of Examples 1 through 13, wherein the first lever also defines a locking slot configured to rotationally lock the first lever in the first lateral position.

Example 15

The apparatus of any one or more of Examples 1 through 14, wherein the first handle defines a firing channel housing the actuating beam, wherein the first handle further defines a first lever channel configured to receive the first lever in the first non-obtrusive position.

Example 16

The apparatus of Example 15, wherein the first handle further defines a second lever channel configured to receive the second lever in the second non-obtrusive position.

Example 17

An apparatus, the apparatus comprising: (a) a handle assembly, wherein the handle assembly comprises: (i) a first lateral side, (ii) a second lateral side, (iii) a first arm, (iv) a second arm, wherein the second arm is configured to pivotably couple with the first arm at a proximal pivot location, and (v) a latching lever pivotably coupled with the first arm at a distal pivot location; (b) an end effector, wherein the end effector comprises: (i) a first jaw extending distally from the first arm, and (ii) a second jaw extending distally from the second arm, wherein the second jaw is configured to pivot relative to the first jaw between an open configuration, a partially closed configuration, and a fully closed configuration, wherein the latching lever is configured engage the second arm or the second jaw to pivot the second jaw from the partially closed configuration toward the fully closed configuration; and (c) a firing assembly configured to sever tissue captured between the first jaw and the second jaw in the fully closed configuration, wherein the firing assembly comprises: (i) an actuating beam slidable relative to the handle assembly and the end effector, (ii) a first lever associated with the first lateral side configured to pivot between a first laterally extending position and a first non-obtrusive position, wherein the first lever is configured to drive the actuating beam relative to the handle assembly in the first laterally extending position, and (iv) a second lever configured associated with the second lateral side configured to pivot between a second laterally extending position and a second non-obtrusive position, wherein the second lever is configured to drive the actuating beam relative to the handle assembly in the second laterally extending position.

Example 18

The apparatus of Example 17, wherein the first arm defines an upper slot associated with the first lateral side, wherein the first arm defines a lower slot associated with the second lateral side, wherein the first lever is slidably coupled with the upper slot, wherein the second lever is slidably coupled with the lower slot.

Example 19

The apparatus of Example 18, wherein the upper slot further defines a pivot lock window configured to receive a rotational lock body of the first lever in the first laterally extending position.

Example 20

An apparatus, the apparatus comprising: (a) a handle assembly, wherein the handle assembly comprises: (i) a first lateral side, (ii) a second lateral side, (iii) a first arm, (iv) a second arm, wherein the second arm is configured to pivotably couple with the first arm at a proximal pivot location, and (v) a latching lever pivotably coupled with the first arm at a distal pivot location; (b) an end effector, wherein the end effector comprises: (i) a first jaw extending distally from the first arm, and (ii) a second jaw extending distally from the second arm, wherein the second jaw is configured to pivot relative to the first jaw between an open configuration, a partially closed configuration, and a fully closed configuration, wherein the latching lever is configured engage the second arm or the second jaw to pivot the second jaw from the partially closed configuration toward the fully closed configuration; and (c) a firing assembly configured to sever tissue captured between the first jaw and the second jaw in the fully closed configuration, wherein the firing assembly comprises: (i) a first lever associated with the first lateral side configured to move between a first laterally extending position and a first non-obtrusive position, wherein the first lever is configured to drive a selected portion of the firing assembly relative to the handle assembly in the first laterally extending position, and (ii) a second lever configured associated with the second lateral side configured to move between a second laterally extending position and a second non-obtrusive position, wherein the second lever is configured to drive the selected portion of the firing assembly relative to the handle assembly in the second laterally extending position.

IV. Miscellaneous

Any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/889,363, entitled "Release Mechanism for Linear Surgical Stapler," filed on Feb. 6, 2018, issued as U.S. Pat. No. 10,631,866 on Apr. 28, 2020; U.S. application Ser. No. 15/889,370, entitled "Lockout Assembly for Linear Surgical Stapler," filed on Feb. 6, 2018, issued as U.S. Pat. No. 10,667,818 on Jun. 2, 2020; U.S. application Ser. No.

15/889,374, entitled "Features to Align and Close Linear Surgical Stapler," filed on Feb. 6, 2018, published as U.S. Pub. No. 2019/0239886 on Aug. 8, 2019; U.S. App. Ser. No. 15/889,376, entitled "Releasable Coupling Features for Proximal Portions of Linear Surgical Stapler," filed on Feb. 6, 2018, published as U.S. Pub. No. 2019/0239883 on Aug. 8, 2019; and U.S. application Ser. No. 15/889,363, entitled "Clamping Mechanism for Linear Surgical Stapler," filed on Feb. 6, 2018, issued as U.S. Pat. No. 10,687,819 on Jun. 23, 2020. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, the apparatus comprising:
   (a) a handle assembly, wherein the handle assembly comprises:
      (i) a first lateral side,
      (ii) a second lateral side,
      (iii) a first arm,
      (iv) a second arm, wherein the second arm is configured to pivotably couple with the first arm at a proximal pivot location, and
      (v) a latching lever pivotably coupled with the first arm at a distal pivot location;
   (b) an end effector, wherein the end effector comprises:
      (i) a first jaw extending distally from the first arm, and
      (ii) a second jaw extending distally from the second arm, wherein the second jaw is configured to pivot relative to the first jaw between an open configuration, and a closed configuration, wherein the latching lever is configured to engage the second arm or the second jaw to pivot the second jaw from the open configuration toward the closed configuration; and
   (c) a firing assembly configured to sever tissue captured between the first jaw and the second jaw in the closed configuration, wherein the firing assembly comprises:
      (i) an actuating beam slidable relative to the handle assembly and the end effector, wherein the first arm defines a firing channel configured to house the actuating beam,
      (ii) a proximal body coupled to the actuating beam, wherein the proximal body is slidably housed within either the first arm or the second arm,
      (iii) a first lever associated with the first lateral side configured to move between a first laterally extending position and a first non-obtrusive position, wherein the first lever is configured to drive the actuating beam and the proximal body relative to the handle assembly in the first laterally extending position, wherein the first arm further defines a first lever channel configured to receive the first lever in the first non-obtrusive position, and
      (iv) a second lever associated with the second lateral side configured to move between a second laterally extending position and a second non-obtrusive position, wherein the second lever is configured to drive the actuating beam and the proximal body relative to the handle assembly in the second laterally extending position.

2. The apparatus of claim 1, wherein the proximal body comprises a first post and a second post.

3. The apparatus of claim 2, wherein the first lever comprises pivoting connector and a grasping connector, wherein the pivoting connector is configured to pivotably couple the first lever with the first post while the proximal body is in a proximal position.

4. The apparatus of claim 3, wherein the grasping connector is configured to couple with the second post in the first laterally extending position, wherein the grasping connector is configured to decouple with the second post in the first non-obtrusive position.

5. The apparatus of claim 4, wherein the first lever is configured to drive the actuating beam independently of the second lever.

6. The apparatus of claim 4, wherein the first arm defines an upper slot on the first lateral side and a lower slot on the second lateral side, wherein the grasping connector is first configured to pass through the upper slot of the first lateral side when moving between the first lateral position and the first non-obtrusive position.

7. The apparatus of claim 1, wherein the proximal body defines a rotational locking pocket configured to receive a portion of the first lever in the first lateral position.

8. The apparatus of claim 1, wherein the first lever is configured to selectively lock into the non-obtrusive position via a snap-fit connection.

9. The apparatus of claim 1, wherein the first lever and the second lever are configured to actuate together with the proximal body relative to the handle assembly.

10. The apparatus of claim 9, wherein the proximal body defines a transverse channel, wherein the first lever and the second lever are connected with each other by a linkage arm.

11. The apparatus of claim 9, wherein the proximal body defines a transverse channel, wherein the first lever and the second lever are connected to each other by a sliding coupling arm.

12. The apparatus of claim 11, wherein the first lever defines a first cam slot, wherein the first lever is coupled with the sliding coupling arm via a first pin and the first cam slot.

13. The apparatus of claim 12, wherein the second lever defines a second cam slot, wherein the second lever is coupled with the sliding coupling arm via a second pin and the second cam slot.

14. The apparatus of claim 1, wherein the first lever also defines a locking slot configured to rotationally lock the first lever in the first lateral position.

15. The apparatus of claim 1, wherein the first arm further defines a second lever channel configured to receive the second lever in the second non-obtrusive position.

16. An apparatus, the apparatus comprising:
 (a) a handle assembly, wherein the handle assembly comprises:
  (i) a first lateral side,
  (ii) a second lateral side,
  (iii) a first arm,
  (iv) a second arm, wherein the second arm is configured to pivotably couple with the first arm at a proximal pivot location, and
  (v) a latching lever pivotably coupled with the first arm at a distal pivot location;
 (b) an end effector, wherein the end effector comprises:
  (i) a first jaw extending distally from the first arm, and
  (ii) a second jaw extending distally from the second arm, wherein the second jaw is configured to pivot relative to the first jaw between an open configuration, and a closed configuration, wherein the latching lever is configured to engage the second arm or the second jaw to pivot the second jaw from the open configuration toward the closed configuration; and
 (c) a firing assembly configured to sever tissue captured between the first jaw and the second jaw in the closed configuration, wherein the firing assembly comprises:
  (i) an actuating beam slidable relative to the handle assembly and the end effector,
  (ii) a first lever associated with the first lateral side configured to pivot between a first laterally extending position and a first non-obtrusive position, wherein the first lever is configured to drive the actuating beam relative to the handle assembly in the first laterally extending position, and
  (iii) a second lever associated with the second lateral side configured to pivot between a second laterally extending position and a second non-obtrusive position, wherein the second lever is configured to drive the actuating beam relative to the handle assembly in the second laterally extending position, wherein the first lever, while in the first laterally extending position, is configured to actuate away from the second lever in order to drive the actuating beam relative to the handle assembly.

17. The apparatus of claim 16, wherein the first arm defines an upper slot associated with the first lateral side, wherein the first arm defines a lower slot associated with the second lateral side, wherein the first lever is slidably coupled with the upper slot, wherein the second lever is slidably coupled with the lower slot.

18. The apparatus of claim 17, wherein the upper slot further defines a pivot lock window configured to receive a rotational lock body of the first lever in the first laterally extending position.

19. An apparatus, the apparatus comprising:
 (a) a handle assembly, wherein the handle assembly comprises:
  (i) a first lateral side,
  (ii) a second lateral side,
  (iii) a first arm,
  (iv) a second arm, wherein the second arm is configured to pivotably couple with the first arm at a proximal pivot location, and
  (v) a latching lever pivotably coupled with the first arm at a distal pivot location;
 (b) an end effector, wherein the end effector comprises:
  (i) a first jaw extending distally from the first arm, and
  (ii) a second jaw extending distally from the second arm, wherein the second jaw is configured to pivot relative to the first jaw between an open configuration, and a fully closed configuration, wherein the latching lever is configured to engage the second arm or the second jaw to pivot the second jaw from the open configuration toward the closed configuration; and
 (c) a firing assembly configured to sever tissue captured between the first jaw and the second jaw in the closed configuration, wherein the firing assembly comprises:
  (i) a proximal body slidably housed within the handle assembly, wherein the proximal body defines a slot,
  (ii) a first lever associated with the first lateral side configured to move between a first laterally extending position and a first non-obtrusive position, wherein the first lever is configured to drive a selected portion of the firing assembly relative to the handle assembly in the first laterally extending position,
  (iii) a second lever associated with the second lateral side configured to move between a second laterally extending position and a second non-obtrusive position, wherein the second lever is configured to drive the selected portion of the firing assembly relative to the handle assembly in the second laterally extending position, wherein the first lever and the second lever are configured to actuate together with the proximal body relative to the handle assembly, and (iv) a sliding member coupled between the first and second levers.

20. The apparatus of claim 19, wherein the first lever is coupled to the sliding coupling arm by a first pin and the second lever is coupled to the sliding coupling arm with a second pin.

* * * * *